US011793912B2

(12) United States Patent
Faucher et al.

(10) Patent No.: US 11,793,912 B2
(45) Date of Patent: *Oct. 24, 2023

(54) CROSS-LINKED FATTY ACID-BASED BIOMATERIALS

(71) Applicant: ATRIUM MEDICAL CORPORATION, Merrimack, NH (US)

(72) Inventors: Keith M. Faucher, Milford, NH (US); Hui Tang, Acton, MA (US); Paul Martakos, Pelham, NH (US); Theodore Karwoski, Moultonborough, NH (US); Alison Sullivan, Acton, MA (US); Greg Melville, Hudson, NH (US); Scott E. Corbeil, Litchfield, NH (US)

(73) Assignee: ATRIUM MEDICAL CORPORATION, Merrimack, NH (US)

( * ) Notice: Subject to any disclaimer, the term of this patent is extended or adjusted under 35 U.S.C. 154(b) by 405 days.

This patent is subject to a terminal disclaimer.

(21) Appl. No.: 17/066,466

(22) Filed: Oct. 8, 2020

(65) Prior Publication Data

US 2021/0030928 A1 Feb. 4, 2021

Related U.S. Application Data

(60) Division of application No. 15/794,086, filed on Oct. 26, 2017, now Pat. No. 10,814,043, which is a division of application No. 14/679,368, filed on Apr. 6, 2015, now Pat. No. 9,827,352, which is a continuation of application No. 12/364,763, filed on Feb. 3, 2009, now Pat. No. 9,000,040, which is a continuation-in-part of application No. 11/582,135, filed on Oct. 16, 2006, now Pat. No. 8,124,127, said application No. 12/364,763 is a continuation-in-part of application No. 11/236,908, filed on Sep. 28, 2005, and a continuation-in-part of application No. 11/237,264, filed on Sep. 28, 2005, now Pat. No. 8,795,703.

(60) Provisional application No. 61/104,575, filed on Oct. 10, 2008, provisional application No. 61/104,568, filed on Oct. 10, 2008, provisional application No. 60/727,312, filed on Oct. 15, 2005, provisional application No. 60/613,745, filed on Sep. 28, 2004, provisional application No. 60/613,808, filed on Sep. 28, 2004.

(51) Int. Cl.
*A61L 31/08* (2006.01)
*A61L 31/16* (2006.01)
*A61K 31/4353* (2006.01)
*A61L 31/14* (2006.01)
*A61F 2/82* (2013.01)

(52) U.S. Cl.
CPC .......... *A61L 31/08* (2013.01); *A61K 31/4353* (2013.01); *A61L 31/148* (2013.01); *A61L 31/16* (2013.01); *A61F 2/82* (2013.01); *A61F 2250/0067* (2013.01); *A61L 2300/404* (2013.01); *A61L 2300/606* (2013.01); *A61L 2420/06* (2013.01); *A61L 2430/00* (2013.01)

(58) Field of Classification Search
CPC ............. A61L 31/08; A61L 31/16; A61F 2/82
See application file for complete search history.

(56) References Cited

U.S. PATENT DOCUMENTS

| | | |
|---|---|---|
| 1,948,959 A | 2/1934 | Croce |
| 2,368,306 A | 1/1945 | Kiefer et al. |
| 2,403,458 A | 7/1946 | Ransom et al. |
| 2,555,976 A | 6/1951 | Keenan |
| 2,735,814 A | 2/1956 | Hodson et al. |
| 2,986,540 A | 5/1961 | Posnansky |
| 3,328,259 A | 6/1967 | Anderson |
| 3,464,413 A | 9/1969 | Goldfarb et al. |
| 3,556,294 A | 1/1971 | Waick et al. |
| 3,567,820 A | 3/1971 | Sperti |
| 3,803,109 A | 4/1974 | Nemoto et al. |
| 3,967,728 A | 7/1976 | Gordon et al. |
| 4,185,637 A | 1/1980 | Mattei |
| 4,308,120 A | 12/1981 | Pennewiss et al. |
| 4,323,547 A | 4/1982 | Knust et al. |
| 4,345,414 A | 8/1982 | Bornat et al. |
| 4,447,418 A | 5/1984 | Maddoux |

(Continued)

FOREIGN PATENT DOCUMENTS

| | | |
|---|---|---|
| CN | 1360951 | 7/2002 |
| CN | 1429559 | 7/2003 |

(Continued)

OTHER PUBLICATIONS

Nutritionix (https://www.nutritionix.com/food/fish-oil-supplement), pp. 1-2, accessed Jan. 24, 2023 (Year: 2023).*

(Continued)

*Primary Examiner* — Andrew S Rosenthal

(57) ABSTRACT

Fatty acid-based, pre-cure-derived biomaterials, methods of making the biomaterials, and methods of using them as drug delivery carriers are described. The fatty acid-derived biomaterials can be utilized alone or in combination with a medical device for the release and local delivery of one or more therapeutic agents. Methods of forming and tailoring the properties of said biomaterials and methods of using said biomaterials for treating injury in a mammal are also provided.

20 Claims, 30 Drawing Sheets

(56) References Cited

U.S. PATENT DOCUMENTS

| | | |
|---|---|---|
| 4,557,925 A | 12/1985 | Lindahl et al. |
| 4,655,221 A | 4/1987 | Devereux |
| 4,664,114 A | 5/1987 | Ghodstain |
| 4,702,252 A | 10/1987 | Brooks et al. |
| 4,711,902 A | 12/1987 | Serno |
| 4,733,665 A | 3/1988 | Palmaz |
| 4,769,038 A | 9/1988 | Bendavid et al. |
| 4,813,210 A | 3/1989 | Masuda et al. |
| 4,814,329 A | 3/1989 | Harsanyi et al. |
| 4,824,436 A | 4/1989 | Wolinsky |
| 4,846,844 A | 7/1989 | De Leon et al. |
| 4,847,301 A | 7/1989 | Muuray |
| 4,880,455 A | 11/1989 | Blank |
| 4,886,787 A | 12/1989 | de Belder et al. |
| 4,894,231 A | 1/1990 | Moreau et al. |
| 4,895,724 A | 1/1990 | Cardinal et al. |
| 4,911,707 A | 3/1990 | Heiber et al. |
| 4,937,254 A | 6/1990 | Sheffield et al. |
| 4,938,763 A | 7/1990 | Dunn et al. |
| 4,941,308 A | 7/1990 | Grabenkort et al. |
| 4,941,877 A | 7/1990 | Montano, Jr. |
| 4,947,840 A | 8/1990 | Yannas et al. |
| 4,952,419 A | 8/1990 | de Leon |
| 4,968,302 A | 11/1990 | Schluter et al. |
| 4,994,033 A | 2/1991 | Shockey et al. |
| 5,017,229 A | 5/1991 | Burns et al. |
| 5,019,096 A | 5/1991 | Fox, Jr. et al. |
| 5,041,125 A | 8/1991 | Montano, Jr. |
| 5,049,132 A | 9/1991 | Shaffer et al. |
| 5,061,281 A | 10/1991 | Mares et al. |
| 5,071,609 A | 12/1991 | Tu et al. |
| 5,087,244 A | 2/1992 | Wolinsky et al. |
| 5,087,246 A | 2/1992 | Smith |
| 5,102,402 A | 4/1992 | Dror et al. |
| 5,118,493 A | 6/1992 | Kelley et al. |
| 5,132,115 A | 7/1992 | Wolter et al. |
| 5,147,374 A | 9/1992 | Fernandez |
| 5,151,272 A | 9/1992 | Engstrom et al. |
| 5,171,148 A | 12/1992 | Wasserman et al. |
| 5,179,174 A | 1/1993 | Elton |
| 5,199,951 A | 4/1993 | Spears |
| 5,202,310 A | 4/1993 | Levy et al. |
| 5,206,077 A | 4/1993 | Cowley et al. |
| 5,176,956 A | 5/1993 | Jevne et al. |
| 5,254,105 A | 10/1993 | Haaga |
| 5,267,985 A | 12/1993 | Shimada et al. |
| 5,279,565 A | 1/1994 | Klein et al. |
| 5,282,785 A | 2/1994 | Shapland et al. |
| 5,283,257 A | 2/1994 | Gregory et al. |
| 5,286,254 A | 2/1994 | Shapland et al. |
| 5,295,962 A | 3/1994 | Crocker et al. |
| 5,304,121 A | 4/1994 | Sahatjian |
| 5,336,178 A | 8/1994 | Kaplan et al. |
| 5,356,432 A | 10/1994 | Rutkow et al. |
| 5,368,602 A | 11/1994 | de la Torre |
| 5,371,109 A | 12/1994 | Engstrom et al. |
| 5,380,328 A | 1/1995 | Morgan |
| 5,387,658 A | 2/1995 | Schroder et al. |
| 5,403,283 A | 4/1995 | Luther |
| 5,411,951 A | 5/1995 | Mitchell |
| 5,411,988 A | 6/1995 | Bockow et al. |
| 5,447,940 A | 9/1995 | Harvey et al. |
| 5,456,666 A | 10/1995 | Campbell et al. |
| 5,456,720 A | 10/1995 | Schultz et al. |
| 5,458,568 A | 10/1995 | Racchini et al. |
| 5,458,572 A | 10/1995 | Racchini et al. |
| 5,464,650 A | 11/1995 | Berg et al. |
| 5,468,242 A | 11/1995 | Reisberg |
| 5,480,436 A | 1/1996 | Bakker et al. |
| 5,480,653 A | 1/1996 | Aguadish et al. |
| 5,490,839 A | 2/1996 | Wang et al. |
| 5,498,238 A | 3/1996 | Shapland et al. |
| 5,499,971 A | 3/1996 | Shapland et al. |
| 5,502,077 A | 3/1996 | Breivik et al. |
| 5,509,899 A | 4/1996 | Fan et al. |
| 5,514,092 A | 5/1996 | Forman et al. |
| 5,547,677 A | 8/1996 | Wright |
| 5,549,901 A | 8/1996 | Wright |
| 5,558,071 A | 9/1996 | Ward et al. |
| 5,569,198 A | 10/1996 | Racchini |
| 5,579,149 A | 11/1996 | Moret et al. |
| 5,573,781 A | 12/1996 | Brown et al. |
| 5,580,923 A | 12/1996 | Yeung et al. |
| 5,589,508 A | 12/1996 | Schlotzer et al. |
| 5,591,230 A | 1/1997 | Horn et al. |
| 5,593,441 A | 1/1997 | Lichtenstein et al. |
| 5,603,721 A | 2/1997 | Lau et al. |
| 5,605,696 A | 2/1997 | Eury et al. |
| 5,612,074 A | 3/1997 | Leach |
| 5,614,284 A | 3/1997 | Kranzler |
| 5,627,077 A | 5/1997 | Dyllick-Brenzinger et al. |
| 5,628,730 A | 5/1997 | Shapland et al. |
| 5,629,021 A | 5/1997 | Wright |
| 5,634,899 A | 6/1997 | Shapland et al. |
| 5,634,931 A | 6/1997 | Kugel |
| 5,637,113 A | 6/1997 | Tartaglia et al. |
| 5,641,767 A | 6/1997 | Wess et al. |
| 5,700,848 A | 6/1997 | Soon-Shiong |
| 5,665,115 A | 9/1997 | Cragg |
| 5,693,014 A | 12/1997 | Abele et al. |
| 5,695,525 A | 12/1997 | Mulhauser et al. |
| 5,700,286 A | 12/1997 | Tartaglia et al. |
| 5,705,485 A | 1/1998 | Cini et al. |
| 5,731,346 A | 3/1998 | Egberg et al. |
| 5,736,152 A | 4/1998 | Dunn |
| 5,738,869 A | 4/1998 | Fischer et al. |
| 5,747,533 A | 5/1998 | Egberg et al. |
| 5,749,845 A | 5/1998 | Hildebrand et al. |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,789,465 A | 8/1998 | Harvey et al. |
| 5,800,392 A | 9/1998 | Racchini |
| 5,807,306 A | 9/1998 | Shapland et al. |
| 5,817,343 A | 10/1998 | Burke |
| 5,824,082 A | 10/1998 | Brown |
| 5,827,325 A | 10/1998 | Landgrebe et al. |
| 5,828,785 A | 10/1998 | Kitsuki et al. |
| 5,837,313 A | 11/1998 | Ding et al. |
| 5,843,172 A | 12/1998 | Yan |
| 5,843,919 A | 12/1998 | Burger |
| 5,865,787 A | 2/1999 | Shapland et al. |
| 5,874,470 A | 2/1999 | Nehne et al. |
| 5,879,359 A | 3/1999 | Dorigatti et al. |
| 5,897,911 A | 4/1999 | Loeffler |
| 5,898,040 A | 4/1999 | Shalaby et al. |
| 5,902,266 A | 5/1999 | Leone et al. |
| 5,906,831 A | 5/1999 | Larsson et al. |
| 5,931,165 A | 8/1999 | Reich et al. |
| 5,947,977 A | 9/1999 | Slepian et al. |
| 5,954,767 A | 9/1999 | Pajotin et al. |
| 5,955,502 A | 9/1999 | Hansen et al. |
| 5,986,043 A | 11/1999 | Hubbell et al. |
| 6,004,549 A | 12/1999 | Reichert et al. |
| 6,005,004 A | 12/1999 | Katz et al. |
| 6,010,480 A | 1/2000 | Abele et al. |
| 6,010,766 A | 1/2000 | Braun et al. |
| 6,010,776 A | 1/2000 | Exsted et al. |
| 6,013,055 A | 1/2000 | Bampos et al. |
| 6,015,844 A | 1/2000 | Harvey et al. |
| 6,028,164 A | 2/2000 | Loomis |
| 6,033,380 A | 3/2000 | Butaric et al. |
| 6,033,436 A | 3/2000 | Steinke et al. |
| 6,040,330 A | 3/2000 | Hausheer et al. |
| 6,048,332 A | 4/2000 | Duffy et al. |
| 6,048,725 A | 4/2000 | Shimada et al. |
| 6,056,970 A | 5/2000 | Greenawalt et al. |
| 6,066,777 A | 5/2000 | Benchetrit |
| 6,075,180 A | 6/2000 | Sharber et al. |
| 6,077,698 A | 6/2000 | Swan et al. |
| 6,080,442 A | 6/2000 | Yoshikawa et al. |
| 6,083,950 A | 7/2000 | Anand et al. |
| 6,090,809 A | 7/2000 | Anand et al. |

(56) References Cited

U.S. PATENT DOCUMENTS

| | | |
|---|---|---|
| 6,093,792 A | 7/2000 | Gross et al. |
| 6,117,911 A | 9/2000 | Grainger et al. |
| 6,120,477 A | 9/2000 | Campbell et al. |
| 6,120,539 A | 9/2000 | Eldridge et al. |
| 6,120,789 A | 9/2000 | Dunn |
| 6,132,765 A | 10/2000 | DiCosmo et al. |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,200,985 B1 | 3/2001 | Cottens et al. |
| 6,203,551 B1 | 3/2001 | Wu |
| 6,206,916 B1 | 3/2001 | Furst |
| 6,211,315 B1 | 4/2001 | Larock et al. |
| 6,224,579 B1 | 5/2001 | Modak et al. |
| 6,224,909 B1 | 5/2001 | Opitz et al. |
| 6,228,383 B1 | 5/2001 | Hansen et al. |
| 6,229,032 B1 | 5/2001 | Jacobs et al. |
| 6,231,600 B1 | 5/2001 | Zhong |
| 6,245,366 B1 | 6/2001 | Popplewell et al. |
| 6,245,811 B1 | 6/2001 | Harrobin et al. |
| 6,258,124 B1 | 6/2001 | Darois et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,287,285 B1 | 9/2001 | Michal et al. |
| 6,287,316 B1 | 9/2001 | Agarwal |
| 6,299,604 B1 | 10/2001 | Ragheb et al. |
| 6,306,438 B1 | 10/2001 | Oshlack et al. |
| 6,326,072 B1 | 12/2001 | Ojeda et al. |
| 6,326,360 B1 | 12/2001 | Kanazawa et al. |
| 6,331,568 B1 | 12/2001 | Horrobin |
| 6,342,254 B1 | 1/2002 | Soudant et al. |
| 6,346,110 B2 | 2/2002 | Wu |
| 6,355,063 B1 | 3/2002 | Calcote |
| 6,358,556 B1 | 3/2002 | Ding et al. |
| 6,364,856 B1 | 4/2002 | Ding et al. |
| 6,364,893 B1 | 4/2002 | Sahatjian et al. |
| 6,364,903 B2 | 4/2002 | Tseng et al. |
| 6,368,541 B1 | 4/2002 | Pajotin et al. |
| 6,368,658 B1 | 4/2002 | Schwarz et al. |
| 6,369,039 B1 | 4/2002 | Palasis et al. |
| 6,387,301 B1 | 5/2002 | Nakajima et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,463,323 B1 | 10/2002 | Conrad-Vlasak et al. |
| 6,465,525 B1 | 10/2002 | Guire et al. |
| 6,471,980 B2 | 10/2002 | Sirhan et al. |
| 6,479,683 B1 | 11/2002 | Abney et al. |
| 6,485,752 B1 | 11/2002 | Rein et al. |
| 6,491,938 B2 | 12/2002 | Kunz |
| 6,500,174 B1 | 12/2002 | Maguire |
| 6,500,453 B2 | 12/2002 | Brey et al. |
| 6,503,556 B2 | 1/2003 | Harish et al. |
| 6,506,410 B1 | 1/2003 | Park et al. |
| 6,525,145 B2 | 2/2003 | Gavaert et al. |
| 6,527,801 B1 | 3/2003 | Dutta |
| 6,534,693 B2 | 3/2003 | Fischell et al. |
| 6,541,116 B2 | 4/2003 | Michal et al. |
| 6,544,223 B1 | 4/2003 | Kokish |
| 6,544,224 B1 | 4/2003 | Steese-Bradley |
| 6,548,081 B2 | 4/2003 | Sadozai et al. |
| 6,565,659 B1 | 5/2003 | Pacetti et al. |
| 6,569,441 B2 | 5/2003 | Kunz et al. |
| 6,579,851 B2 | 6/2003 | Goke et al. |
| 6,596,002 B2 | 7/2003 | Therin et al. |
| 6,599,323 B2 | 7/2003 | Melican et al. |
| 6,610,006 B1 | 8/2003 | Amid et al. |
| 6,610,035 B2 | 8/2003 | Yang et al. |
| 6,610,068 B1 | 8/2003 | Yang et al. |
| 6,616,650 B1 | 9/2003 | Rowe |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim |
| 6,663,880 B1 | 12/2003 | Roorda et al. |
| 6,669,735 B1 | 12/2003 | Pelissier |
| 6,670,355 B2 | 12/2003 | Azrolan et al. |
| 6,677,342 B2 | 1/2004 | Wolff et al. |
| 6,677,386 B1 | 1/2004 | Giezen et al. |
| 6,685,956 B2 | 2/2004 | Chu et al. |
| 6,689,388 B2 | 2/2004 | Kuhrts |
| 6,696,583 B2 | 2/2004 | Koncar et al. |
| 6,723,133 B1 | 4/2004 | Pajotin |
| 6,730,016 B1 | 5/2004 | Cox et al. |
| 6,730,064 B2 | 5/2004 | Ragheb et al. |
| 6,740,122 B1 | 5/2004 | Pajotin |
| 6,753,071 B1 | 6/2004 | Pacetti |
| 6,758,847 B2 | 7/2004 | Maguire |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,808,536 B2 | 10/2004 | Wright et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,902,522 B1 | 6/2005 | Walsh et al. |
| 6,918,927 B2 | 7/2005 | Bates et al. |
| 6,996,952 B2 | 2/2006 | Gupta et al. |
| 7,070,858 B2 | 4/2006 | Shalaby et al. |
| 7,090,655 B2 | 8/2006 | Barry |
| 7,101,381 B2 | 9/2006 | Ford et al. |
| 7,112,209 B2 | 9/2006 | Ramshaw et al. |
| 7,135,164 B2 | 11/2006 | Rojanapanthu et al. |
| 7,152,611 B2 | 12/2006 | Brown et al. |
| 7,311,980 B1 | 12/2007 | Hossainy et al. |
| 7,323,178 B1 | 1/2008 | Zhang et al. |
| 7,323,189 B2 | 1/2008 | Pathak |
| 7,415,811 B2 | 8/2008 | Gottlieb |
| 7,691,946 B2 | 4/2010 | Liu et al. |
| 7,854,958 B2 | 12/2010 | Kramer |
| 7,947,015 B2 | 5/2011 | Herweck et al. |
| 8,001,922 B2 | 8/2011 | Labrecque et al. |
| 8,021,331 B2 | 9/2011 | Herweck et al. |
| 8,124,127 B2 | 2/2012 | Faucher et al. |
| 8,263,102 B2 | 9/2012 | Labrecque et al. |
| 8,298,290 B2 | 10/2012 | Pelissier et al. |
| 8,308,684 B2 | 11/2012 | Herweck et al. |
| 8,312,836 B2 | 11/2012 | Corbeil et al. |
| 8,367,099 B2 | 2/2013 | Herweck et al. |
| 8,461,129 B2 | 6/2013 | Bolduc et al. |
| 8,501,229 B2 | 8/2013 | Faucher et al. |
| 8,722,077 B2 | 5/2014 | Labrecque et al. |
| 8,772,077 B2 | 7/2014 | Lee et al. |
| 8,795,703 B2 | 8/2014 | Swanick et al. |
| 8,858,978 B2 | 10/2014 | Labrecque et al. |
| 8,888,887 B2 | 11/2014 | Hargrove et al. |
| 9,000,040 B2 | 4/2015 | Faucher et al. |
| 9,012,506 B2 | 4/2015 | Faucher et al. |
| 8,962,023 B2 | 5/2015 | Labrecque et al. |
| 9,220,820 B2 | 12/2015 | Faucher et al. |
| 9,278,161 B2 | 3/2016 | Swanick et al. |
| 9,427,423 B2 | 8/2016 | Swanick et al. |
| 9,493,636 B2 | 11/2016 | Ah et al. |
| 9,682,175 B2 | 6/2017 | Labrecque et al. |
| 9,801,913 B2 | 10/2017 | Ferraro et al. |
| 10,016,465 B2 | 7/2018 | Labrecque et al. |
| 10,864,304 B2 | 12/2020 | Faucher et al. |
| 2001/0022988 A1 | 9/2001 | Schwarz et al. |
| 2001/0025034 A1 | 9/2001 | Arbiser |
| 2001/0025196 A1 | 9/2001 | Chinn et al. |
| 2001/0026803 A1 | 10/2001 | Febbe et al. |
| 2001/0027299 A1 | 10/2001 | Yang et al. |
| 2001/0051595 A1 | 12/2001 | Lyons et al. |
| 2002/0002154 A1 | 1/2002 | Guivarch et al. |

(56) References Cited

U.S. PATENT DOCUMENTS

| | | |
|---|---|---|
| 2002/0007209 A1 | 1/2002 | Scheerder et al. |
| 2002/0012741 A1 | 1/2002 | Heinz et al. |
| 2002/0013590 A1 | 1/2002 | Therin et al. |
| 2002/0015970 A1 | 2/2002 | Murray et al. |
| 2002/0022052 A1 | 2/2002 | Dransfield |
| 2002/0026899 A1 | 3/2002 | McLaughlin et al. |
| 2002/0026900 A1 | 3/2002 | Huang et al. |
| 2002/0032414 A1 | 3/2002 | Ragheb et al. |
| 2002/0055701 A1 | 5/2002 | Fischell et al. |
| 2002/0077652 A1 | 6/2002 | Kieturakis et al. |
| 2002/0082679 A1 | 6/2002 | Sirhan et al. |
| 2002/0098278 A1 | 7/2002 | Bates et al. |
| 2002/0103494 A1 | 8/2002 | Pacey |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0127327 A1 | 9/2002 | Schwarz et al. |
| 2002/0142089 A1 | 10/2002 | Koike et al. |
| 2002/0183716 A1 | 12/2002 | Herweck et al. |
| 2002/0192352 A1 | 12/2002 | Jamshed |
| 2002/0193829 A1 | 12/2002 | Kennedy et al. |
| 2003/0003125 A1 | 1/2003 | Nathan et al. |
| 2003/0003221 A1 | 1/2003 | Zhong et al. |
| 2003/0004564 A1 | 1/2003 | Elkins et al. |
| 2003/0009213 A1 | 1/2003 | Yang |
| 2003/0033004 A1 | 2/2003 | Ishii |
| 2003/0036803 A1 | 2/2003 | McGhan et al. |
| 2003/0055403 A1 | 3/2003 | Nestenborg et al. |
| 2003/0065292 A1 | 4/2003 | Darouiche et al. |
| 2003/0065345 A1 | 4/2003 | Weadock |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0100955 A1 | 5/2003 | Greenawalt et al. |
| 2003/0108588 A1 | 6/2003 | Chen et al. |
| 2003/0130206 A1 | 6/2003 | Koziak et al. |
| 2003/0124087 A1 | 7/2003 | Kim et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0181988 A1 | 9/2003 | Rousseau |
| 2003/0187516 A1 | 10/2003 | Amid et al. |
| 2003/0191179 A1 | 10/2003 | Joshi-Hangai et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2003/0211230 A1 | 11/2003 | Pacetti et al. |
| 2003/0212462 A1 | 11/2003 | Gryska et al. |
| 2003/0220297 A1 | 11/2003 | Berstein et al. |
| 2004/0006296 A1 | 1/2004 | Fischell et al. |
| 2004/0013704 A1 | 1/2004 | Kabra et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0058008 A1 | 3/2004 | Tarcha et al. |
| 2004/0060260 A1 | 4/2004 | Gottlieb et al. |
| 2004/0071756 A1 | 4/2004 | Fischell et al. |
| 2004/0072849 A1 | 4/2004 | Schreiber et al. |
| 2004/0073284 A1 | 4/2004 | Bates et al. |
| 2004/0092969 A1 | 5/2004 | Kumar |
| 2004/0102758 A1 | 5/2004 | Davila et al. |
| 2004/0117007 A1 | 6/2004 | Whitbourne et al. |
| 2004/0123877 A1 | 7/2004 | Brown et al. |
| 2004/0131755 A1 | 7/2004 | Zhong et al. |
| 2004/0133275 A1 | 7/2004 | Manamann |
| 2004/0137066 A1 | 7/2004 | Swaminathan |
| 2004/0142094 A1 | 7/2004 | Narayanan |
| 2004/0146546 A1 | 7/2004 | Gravett et al. |
| 2004/0153125 A1 | 8/2004 | Roby |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0137179 A1 | 10/2004 | Shojiro et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0236278 A1 | 11/2004 | Herweck et al. |
| 2004/0241211 A9 | 12/2004 | Fischell |
| 2004/0256264 A1 | 12/2004 | Israelsson et al. |
| 2005/0010078 A1 | 1/2005 | Jamiolkowski et al. |
| 2005/0025804 A1 | 2/2005 | Heller |
| 2005/0042251 A1 | 2/2005 | Zhang et al. |
| 2005/0084514 A1 | 4/2005 | Shebuski et al. |
| 2005/0095267 A1 | 5/2005 | Campbell et al. |
| 2005/0100655 A1 | 5/2005 | Zhong et al. |
| 2005/0101522 A1 | 5/2005 | Speck et al. |
| 2005/0106206 A1 | 5/2005 | Herweck et al. |
| 2005/0106209 A1 | 5/2005 | Ameri et al. |
| 2005/0112170 A1 | 5/2005 | Hossainy et al. |
| 2005/0113687 A1 | 5/2005 | Herweck et al. |
| 2005/0113849 A1 | 5/2005 | Popdiuk et al. |
| 2005/0124062 A1 | 6/2005 | Subirade |
| 2005/0129787 A1 | 6/2005 | Murad |
| 2005/0154416 A1 | 7/2005 | Herweck et al. |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0181061 A1 | 8/2005 | Roderick et al. |
| 2005/0182485 A1 | 8/2005 | Falotico et al. |
| 2005/0186244 A1 | 8/2005 | Hunter et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0223679 A1 | 10/2005 | Gottlieb et al. |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0020031 A1 | 1/2006 | Berlin |
| 2006/0030669 A1 | 2/2006 | Faton et al. |
| 2006/0036311 A1 | 2/2006 | Nakayama et al. |
| 2006/0112536 A1 | 2/2006 | Herweck et al. |
| 2006/0051544 A1 | 3/2006 | Goldmann |
| 2006/0058737 A1 | 3/2006 | Herweck et al. |
| 2006/0058881 A1 | 3/2006 | Trieu |
| 2006/0064175 A1 | 3/2006 | Pelissier et al. |
| 2006/0067974 A1 | 3/2006 | Labrecque et al. |
| 2006/0067975 A1 | 3/2006 | Labrecque et al. |
| 2006/0067976 A1* | 3/2006 | Ferraro ............... A61K 31/225 427/2.26 |
| 2006/0067977 A1 | 3/2006 | Labrecque et al. |
| 2006/0067983 A1 | 3/2006 | Swanick et al. |
| 2006/0068672 A1 | 3/2006 | Dixit et al. |
| 2006/0078586 A1 | 4/2006 | Ferraro et al. |
| 2006/0083768 A1 | 4/2006 | Labrecque et al. |
| 2006/0088596 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0188607 A1 | 8/2006 | Schramm et al. |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0263330 A1 | 11/2006 | Emeta et al. |
| 2006/0269485 A1 | 11/2006 | Friedman et al. |
| 2006/0246105 A1 | 12/2006 | Molz et al. |
| 2007/0003603 A1 | 1/2007 | Karandikar |
| 2007/0015893 A1 | 1/2007 | Hakuta et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |

(56) References Cited

U.S. PATENT DOCUMENTS

| | | |
|---|---|---|
| 2007/0141112 A1 | 6/2007 | Falotico et al. |
| 2007/0198040 A1 | 8/2007 | Buevich et al. |
| 2007/0202149 A1 | 8/2007 | Faucher |
| 2007/0212411 A1 | 9/2007 | Fawzy et al. |
| 2007/0218182 A1 | 9/2007 | Schneider et al. |
| 2007/0238697 A1 | 10/2007 | Jackson et al. |
| 2007/0264460 A1 | 11/2007 | Del Tredici |
| 2007/0275074 A1 | 11/2007 | Holm et al. |
| 2007/0276487 A1 | 11/2007 | Carteron et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0016037 A1 | 1/2008 | Enomoto et al. |
| 2008/0038307 A1 | 2/2008 | Hoffmann |
| 2008/0044481 A1 | 2/2008 | Harel |
| 2008/0045557 A1 | 2/2008 | Grainger et al. |
| 2008/0071385 A1 | 3/2008 | Binette et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0160307 A1 | 7/2008 | Bauchet |
| 2008/0206305 A1 | 8/2008 | Herweck et al. |
| 2008/0207756 A1 | 8/2008 | Herweck et al. |
| 2008/0279929 A1 | 11/2008 | Devane et al. |
| 2008/0286440 A1 | 11/2008 | Scheer |
| 2008/0289300 A1 | 11/2008 | Gottlieb et al. |
| 2009/0011116 A1 | 1/2009 | Herweck et al. |
| 2009/0036996 A1 | 2/2009 | Roeber |
| 2009/0047414 A1 | 2/2009 | Corbeil et al. |
| 2009/0082864 A1 | 3/2009 | Chen |
| 2009/0092665 A1 | 4/2009 | Mitra et al. |
| 2009/0099651 A1 | 4/2009 | Hakimi-Mehr et al. |
| 2009/0181074 A1 | 7/2009 | Makower |
| 2009/0181937 A1 | 7/2009 | Faucher et al. |
| 2009/0186081 A1 | 7/2009 | Holm et al. |
| 2009/0208552 A1 | 8/2009 | Faucher et al. |
| 2009/0226601 A1 | 9/2009 | Zhong et al. |
| 2009/0240288 A1 | 9/2009 | Guetty |
| 2009/0259235 A1 | 10/2009 | Doucet et al. |
| 2009/0270999 A1 | 10/2009 | Brown |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2010/0318108 A1 | 12/2010 | Datta et al. |
| 2011/0028412 A1 | 2/2011 | Cappello et al. |
| 2011/0045050 A1 | 2/2011 | Elbayoumi et al. |
| 2011/0144667 A1 | 6/2011 | Horton et al. |
| 2011/0213302 A1 | 9/2011 | Herweck et al. |
| 2011/0274823 A1 | 11/2011 | Labrecque et al. |
| 2012/0016038 A1 | 1/2012 | Faucher et al. |
| 2012/0213839 A1 | 8/2012 | Faucher et al. |
| 2012/0259348 A1 | 10/2012 | Paul |
| 2012/0315219 A1 | 12/2012 | Labrecque et al. |
| 2013/0041004 A1 | 2/2013 | Drager et al. |
| 2013/0084243 A1 | 4/2013 | Goetsch et al. |
| 2013/0096073 A1 | 4/2013 | Sidelman |

FOREIGN PATENT DOCUMENTS

| | | |
|---|---|---|
| CN | 101448474 | 6/2009 |
| CN | 102256565 | 11/2011 |
| DE | 19916086 | 10/1999 |
| DE | 10115740 | 10/2002 |
| EP | 0471566 A1 | 2/1992 |
| EP | 610731 A1 | 8/1994 |
| EP | 0623354 | 11/1994 |
| EP | 0730864 | 9/1996 |
| EP | 0790822 | 8/1997 |
| EP | 0655222 | 6/1998 |
| EP | 0873133 | 10/1998 |
| EP | 0917561 | 5/1999 |
| EP | 0950386 | 10/1999 |
| EP | 1132058 | 9/2001 |
| EP | 1140243 | 10/2001 |
| EP | 1181943 | 2/2002 |
| EP | 219265 | 1/2003 |
| EP | 1270024 | 1/2003 |
| EP | 1273314 | 1/2003 |
| EP | 1364628 | 11/2003 |
| EP | 1402906 A1 | 3/2004 |
| EP | 1520795 | 4/2005 |
| EP | 1557183 | 7/2005 |
| EP | 1576970 | 9/2005 |
| EP | 1718347 | 11/2006 |
| EP | 1952807 A1 | 8/2008 |
| EP | 2083875 A2 | 8/2009 |
| EP | 2201965 | 6/2010 |
| EP | 2083875 | 3/2013 |
| GB | 2363572 | 1/2002 |
| JP | 4950124 | 5/1974 |
| JP | 61291520 | 12/1986 |
| JP | 1175864 | 7/1989 |
| JP | 1503296 | 9/1989 |
| JP | 8224297 | 9/1996 |
| JP | 200110958 | 1/2001 |
| JP | 2006512140 | 4/2006 |
| JP | 2012505025 | 3/2012 |
| JP | 2012505030 | 3/2012 |
| JP | 2013508033 | 3/2013 |
| KR | 20080025986 | 3/2008 |
| RU | 2125887 | 2/1999 |
| SU | 1297865 | 3/1987 |
| WO | 86000912 | 2/1986 |
| WO | 8706463 | 11/1987 |
| WO | 1990/001969 | 3/1990 |
| WO | 1990008544 | 8/1990 |
| WO | 9321912 | 11/1993 |
| WO | 9517901 | 7/1995 |
| WO | 1995/026715 | 10/1995 |
| WO | 9618417 | 6/1996 |
| WO | 1996041588 | 12/1996 |
| WO | 1997/002042 | 1/1997 |
| WO | 1997/013528 | 3/1997 |
| WO | 1997/013528 | 4/1997 |
| WO | 9823228 | 6/1998 |
| WO | 1998/030206 | 7/1998 |
| WO | 9846287 A2 | 10/1998 |
| WO | 1998/054275 | 12/1998 |
| WO | 9908544 | 2/1999 |
| WO | 1999/025336 | 5/1999 |
| WO | 9927989 | 6/1999 |
| WO | 9940874 | 8/1999 |
| WO | 199956664 | 11/1999 |
| WO | 0012147 | 3/2000 |
| WO | 0040236 | 7/2000 |
| WO | 200440278 | 7/2000 |
| WO | 0053212 | 9/2000 |
| WO | 2000062830 | 10/2000 |
| WO | 0115746 | 3/2001 |
| WO | 2001/024866 | 4/2001 |
| WO | 2001/026585 | 4/2001 |
| WO | 2001/037808 | 5/2001 |
| WO | 0145763 | 6/2001 |
| WO | 2001/060586 | 8/2001 |
| WO | 2001/066036 | 9/2001 |
| WO | 2001/076649 | 10/2001 |
| WO | 200108560 | 11/2001 |
| WO | 0222199 | 3/2002 |
| WO | 200222047 | 3/2002 |
| WO | 2002/049535 | 6/2002 |
| WO | 02076509 | 10/2002 |
| WO | 2002100455 | 12/2002 |
| WO | 2003000308 | 1/2003 |
| WO | 2003/015748 | 2/2003 |
| WO | 2003/028622 | 4/2003 |
| WO | 2003/037397 | 5/2003 |
| WO | 2003/037398 | 5/2003 |
| WO | 2003/041756 | 5/2003 |
| WO | 03039612 A1 | 5/2003 |
| WO | 2003039612 | 5/2003 |
| WO | 2003/070125 | 8/2003 |
| WO | 2003073960 | 9/2003 |
| WO | 2003/092741 | 11/2003 |

(56) References Cited

FOREIGN PATENT DOCUMENTS

| | | |
|---|---|---|
| WO | 2003/092779 | 11/2003 |
| WO | 2003094787 | 11/2003 |
| WO | 2003105727 | 12/2003 |
| WO | 2004/004598 | 1/2004 |
| WO | 2004/006976 | 1/2004 |
| WO | 2004/006978 | 1/2004 |
| WO | 2004/028583 | 4/2004 |
| WO | 04028610 | 4/2004 |
| WO | 2004028582 | 4/2004 |
| WO | 04091684 | 10/2004 |
| WO | 2004101010 A1 | 11/2004 |
| WO | 2005/000165 | 1/2005 |
| WO | 2005/016400 | 2/2005 |
| WO | 2005/053767 | 6/2005 |
| WO | 2005/073091 | 8/2005 |
| WO | 2005082434 A2 | 9/2005 |
| WO | 2005116118 | 12/2005 |
| WO | 2006/024488 | 3/2006 |
| WO | 2006/036967 | 4/2006 |
| WO | 2006032812 | 6/2006 |
| WO | 2006/102374 | 9/2006 |
| WO | 2007047028 | 4/2007 |
| WO | 2007047781 | 4/2007 |
| WO | 2008010788 | 1/2008 |
| WO | 2008016664 | 2/2008 |
| WO | 2008039308 | 4/2008 |
| WO | 08057328 A2 | 5/2008 |
| WO | 2009091900 | 7/2009 |
| WO | 2010042134 | 4/2010 |
| WO | 2010042241 | 4/2010 |
| WO | 2012009707 | 1/2012 |

OTHER PUBLICATIONS

Wanasundara et al., "Effect of processing on constituents and oxidative stability of marine oils," Journal of Food Lipids, 1998, vol. 5, pp. 29-41.
Supplementary European Search Report for Application No. 05 80 2894, dated Jul. 27, 2011.
Supplementary European Search Report for Application No. 05 800 844, dated Aug. 19, 2011.
International Preliminary Report on Patentability for Application No. PCT/US08/71565, dated Apr. 5, 2010.
Supplementary European Search Report for EP Application No. 08782511, dated Apr. 23, 2013.
Advisory Action of U.S. Appl. No. 11/238,554, dated Jul. 10, 2009.
Notice of Allowance of U.S. Appl. No. 11/238,554, dated Apr. 28, 2011.
Non-Final Office Action of U.S. Appl. No. 13/185,135, dated Jan. 25, 2013.
Non-Final Office Action of U.S. Appl. No. 12/182,165, dated Jun. 24, 2013.
Sweetman, Sean C., "Martindale: The complete drug reference," 33rd ed., 2002, Pharmaceutical Press, pp. 1-90.
Drugs.com "Drug Index A to Z," retrieved on Apr. 1, 2013, pp. 1-4.
Garner, Brian A., "A Dictionary of Modern Legal Usage," 2nd ed., 1987, pp. 389-390 and 713-717.
Pearlman, Daniel D. & Paul R., "Guide to Rapid Revision," 3rd ed., 1982, Bobbs-Merrill Educational Publishing, pp. 25-27.
Canter, Sheryl, "Chemistry of Cast Iron Seasoning: A Science-Based How-To," retrieved from sherylcanter.com on Apr. 5, 2013, pp. 1-5.
O'Neil, Maryadelle J. et al., The Merck Index—An Encyclopedia of Chemicals, Drugs, and Biologicals, 14th ed., 2006, entries for "Calcium Carbonate", "Cyclosporins", "Prussian Blue", and "Rapamycin", pp. 1-12.
EP Office Action for EP Application No. 07838216.5, dated Feb. 11, 2010.
Kugel, et al., "Minimally invasive, Nonlaparoscopic, Preperitoneal, and Sutureless, Inguinal Herniorraphy," The American Journal of Surgery, 1999, vol. 178, pp. 298-302.

Lightenstein, et al., "Repair of Recurrent Ventral Hernias by an Internal Binder," The American Journal of Surgery, 1976, vol. 132, pp. 121-125.
Moreno-Egea, "Laparoscopic repair of Ventral and Incisional Hernias Using a new Composite Mesh (Parletex)," Surgical Laparoscopy, Endoscopy & Percutaneous Techniques, 2001, vol. 11, No. 2, pp. 103-106.
"Sharper Curve, Stronger Egg", Inside Science, printed Jan. 21, 2016, http://www.insidescience.org/content/sharper-curve-stronger-egg/779, 6 pages.
Moreno et al., J. Agric. Food Chem., 2003, vol. 51, pp. 2216-2221.
DRC Handbook of Chemistry and Physics, 89th Edition, 2008-2009, Composition and Properties of Common Oils and Fats, pp. 7-9 to 7-13.
Ali, Handbook of Industrial Chemistry: Organic Chemicals, Chapter 4, Edible Fats, Oils and Waxes, 1994, pp. 85-121.
Rietjens et al., "The pro-oxidant chemistry of the natural antioxidants vitamin C, vitamin E, carotenoids, and flavonids," Environmental Toxicology and Pharmacology, 2002, vol. 11, pp. 321-333.
European Communication for Application No. 07112611.4-2107, dated Nov. 30, 2007.
Clauss, Wolfram et al., "No. Difference Among Modern Contrast Media's Effect on Neointimal Proliferation and Restenosis After Coronary Stenting in Pigs," Investigative Reporting; 2004.
Nagao et al., "Conjugated Fatty Acids in Food and Their Health Benefits," 2005, The Society for Biotechnology, Japan, Journal of Bioscience and Bioengineering, vol. 100, No. 2, pp. 152-157.
Goodnight et al., "Polyunsaturated Fatty Acids, Hyperlipidemia, and Thrombosis," 1982, American Heart Association, Journal of the American Heart Association, vol. 2, No. 2, pp. 87-113.
Bard FDA 510K Approval (Jan. 2001).
Bard Internet Publication (Apr. 2001).
Bard FDA 510K Approval (Jul. 2002).
Bellon et al., "Evaluation of a New Composite Prosthesis (PL-PU99) for the Repair of Abdominal Wall Defects in Terms of Behavioral the Peritoneal Interface," World Journal of Surgery, 26: 661-666 (2002).
Bendavid et al., "A Femoral 'Umbrella' for Femoral Hemial Repair Surgery," Gynecology and Obstetrics, 165: 153-156(1987).
Bendavid et al., "New Techniques in Hernia Repair," World Journal of Surgery, 13: 522-531 (1989).
Greenawalt et al., "Evaluation of Sepramesh Biosurgical Composite in a Rabbit Hernia Repair Model," Journal of Surgical Research, 94: 92-98 (2000).
Helfrich et al., "Abdominal Wall Hernia Repair: Use of the Gianturco-Helfrich-Eberhach Hernia Mesh," Journal of Laparoendoscopic Surgery, 5(2): 91-96 (1995).
Hydrogenated Castor Oil, at http://www.acme-hardesty.com/product/hydrogenated-castor-oil/ (downloaded Jun. 2, 2017), which corresponds to "Exhibit B1."
Hawley's Condensed Chemical Dictionary—pp. 425 and 426 (2001), which corresponds to "Exhibit A1."
Hoefler, Andrew C., "Sodium Carboxymethyl Cellulose: Chemistry, Functionality, and Applications", Hercules Incorporated, http://www.herc.com/foodgums/index.htm, 15 pages.
Hercules Inc./Aqualon Div. CMC Quality Specifiction, Oct. 19, 2001 (Revised Sep. 2, 2008), 1 page.
Aqualon: Sodium Carboxymethylcellulose: Physical and Chemical Properties, Hercules Incorporated, 1999, 30 pages.
Fei, Bin, et al., "Hydrogel of Biodegradable Cellulose Derivatives. I. Radiation-Induced Crosslinking of CMC", Journal of Applied Polymer Science, 2000, vol. 78, pp. 278-283.
Shakhashiri, Chemical of the week Fats and Oils, at www.scifun.org (last revised Jan. 30, 2008) 2 pages.
"What are hydrogenated fats?" at http://www.whfoods.com/genpage.php?tname=george&dbid=10 (downloaded Dec. 19, 2017), 3 pages.
Sigma reference 2007.
Salvolainen et al. International Journal of Pharmaceutics 2002 244:151-161.
Nair et al. Journal of Dairy Science 2005 88:3488-3495.
Nakatsuji et al. Journal of Investigative Dermatology 2009 129(10): 2480-2488.

(56) References Cited

OTHER PUBLICATIONS

Gervajio "Fatty Acids and Derivatives from Coconut Oil." Baileys Industrial Oil and Fat Products, Sixth Edition. Ed. Sahahdi. Hoboken: John Wiley & Sons, Inc. 2005 1-3.
Pandey et al. Tuberculosis 2005 85:227-234.
Hogg, Ronald J., et al.. Clinical Trial to Evaluate Omega-3 Fatty Acids and Alternate Day Prednisone in Patients with IgA Nephropathy: Report from the Southwest Pediatric Nephrology Study Group, Clinical Journal of the American Society of Nephrology, 2006, 467-474, 1.
Mateo, R.D., et al., Effect of dietary supplementation of n-3 fatty acids and elevated concentrations of dietary protein an the performance of sows, J. Anim. Sci., 2009, 948-959, 87.
Petrovic, Z. S., Polymers from biological oils, Contemporary Materials, I-1, 2010, 39-50.
Sahni, Vasav, et al., A Review on Spider Silk Adhesion, The Journal of Adhesion, 2011, 595-614, 87.
Genzyme Corporation, 510(k) Notification, Section 10: 510(k) Summary, Dec. 21, 1999, 11 pages.
Deeken, Corey R., et al., A review of the composition, characteristics, and effectiveness of barrier mesh prostheses utilized for laparoscopic ventral hernia repair, Surg Endosc, 2011, 10 pages.
"What are Omega-9 Fats?", Paleo Leap, LLC, printed from http://paleoleap.com/omega-9-fats on Sep. 14, 2016, 5 pages.
Kumar, Ashavani, et al., "Silver-nanoparticle-embedded antimicrobial paints based on vegetable oil", Nature Materials, vol. 7, Mar. 2008, pp. 236-241.
Ralph L. Shriner et al., "The Systematic Identification of Organic Compounds—a laboratory manual", pp. 284 and 285, 6th ed. (John Wiley & Sons—1980).
Olive Oil Reference Book (PerkinElmer, Inc. 2012), pp. 1-48.
Standard for Olive Oils and Olive Pomace Oils, Codex Stan 33-1981 (World Health Organization 2013), pp. 1-9.
Wei Wang et al., "Directing Oleate Stabilized Nanosized Silver Colloids into Organic Phases", LANGMUIR, vol. 14, No. 3, (1998), pp. 602-610.
Bechert et al., "A New Method for Screening Anti-Infective Biomaterials", Nature Medicine. 6(8):1053-1056(2000).
Cheong et al., "Peritoneal healing and adhesion formation/reformation", Human Reproduction Update. 7(6):556-566(2001).
Carbonell et al., "The susceptibility of prosthetic biomaterials to infection", Surgical Endoscopy. 19:430-435(2005) (abstract).
Kuijer et al., "Assessing infection risk in implanted tissue-engineered devices", Biomaterials. 28:5148-5154(2007).
Arciola et al., "Strong biofilm production, antibiotic multi-resistance and high gelE expression in epidemic clones of Enterococcus faecalis from orthopaedic implant infections", Biomaterials. 29:580-586(2008) (abstract).
Zheng et al., "Fatty acid synthesis is a target for antibacterial activity of unsaturated fatty acids", FEBS Letters, Elsevier, Amsterdam, NL, vol. 579, No. 23, Sep. 26, 2005, pp. 5157-5162.
Lee, Ji-Young et al., "Antimicrobial Synergistic Effect of Linolenic Acid and Monoglyceride against *Bacillus cereus* and *Staphylococcus aureus*", Journal of Agricultural and Food Chemistry, vol. 50, No. 7, Mar. 1, 2002, pp. 2193-2199.
Larsen, D. et al., "Effect of cooking method on the fatty acid profile of New Zealand King Salmon (Oncorhynchus shawytscha)" Food Chemistry 119 (2010) 785-790 (Year: 2010).
Steiner, M. et al. "Effect of Local Processing Methods (Cooking, Frying and Smoking) on Three Fish Species from Ghana: Part I. Proximate Composition, Fatty Acids, Minerals, Trace Elements and Vitamins" Food Chemistry 40 (1991) 309-321 (Year: 1991).
Gruger, Jr. E.H. Fatty Acid Composition. NMFS Scientific Publications by BOFC Fisheries, (http://spo.nmfs.noaa.gov/Circulars/CIRC276.pdf) 1967, pp. 1-30 (Year: 1967).
"Scientific Opinion on Fish Oil for Human consumption. Food Hygiene, including Rancidity", EFSA Journal—pp. 1-48, vol. 8, (2010).
"Gas Chromatography Theory"—updated Apr. 1, 2016—http://www.chem.ucia.edu/%7Ebacher/General/30BL/gc/theory.html.
Steven J. Lehotay et al., "Application of Gas Chromatography in Food Analysis", Trends in Analytical Chemistry—pp. 686-697, vol. 21, (2002).
Edible Oils. (http://www.chempro.in/fattyacid.htm) accessed Apr. 14, 2014.
Malayoglu et al. "Dietary vitamin E ($\alpha$-tocopheryl acetate) and organic selenium supplementation: performance and antioxidant status of broilers fed n-3 PUFA-enriched feeds" South African Journal of Animal Science 2009, 39 (4), pp. 274-285 (Year: 2009).
Therapeutic definition (http://www.thefreedictionary.com/therapeutic) accessed Apr. 29, 2016.
Viscosity (http://www.vp-scientific.com/pdfs/www.liquidcontrol.com_eToolbox_viscosity.pdf) accessed Jan. 6, 2017, pp. 1-4.
Non-Final Office Action issued in U.S. Appl. No. 16/165,628, dated Oct. 28, 2019.
Notice of Allowance issued in U.S. Appl. No. 15/841,993, dated Oct. 30, 2019.
Babaev, Vladimir R., et al., Macrophage Lipoprotein Lipase Promotes Foam Cell Formation and Atherosclerosis in Vivo, 103 The Journal of Clinical Investigation, 1999, 1697-1705.
Non-Final Office Action for U.S. Appl. No. 11/237,264 (listed on SB-08 as U.S. Publication No. US-2006-0067983) dated Jul. 3, 2013.
Non-Final Office Action for U.S. Appl. No. 13/593,656 (listed on SB-08 as U.S. Publication No. US-2012-03115219) dated Jul. 15, 2013.
Notice of Allowance for U.S. Appl. No. 11/525,390 (listed on SB/08 as US-2007/0071798), dated Oct. 4, 2012.
Advisory Action for U.S. Appl. No. 12/581,582 (listed on SB-08 as U.S. Publication No. 2010-0183697, dated Nov. 14, 2012.
Notice of Allowance for U.S. Appl. No. 11/525,390 (listed on SB/08 as U.S. Publication No. US-2007/0071798, dated Nov. 20, 2012.
Non-Final Office Action for U.S. Appl. No. 13/404,487 (listed on SB-08 as US 2012-0213839), dated Dec. 20, 2012.
Non-Final Office Action for U.S. Appl. No. 13/184,512 (listed on SB-08 as US 2012-0016038), dated Jan. 31, 2013.
Non-Final Office Action for U.S. Appl. No. 11/978,840 (listed on SB-08 as US 2008-0118550), dated Feb. 19, 2013.
Non-Final Office Action for U.S. Appl. No. 13/682,991 (listed on SB-08 as US 2013 0074452), dated Mar. 18, 2013.
Notice of Allowance for U.S. Appl. No. 13/404,487 (listed on SB-08 as US 2012-0123839), dated Apr. 2, 2013.
Non-Final Office Action for U.S. Appl. No. 11/236,943 (listed on SB-08 as US 2006-0067975), dated Apr. 22, 2013.
Final Office Action for U.S. Appl. No. 12/182,261 (listed on SB-08 as US 2009/0047414, dated Apr. 30, 2012.
Final Office Action for U.S. Appl. No. 12/401,243 (listed on SB-08 as US 2010/0233232), dated Jun. 11, 2012.
Notice of Allowance for U.S. Appl. No. 12/182,261 (listed on SB-08 as US 2009/0047414), dated Jul. 23, 2012.
Notice of Allowance for U.S. Appl. No. 11/236,908 (listed on SB-08 as US 2006/0067974, dated May 11, 2012.
Advisory Action for U.S. Appl. No. 12/401,243 (listed on SB-08 as US 2010/0233232), dated Aug. 27, 2012.
Final Office Action for U.S. Appl. No. 12/581,582 (listed on SB-08 as US 2010/0183697), dated Aug. 29, 2012.
Non-Final Office Action for U.S. Appl. No. 12/581,582 (listed on SB-08 as US 2010/0183697), dated Mar. 14, 2012.
Non-Final Office Action for U.S. Appl. No. 11/582,135 (listed on SB/08 as US 2007 /0202149), dated Jan. 6, 2010.
Non-Final Office Action for U.S. Appl. No. 11/582,135 (listed on SB/08 as US 2007/0202149), dated May 12, 2009.
Non-Final Office Action for U.S. Appl. No. 11/701,799 (listed on SB/08 as US 2008/0109017), dated Apr. 12, 2010.
Non-Final Office Action for U.S. Appl. No. 11/978,840 (listed on SB/08 as US 2008/0118550), dated Dec. 5, 2010.
Non-Final Office Action for U.S. Appl. No. 11/980,155 (listed on SB/08 as US 2008/0113001), dated Mar. 24, 2011.
Non-Final Office Action for U.S. Appl. No. 12/075,223 (listed on SB/08 as US 2008/0206305), dated Dec. 8, 2010.
Non-Final Office Action for U.S. Appl. No. 12/325,546 (listed on SB/08 as US 2009/0181937), dated Feb. 25, 2010.

(56) References Cited

OTHER PUBLICATIONS

Final Office Action for U.S. Appl. No. 12/325,546 (listed on SB/08 as US 2009/0181937), dated Aug. 31, 2010.
Non-Final Office Action for U.S. Appl. No. 12/364,763 (listed on SB/08 as US 2009/0208552), dated Dec. 11, 2009.
Final Office Action for U.S. Appl. No. 12/364,763 (listed on SB/08 as US 2009/0208552), dated Sep. 21, 2010.
Interview summary for U.S. Appl. No. 11/236,908 (listed on SB/08 as US 2006/0067974) dated May 5, 2009.
Interview summary for U.S. Appl. No. 11/236,908 (listed on SB/08 as US 2006/0067974) dated Dec. 2, 2010.
Interview summary for U.S. Appl. No. 11/582,135 (listed on SB/08 as US 2007/0202149) dated Dec. 7, 2010.
Interview summary for U.S. Appl. No. 12/325,546 (listed on SB/08 as US 2009/0181937) dated Dec. 2, 2010.
Interview summary for U.S. Appl. No. 12/364,763 (listed on SB/08 as US 2009/0208552) dated Dec. 2, 2010.
Final Office Action for U.S. Appl. No. 11/978,840 (listed on SB/08 as US 2008/0118550), dated Jun. 22, 2011.
Non-Final Office Action for U.S. Appl. No. 11/525,390 (listed on SB/08 as US 2007/0071798), dated Jul. 11, 2011.
Non-Final Office Action for U.S. Appl. No. 11/701,799 (listed on SB/08 as US 2008/0109017), dated Aug. 17, 2011.
Final Office Action for U.S. Appl. No. 11/980,155 (listed on SB/08 as US 2008/0113001), dated Oct. 21, 2011.
Non-Final Office Action for U.S. Appl. No. 12/182,261 (listed on SB/08 as US 2009/0047414), dated Dec. 21, 2011.
Non-Final Office Action for U.S. Appl. No. 11/236,908 (listed on SB/08 as US 2006/0067974), dated Dec. 2, 2011.
Non-Final Office Action for U.S. Appl. No. 11/582,135 (listed on SB/08 as US 2007/0202149), dated Oct. 14, 2011.
Non-Final Office Action for U.S. Appl. No. 12/182,165 (listed on SB/08 as US 2009/0011116), dated Jan. 5, 2012.
Non-Final Office Action for U.S. Appl. No. 12/401,243 (listed on SB/08) as US 2010/0233232), dated Jan. 5, 2012.
Notice of Allowance for U.S. Appl. No. 11/582,135 (listed on SB/08 as US 2007/0202149), dated Jan. 9, 2012.
Final Office Action for U.S. Appl. No. 12/075,223 (listed on SB/08 as US 2008/0206305), dated Aug. 11, 2011.
Multanen, M., et al., Bacterial adherence to silver nitrate coated poly-L-lactic acid urological stents in vitro, Urol Res., Oct. 2000, 327-31, 5. (Abstract).
Douglas, Kyle, et al., Zero-Order Controlled-Release Kinetics Through Polymer Matrices, available at http://www.drew.edu/wp-content/uploads/sites/99/Team5.pdf (downloaded Dec. 21, 2016).
Non-Final Office Action issued in U.S. Appl. No. 15/817,018, dated Feb. 6, 2020, 28 pages.
Benchabane et al., Rheological properties of carboxymethyl cellulose (CMC) solutions, Colloid Polym Sci, 2008, 1173-1180, 286.
Extended European Search Report issued in EP Application No. 18000936.7 dated Jan. 7, 2020, 9 pages.
Non-Final Office Action issued in U.S. Appl. No. 16/213,823 dated Feb. 14, 2020, 14 pages.
Van Den Berg et al., Chemical changes in curing and ageing oil paints, ICOM Committee for Conservation, 1999, 248-253, vol. 1.
Office Action issued in EP Application No. 10825447.5 dated Feb. 20, 2020, 4 pages.
Final Office Action issued in U.S. Appl. No. 16/165,628 dated Apr. 13, 2020, 9 pages.
Kaczynski, Jason, "Natural Omega3 Fish Oil Supplements—Howto Avoid Synthetic Fish Oils," accessed online at http://ezinearticles.com/?Natural-Omega3-Fish-Oil-Supplements-How-to-Avoid-Synthetic-Fish-Oils&id=2460278, Jun. 10, 2009.
Luostarinen et al., "Vitamin E supplementation counteracts the fish oil induced increase of blood glucose in humans," Nutrition Research, vol. 15, No. 7, pp. 953-968, 1995.
The Lipid Handbook, 2nd edision, 1994, Tocopherols, pp. 129-131.
Non-Final OA for U.S. Appl. No. 12/767,289 mailed Mar. 15, 2012.
SR for PCT/BE02/00166, dated Apr. 3, 2003.
ESR for EP Application 05012112, dated Jul. 5, 2005.
ESR for EP Application 10157210, dated May 20, 2010.
Non-Final OA for U.S. Appl. No. 11/140,811 mailed Sep. 15, 2008.
Final OA for U.S. Appl. No. 11/140,811 mailed Nov. 25, 2009.
Non-Final OA for U.S. Appl. No. 12/767,289 mailed Aug. 19, 2011.
De Scheerder et al., "Local Angiopeptin Delivery Using Coated Stents Reduces Neointimal Proliferation in Overstretched Porcine Coronary Arteries," J. Invasive Cardiol., 1995, vol. 8, pp. 215-222.
De Scheerder et al., "Experimental Study of Thrombogenicity and Foreign Body Reaction Induced by Heparin-Coated Coronary Stents," Circulation, 1997, vol. 95, pp. 1549-1553.
Schwartz et al., "Restenosis and the Proportional Neointimal Response to Coronary Artery Injury: Results in a Porcine Model," J. Am. Coll. Cardiol., 1992, vol. 19, pp. 267-274.
Pilz and Marz 2008, Free fatty acids as a cardiovascular risk factor. Clin Chem Lab Med, vol. 46, No. 4, pp. 429-434.
Sigma-Aldrich, Polyhydroxy compounds webpage, captured May 28, 2009.
Final Office Action for U.S. Appl. No. 12/182,165 (listed on SB-08 as US 2009-0011116), dated Apr. 6, 2012.
Final Office Action for U.S. Appl. No. 11/701,799 (listed on SB-08 as US 2008-0109017), dated Feb. 13, 2012.
International Search Report for International Application PCT/US05/034601, dated Apr. 10, 2006.
International Search Report for International Application PCT/US05/034610, dated Mar. 16, 2006.
International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
International Search Report for International Application PCT/US05/034681, dated Jul. 26, 2006.
International Search Report for International Application PCT/US05/034682, dated Jul. 20, 2006.
International Search Report for International Application PCT/US05/034836, dated Jul. 6, 2006.
International Search Report for International Application PCT/US06/037184, dated Feb. 22, 2007.
International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US07/022944, dated Apr. 8, 2009.
International Search Report for International Application PCT/US08/000565, dated May 4, 2009.
International Preliminary Examination Report for International Application PCT/US08/071547, dated Aug. 26, 2010.
International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Non-Final Office Action for U.S. Appl. No. 11/236,908 (listed on SB-08 as US 2006/0067974), dated Mar. 25, 2006.
Non-Final Office Action for U.S. Appl. No. 11/236,908 (listed on SB-08 as US 2006/0067974), dated May 17, 2011.
Final Office Action for U.S. Appl. No. 11/236,908 (listed on SB/08 as US 2006/0067974), dated Aug. 24, 2009.

(56) References Cited

OTHER PUBLICATIONS

Final Office Action for U.S. Appl. No. 11/236,943 (listed on SB/08 as US 2006/0067975), dated Dec. 23, 2009.
Non-Final Office Action for U.S. Appl. No. 11/236,943 (listed on SB/08 as US 2006/0067975), dated Mar. 5, 2009.
Non-Final Office Action for U.S. Appl. No. 11/236,977 (listed on SB/08 as US 2006/0088596), dated Aug. 3, 2009.
Final Office Action for U.S. Appl. No. 11/237,263 (listed on SB/08 as US 2006/0110457), dated Jul. 7, 2010.
Non-Final Office Action for U.S. Appl. No. 11/237,263 (listed on SB/08 as US 2006/0110457), dated Oct. 7, 2009.
Final Office Action for U.S. Appl. No. 11/237,264 (listed on SB/08 as US 2006/0067983), dated Jun. 2, 2010.
Non-Final Office Action for U.S. Appl. No. 11/237,264 (listed on SB/08 as US 2006/0067983), Oct. 5, 2009.
Final Office Action for U.S. Appl. No. 11/701,799 (listed on SB/08 as US 2008/0109017), dated Nov. 23, 2010.
Non-Final Office Action for U.S. Appl. No. 11/238,532 (listed on SB/08 as US 2006/0067976), dated Mar. 30, 2009.
Final Office Action for U.S. Appl. No. 11/238,532 (listed on SB/08 as US 2006/0067976), dated Sep. 9, 2009.
Final Office Action for U.S. Appl. No. 11/238,554 (listed on SB/08 as US 2006/0121081), dated May 12, 2010.
Non-Final Office Action for U.S. Appl. No. 11/238,554 (listed on SB/08 as US 2006/0121081), dated Oct. 9, 2009.
Final Office Action for U.S. Appl. No. 11/238,554 (listed on SB/08 as US 2006/0121081), dated May 1, 2009.
Non-Final Office Action for U.S. Appl. No. 11/238,554 (listed on SB/08 as US 2006/0121081), dated Jul. 25, 2008.
Non-Final Office Action for U.S. Appl. No. 11/238,564 (listed on SB/08 as US 2006/0083768), dated Apr. 16, 2008.
Final Office Action for U.S. Appl. No. 11/238,564 (listed on SB/08 as US 2006/0083768), dated Aug. 6, 2009.
Non-Final Office Action for U.S. Appl. No. 11/239,555 (listed on SB/08 as US 2006/0067977), dated Mar. 30, 2009.
Non-Final Office Action for U.S. Appl. No. 11/525,328 (listed on SB/08 as US 2007/0084144), dated Apr. 30, 2007.
Non-Final Office Action for U.S. Appl. No. 11/525,390 (listed on SB/08 as US 2007/0071798), dated Jul. 14, 2010.
Final Office Action for U.S. Appl. No. 11/525,390 (listed on SB/08 as US 2007/0071798), dated Feb. 21, 2011.
Final Office Action for U.S. Appl. No. 11/582,135 (listed on SB/08 as US 2007/0202149), dated May 12, 2011.
Non-Final Office Action for U.S. Appl. No. 11/582,135 (listed on SB/08 as US 2007/0202149), dated Nov. 9, 2010.
Non-Final Office Action issued in U.S. Appl. No. 17/070,914 dated Jun. 10, 2022, 22 pages.
Fish Oil Triglycerides vs. Ethyl Esters: A Comparative Review of Absorption, Stability and Safety Concerns (Ascenta Health Ltd. 2010 at http://www.ascentaprofessional.com/science/articles/fish-oil-triglycerides-vs-ethyl-esters (downloaded Sep. 24, 2015).
Swanson, Danielle, et al., Omega-3 Fatty Acids EPA and DHA: Health Benefits Throughout Life, 3 Advances in Nutrition 1-7 (American Society for Nutrition 2012).
Fats & Oils (2008) at http://scifun.chem.wisc.edu/chemweek/pdf/fats&oils.pdf (downloaded Sep. 24, 2015).
Extended European Search Report dated Dec. 10, 2015 issued for EP Patent Application No. 13804477, 3 pages.
SepraFilm Adhesion Barrier package insert (Genzyme Biosurgery 2008).
Messandro Sannino et al., Biodegradeable Cellulose-based Hydrogels: Design and Applications, 2 MATERIALS, pp. 353-373, 2009.
Thomas Heinze, Carboxymethyl Ethers of Cellulose and Starch—A Review, Center of Excellence for Polysaccharide Research, Friedrich Schiller University of Jena (Germany), pp. 13-29, 2005.
H. Omidian, et al., Swelling Agents and Devices in Oral Drug Delivery, J. Drug. Del. Sci. Tech., No. 18, vol. 2, 2008, pp. 83-93.
S. Kamel et al., Pharmaceutical Significance of Cellulose: A Review, Express Polymer Letters vol. 2, No. 11, 2008, pp. 758-778.

A. M. Adel et al., Carboxymethylated Cellulose Hydrogel: Sorption Behavior and Characterization, Nature and Science, No. 8, vol. 8, 2010, pp. 244-256.
Bacteria in Water, The USGS Water Science School, http://water.usgs.gov/edu/bacteria.html (downloaded Nov. 9, 2015).
Novotny, L. et al., Fish: a potential source of bacterial pathogens for human beings, Vet. Med.—CZECH, 49, 2004, vol. 9, pp. 343-358.
Allergies, Asthma and Allergy Foundation of America (2011), http://www.aafa.org/page/types-of-allergies.aspx (downloaded Oct. 5, 2015).
Sicherer, Scott H., Food Allergies: A Complete Guide for Eating When Your Life Depends on it, 2013, 15, Johns Hopkins University Press, Baltimore, MD, USA.
Omega-3 DHA—The Problem May Be the Quality of Your Fish Oil, Not Your Allergy to Fish, Fatty Acids Hub, http://www.fattyacidshub.com/fatty-acids/omega-3-dha/ (downloaded Nov. 10, 2015).
Soy Allergy, Asthma and Allergy Foundation of America (2005), http://www.aara.org/display.cfm?id=9&sub=20&cont=522 (downloaded Nov. 10, 2015).
Refined soybean oil not an allergen, say food scientists, FOOD navigator-USA.com (2005), http://www.foodnavigator-usa.com/content/view/print/127438 (downloaded Nov. 10, 2015).
Yahyaee, R. et al., Waste fish oil biodiesel as a source of renewable fuel in Iran, Renewable and Sustainable Energy Reviews, 2013, pp. 312-319, 17, Elsevier Ltd.
Biological evaluation of medical devices—Part 1: Evaluation and testing, International Standard ISO 109931-1, Aug. 1, 2003, Third Edition, Switzerland.
Mayo Clinic (http://www.mayoclinic.org/drugs-supplements/omega-3-fatty-acids-fish-oil-alpha-linolenic-acids/safety/hrb-20059372?p=1 (downloaded Sep. 28, 2015).
Milk allergy, at http://www.mayoclinic.org/diseases-conditions/milk-allergy/basics/definition/con-20032147?p=1 (downloaded Jul. 29, 2015).
Soy allergy, at http://www.mayoclinic.org/diseases-conditions/soy-allergy/basics/definition/con-20031370?p=1 (downloaded Jul. 29, 2015).
F.D. Gunstone, Fatty Acid and Lipid Chemistry 72 (1999).
Hawley's Condensed Chemical Dictionary 315, 316, 332, 333, 334, 825 and 826 (2001).
Herbert O. Hultin et al., Chemical Composition and Stability of Fish Oil (International Association of Fish Meal Manufacturers Apr. 10, 1991).
F.V.K Young, The Chemical & Physical Properties of Crude Fish Oils for Refiners and Hydrogenators, 18 Fish Oil Bulletin 1-18 (1986).
Neva L. Karrick, Nutritional Value of Fish Oils as Animal Feed, Circular 281 (Fish and Wildlife Service Bureau of Commercial Fisheries 1967), reprinted from M.E. Stansby (ed.), Fish Oils 362-382 (Avi Publishing Company 1967).
Luley et al., Fatty acid composition and degree of peroxidation in fish oil and cod liver oil preparations, Arzneimittelforschung. Dec. 1998, vol. 38, No. 12, pp. 1783-1786.
Mallegol, Drier influence on the curing of linseed oil, Progress in Organic Coatings, Nov. 2000, vol. 39, No. 2, pp. 107-113.
Morse, Molecular distillation of polymerized drying oils, Ind. Eng. Chem., 1941, No. 33, pp. 1039-1043.
Drying Oil, http://en.wikipedia.org/wiki/drying_oil (downloaded Jun. 28, 2013).
Szebeni et al., "Complement Activation by Cremophor EL as a Possible Contributor to Hypersensitivity to Paclitaxel an In Vitro Study", Journal of the National Cancer Institute, 1998, vol. 90, No. 4, pp. 300-306.
Birsan, et al., "The novel calcineurin inhibitor ISA247: a more potent immunosuppressant than cyclosporine in vitro", Transpl. Int., 2005, vol. 17, pp. 767-771.
About.com, "Orthopedics, Synvisc injections," retrieved online at http://orthopedics.about.com/cs/treatment/a/synvisc_2.htm (2005).
Cath Lab Digest, "Olive Oil Emulsion Helps With Problem Heart Arteries", retrieved online at http://www.cathlabdigest.com/displaynews.cfm?newsid=0103073 (2007).
Doctor's Guide to Medical and Other News, "AAOS Meeting: Synvisc Delays Total Knee Replacement in Osteoarthritis Patients",

(56) References Cited

OTHER PUBLICATIONS retrieved online at http://www.docguide.com/dg.nsf/PrintPrint/ 4585EC355198EEF08525670E006B10FF (1999).

Methodist, "Evaluation of Biocompatibility and Antirestenotic Potential of Drug Eluting Stents Employing Polymer-free Highly-Hydrogenated Lipid-Based Stent Coatings in Porcine Coronary Arteries", Transcatheter Cardiovascular Therapeutics (TCT), sponsored by the Cardiovascular Research Foundation®, Oct. 22-27, 2006, Washington Convention Center, Washington, D.C.

Novavax, retrieved online at http://www.novavax.com/go.cfm?do=Page.View&pid=3 (2006).

Orthovisc, "New Treatment Option is Potential Alternative to OTC Pain Medications for Osteoarthritis of the Knee" retrieved online at http://www.jnj.com/innovations/new_features/ORTHOVISC.htm:iessionid=33N2RBQDV0DZKCQPCCEGU3AKB2IIWTT1 (2006).

Orthovisc, "What is ORTHOVISC®?" retrieved online at http://www.orthovisc.com/xhtmlbgdisplay.jhtml?itemname=about_orthovisc (2005).

Orthovisc, "Your Knees and Osteoarthritis", retrieved online at http://www.orthovisc.com/xhtmlbgdisplay.jhtml?itemname=understanding_knee_oa (2003).

Orthovisc, "What to expect from your treatment," retrieved online at http://www.orthovisc.com/xhtmlbgdisplay.jhtml?itemname=what_to_expect (2007).

Orthovisc, "Tools and Resources for Managing Your Osteoarthritis", retrieved online at http://www.orthovisc.com/xhtmlbgdisplay.jhtml?itemname=patient_resources (2007).

Pohibinska, A., et al., "Time to reconsider saline as the ideal rinsing solution during abdominal surgery", The American Journal of Surgery, vol. 192, pp. 281-222 (2007).

Singh, Alok, et al., "Facilitated Stent Delivery Using Applied Topical Lubrication", Catherization and Cardiovascular Interventions, vol. 69, pp. 218-222 (2007).

Urakaze, Masaharu et al., "Infusion of fish oil emulsion: effects on platelet aggregation and fatty acid composition in phospholipids of plasma, platelets and red blood cell membranes in rabbits", Am. J. Clin. Nutr., vol. 46, pp. 936-940 (!987).

Hortolam, Juliane G., et al., "Connective tissue diseases following silicone breast implantation: where do we stand?", Clinics, 2013, vol. 3, p. 281.

Lidar, M. et al., "Silicone and sclerodema revisited", Lupus, 2012, vol. 21, pp. 121-127.

"Lead", Article by Centers for Disease Control and Prevention (CDC), Nov. 2009, 2 pages.

"Evaluation of the Biocompatibility and Drug Delivery Capabilities of Biological Oil Based Stent Coatings", by Li, Shengqiao of the Katholieke Universiteit Leuven, 63 pages.

Fimar-Balzsy et al., Chemical Principles of Textile Conservation, Oxford: Elsevier Science Ltd., 1998, pp. 117-119.

CECW-EE, "Ch. 4: Coating Types and Characteristics", Engineering and Design—Painting: New Construction and Maintenance, 1995, pp. 4-1 to 4-24.

Wikipedia, "Sirolimus", pp. 1-13, available online at http://en.wikipedia.org/wiki/sirolimus, accessed May 11, 2011.

Binder et al., "Chromatographic Analysis of Seed Oils. Fatty Acid Composition of Castor Oil", The Journal of American Oil Chemists' Society, 1962, vol. 39, pp. 513-517.

Supplementary ESR in AMC-427-EP1, dated Jul. 26, 2011, EP05804291.

Supplementary ESR in AMC-449-EP1 dated Jul. 27, 2011.

Supplementary ESR in AMC-448-EP1 dated Aug. 19, 2011.

Crivello et al., "Epoxidized triglycerides as renewable monomers in photoinitiated cationic polymerization", Chem. Water. 1992, pp. 692-699.

Supplementary ESR in AMC-446-EP1 dated Aug. 18, 2011.

Encyclopedia Britannica Online, "Surface Coating", available online at http://www.britannica.com/Ebchecked/topic/575029/surface-coating>, accessed Jun. 17, 2011.

Supplementary European Search Report for Application No. EP 08877338.7, dated Aug. 16, 2012.

Supplementary European Search Report for Application No. EP09819594.4, dated Aug. 14, 2012.

International Search Report for PCT/US2011/44292, dated Dec. 6, 2011.

Ahuja et al., "Prevention of Postoperative Intraperitoneal Adhesions—An Experimental Study in Rats", Journal of Indian Pediatric Surgery 2002 7:15-20.

Jonasson, Lena et al., "Cyclosporon A inhibits smooth muscle proliferation in the vascular response to injury," Proc. Natl. Acad. Sci. USA, vol. 85: 2303-2306 (1988).

Ogunniyi, D.S., "Castor oil: A vital industrial raw material," Biosource Technology, vol. 97: 1086-1091 (2006).

Redman, L.V. et al., "The drying rate of raw paint oils—a comparison," The Journal of Industrial and Engineering Chemistry, vol. 5: 630-636 (1913).

Rutkow, Ira M. et al., "'Tension-free' inguinal herniorrhaphy: A preliminary report on the 'mesh plug' technique," Surgery, vol. 114:3-8 (1993).

Websters Dictionary Online, Accessed on Feb. 13, 2009, entry for "polymer" p. 1 of 1.

International Search Report for International Application PCT/US05/034941, dated May 4, 2006.

Ackman, R.G., "Fish Oils", Bailey's Industrial Oil and Fat Products, 6th Edition, 279-317 (2005).

Andres, et al. "Antiproliferative Strategies for the Treatment of Vascular Proliferative Disease", Current Vascular Pharmacology, 1)1): 85-98 (2003).

Winter, et al., "Physical and Chemical Gelation" Encyclopedia of Materials—Science and Technology, vols. 1-11: 5691-6999 (2001).

Supplementary European Search Report for EP12004057, dated Apr. 10, 2013.

Lipids, Chapter 19, pp. 1-12 (2002).

Jorge, N., "Grasas y Aceites", 48(1): 17-24, (1997).

International Search Report for International Application PCT/US2013/044653, dated Sep. 4, 2013.

Mallegol, "Long-Term Behavior of Oil-Based Varnishes and Paints Photo-and Thermooxidation of Cured Linseed Oil", Journal of the American Oil Chemists' Society, 77:257-263 (2000).

Supplementary European Search Report for Application No. EP 10825447, dated Mar. 31, 2014.

Uchida, et al., "Swelling Process and Order-Disorder Transition of Hydrogel Containing Hydrophobic Ionizable Groups", Macromolecules, 28, 4583-4586 (1995).

Gutfinger, et al., "Polyphenols in Olive Oils", Journal of the American Oil Chemists Society, 58(11): 966-968 (1981).

de la Portilla, et al., "Prevention of Peritoneal Adhesions by Intraperitoneal Administration of Vitamin E: An Experimental Study in Rats", Diseases of the Colon and Rectum, 47; 2157-2161 (2005).

Sano, et al., "A controlled Trial of Selegiline, Alpha-Tocopherol, or Both as Treatment for Alzheimer's Disease", The New England Journal of Medicine, 336; 1216-1222 (1997).

Wikipedia, Sunflower oil, accessed Jul. 23, 2015, pp. 1-7.

Esoteric Oils, Peppermint essential oil information, accessed Jul. 23, 2015, pp. 1-7.

Orthomolecular, Fish Oil, Jun. 29, 2004, http://orthomolecular.org/nutrients/fishoil.html, accessed Jul. 22, 2015, p. 1.

Wicks et al. Organic Coatings:Science and Technology 1999 New York:Wiley Interscience p. 258-267.

Mills et al. Oils and Fats. "The Organic Chemistry of Museum Objects" London:Buttersworth and Co. 1987, p. 26-40.

Erhardt Paints Based on Drying Oil Media. Painted Wood: History & Conservation. Ed. Berland Singapore: The J. Paul Getty Trust 1998. p. 17-32.

Wexler et al. Chemical Reviews 1964 64(6):591-611.

Polymer—The Chambers 21st Century Dictionary M. Robinson and G. Davidson (Eds.), London, United Kingdom: Chambers Harrap. Retrieved from http://search.credoreference.eom/content/entry/chambdict!polymer/O; 2001.

Polymer—Academic Press Dictionary of Science and TechnologyC. Morris (Ed.), Academic Press Dictionary of Science and Technol-

(56) References Cited

OTHER PUBLICATIONS ogy. Oxford, United Kingdom: Elsevier Science & Technology. Retrieved from http://search.credoreference.com/content/entry/apdst!polymer/O; 1992.

Falagas et al. European Society of Clinical Microbiology and Infection Diseases 2005 11:3-8.

Bimbo (INFORM 1998 9(5):473-483.

H. Fineberg et al., Industrial Use of Fish Oils, pp. 222-238, http://spo.nmfs.noaa.gov/Circulars/CIRC278.pdf, downloaded Aug. 3, 2015.

Lewis, Richard J., Sr., Hawley's Condensed Chemical Dictionary, 2001, pp. 308, 309 and 896-898, 14th edision, John Wiley & Sons, Inc., New York.

Webster's II New College Dictionary (1995), 1075, Houghton Mifflin Company, New York, US.

Polymers made from multiple monomers, A Natural Approach to Chemistry, Chapter 8, 241, http://lab-aids.com/assets/uploads/NAC/NAC_student_book/Texas%20Student%20Edition%20253.pdf (downloaded Dec. 3, 2015).

Polymer, Encyclopedia Britannica. Encyclopedia Britannica Online, Encyclopedia Britannica Inc., 105, Web. Dec. 2, 2015, http://www.britannica.com/print/article/468696 (downloaded Dec. 2, 2015).

Triglycerides, https://www.lipid.org/sites/default/files/triglycerides.pdf (downloaded Sep. 24, 2015).

Autosuture, "Parietex TM Composite OS Series Mesh", retrieved online at http://www.autosuture.com/AutoSuture/pagebuilder.aspx?topicID=135734&breadcrumbs=135601:0 (2007).

Camurus, "In our endeavors to create the unique, we start with the best. Your product".

De Scheerder, Ivan K. et al., "Biocompatibility of polymer-coated oversized metallic stents implanted in normal porcine coronary arteries", Atherosclerosis, vol. 114, pp. 105-114; 1995.

Drummond, Calum J. et al., "Surfactant self-assembly objects as novel drug delivery vehicles", Current Opinion in Colloid & Interface Science, 2000, vol. 4, pp. 449-456.

Engstrom, Sven, "Drug Delivery from Cubic and Other Lipid-water Phases", Lipid Technology, 1990, vol. 2, No. 2, pp. 42-45.

Guler et al., "Some empirical equations for oxopolymerization of linseed oil", Progress in Organic Coatings, 2004, vol. 51, pp. 365-371.

Hwang, Chao-Wei et al., "Physiological Transport Forces Govern Drug Distribution for Stent-Based Delivery", Circulation, 2001, vol. 104, pp. 600-605.

Oberhoff, Martin et al., "Local and Systemic Delivery of Low Molecular Weight Heparin Following PTCA: Acute Results and 6-Month Follow-Up of the Initial Clinical Experience With the Porous Balloon (PILOT-Study)," Catheterization and Cardiovascular Diagnosis, 1998, vol. 44, pp. 267-274.

"polymerization", Merriam-Webster Online Dictionary, retrieved from www.merriam-webster.com on Dec. 13, 2009, p. 1.

Salu, Koen J. et al., "Addition of cytochalasin D to a biocompatible oil stent coating inhibits intimal hyperplasia in a porcine coronary model", Coronary Artery Disease, 2003, vol. 14, No. 8, pp. 545-555.

Scheller, Bruno et al., "Addition of Paclitaxel to Contrast Media Prevents Restenosis After Coronary Stent Implantation", Journal of the American College of Cardiology, 2003, vol. 42, No. 8, pp. 1415-1420.

Shahidi, Fereidoon ed.; "Bailey's Industrial Oil and Fats Products" 2005: John Wiley and Sons; vol. 5, Edible Oil and Fat Products, Processing Technologies, pp. 1-15.

Van Der Giessen, Willem J. et al., "Marked inflammatory Sequelae to Implantation of Biodegradable and Nonbiodegradable Polymers in Porcine Coronary Arteries", Circulation, 1996, vol. 94, pp. 1690-1697.

Henderson, R. James et al., "Hydrolysis of Fish Oils Containing Polymers of Triacylglycerols by Pancreatic Lipase in vitro", LIPIDS, vol. 28, No. 4, 1993, pp. 313-319.

"cure" in Academic Press Dictionary of Science and Technology, 1992.

Oxford Reference, A Dictionary of Chemistry, 6th edition, John Daintith, 2008, 3 pages.

Saghir et al., "Rapid in vivo hydrolysis of fatty acid ethyl esters, toxic nonoxidative ethanol metabolites", American Journal of Physiology, 1997, pp. G184-G190.

Non-Final Office Action issued in U.S. Appl. No. 13/184,512, dated May 1, 2018.

Final Office Action issued in U.S. Appl. No. 13/184,512, dated Mar. 22, 2017.

Non-Final Office Action issued in U.S. Appl. No. 13/184,512, dated Sep. 12, 2016.

Final Office Action issued in U.S. Appl. No. 13/184,512, dated Apr. 28, 2015.

Non-Final Office Action issued in U.S. Appl. No. 13/184,512, dated Oct. 10, 2014.

Final Office Action issued in U.S. Appl. No. 13/184,512, dated Jun. 25, 2013.

Non-Final Office Action issued in U.S. Appl. No. 13/184,512, dated Jan. 31, 2013.

Wagner et al., Effects of tocopherols and their mixtures on the oxidative stability of olive oil and linseed oil under heating, European Journal of Lipid Science and Technology, 2000, 624-629, 102.

Oliveira et al., Triglyceride Hydrolysis of Soy Oil vs Fish Oil Emulsions, Journal of Parenteral and Enteral Nutrition, 1997, 224-229, 21, 4.

Evans, D.F., et al., Measurement of gastrointestinal pH profiles in normal ambulant human subjects, GUT, 1988, 1035-1041, 29.

Final Office Action issued in U.S. Appl. No. 11/701,799, dated Mar. 12, 2015.

Final Office Action issued in U.S. Appl. No. 12/581,582, dated Jan. 8, 2015.

Notice of Allowance issued in U.S. Appl. No. 13/943,489, dated Jan. 29, 2015.

Non-Final Office Action issued in U.S. Appl. No. 11/980,155, dated Nov. 7, 2014.

Notice of Allowance issued in U.S. Appl. No. 12/364,763, dated Dec. 5, 2014.

Notice of Allowance issued in U.S. Appl. No. 12/325,546, dated Dec. 8, 2014.

Non-Final Office Action for U.S. Appl. No. 12/581,582 (listed on SB-08 as U.S. Publication 2010-0183697), dated May 29, 2014.

Non-Final Office Action for U.S. Appl. No. 13/943,489, dated Jul. 1, 2014.

Final Office Action for U.S. Appl. No. 11/980,155, dated Jul. 21, 2014.

Non-Final Office Action issued in U.S. Appl. No. 12/325,546, dated Apr. 22, 2014.

Non-Final Office Action issued in U.S. Appl. No. 12/364,763, dated Apr. 23, 2014.

Non-Final Office Action for U.S. Appl. No. 11/701,799, dated Jul. 22, 2014.

Notice of Allowance issued in U.S. Appl. No. 11/236,943, dated Oct. 6, 2014.

Notice of Allowance issued in U.S. Appl. No. 11/237,264, dated Mar. 27, 2014.

Notice of Allowance issued in U.S. Appl. No. 11/237,263, dated Mar. 27, 2014.

Final Office Action issued in U.S. Appl. No. 11/236,943, dated Dec. 4, 2013.

Final Office Action issued in U.S. Appl. No. 11/237,264, dated Dec. 17, 2013.

Notice of Allowance issued in U.S. Appl. No. 13/593,656, dated Jan. 24, 2014.

Non-Final Office Action issued in U.S. Appl. No. 11/980,155, dated Nov. 12, 2013.

Notice of Allowance issued in U.S. Appl. No. 13/682,991, dated Aug. 1, 2013.

Notice of Allowance issued in U.S. Appl. No. 11/978,840, dated Aug. 6, 2013.

Bruno, Gene, Omega-3 Fatty Acids, Literature Education Series on Dietary Supplements, Huntington College of Health Sciences, 2009, 1-4.

(56) References Cited

OTHER PUBLICATIONS

Web article from http://www.buchi.com, "Slip Melting Point Determination of Palm Stearin", 1 page.
Notice of Allowance for U.S. Appl. No. 11/525,390 (listed on SB/08 as US-2007/0071798), dated Nov. 30, 2012.
Interview summary for U.S. Appl. No. 11/237,420 (listed on SB08a as US 2006/0078586) dated May 5, 2009.
American heritage desk dictionary, 1981. p. 799, 2 pages.
John McMurray, Organic Chemistry, third edition, 1992, pp. 45-48.
9.1 Terminology for Vegetable Oils and Animal Fats, at http://www.e-education.psu.edu/egee439/node/683 (downloaded Sep. 13, 2017), pp. 1-8.
Sunflower Oil, at https//en.wikipedia.org/wiki/Sunflower_oil (downloaded Sep. 19, 2017, pp. 1-8.
Fatty Acid Composition of Marine Oils by GLC, AOCS Official Method Ce 1b-89 (2009), pp. 1-7.
Preparation of Methyl Esters of Fatty Acids, AOCS Official Method Ce 2-66 (2009), pp. 1-2.
European Extended Search Report dated Jan. 18, 2016, issued for corresponding EP Patent Application No. 11807612.4, 7 pages.
International Preliminary Reporton Patentability for Application No. PCT/US08/85386, dated Apr. 12, 2011.
International Search Report for Application No. PCT/US10/048167, dated Oct. 20, 2010.
Non-Final Office Action for U.S. Appl. No. 12/401,228, dated Nov. 12, 2010.
Non-Final Office Action for U.S. Appl. No. 11/711,389, dated Dec. 17, 2010.
Final Office Action for U.S. Appl. No. 11/250,768, dated Nov. 9, 2010.
Office Action issued in CN Application No. 201610998395.8 dated Apr. 28, 2020.
Office Action issued in CN Application No. 201610997993.3 dated May 11, 2020.
Office Action issued in CN Application No. 201610998395.8 dated Oct. 22, 2020, 13 pages.
Office Action issued in U.S. Appl. No. 16/165,628 dated Dec. 1, 2020, 15 pages.
Office Action and Search Report issued in CN Application No. 201610998395.8 dated Mar. 22, 2021, 25 pages.

\* cited by examiner

Carbon-Carbon (C-C) Cross-linking of Fatty Acid Chains

Summary of Oil-Derived Biomaterial Reaction Chemistry

Ester and Lactone Cross-Links
Formed Results in
Solidifying the Coating into a Gel.

Volatilization of Water, Hydrocarbons
and Aldehydes, Resulting in
An Increase in Coating Viscosity.

Isomerization and Oxidation of C=C Bonds.

*Fig. 4*

ESTERIFICATION
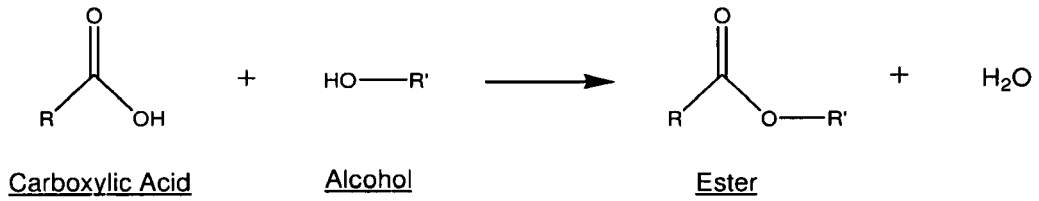
Carboxylic Acid  Alcohol  Ester
ALCOHOLYSIS
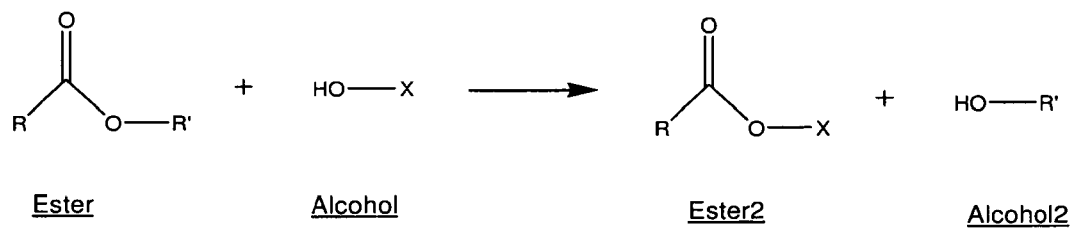
Ester  Alcohol  Ester2  Alcohol2
ACIDOLYSIS
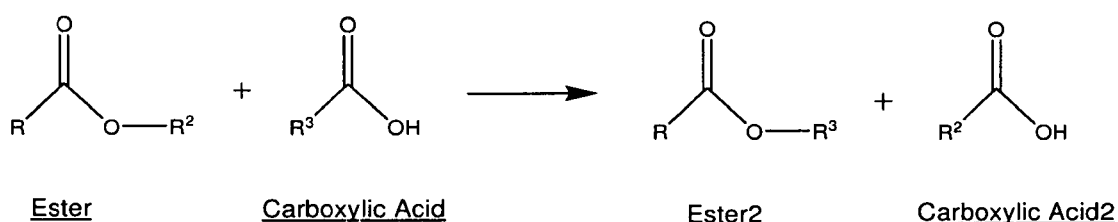
Ester  Carboxylic Acid  Ester2  Carboxylic Acid2
INTERESTERIFICATION
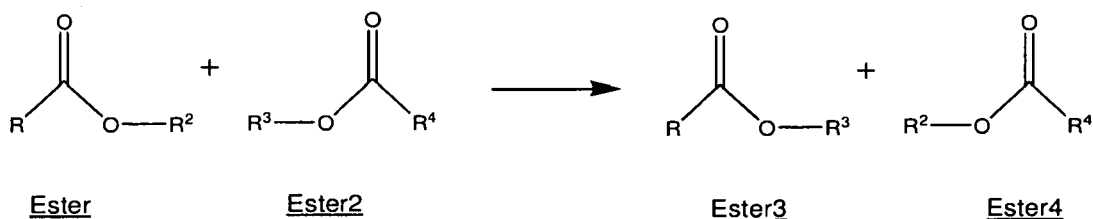
Ester  Ester2  Ester3  Ester4
*Fig. 5*

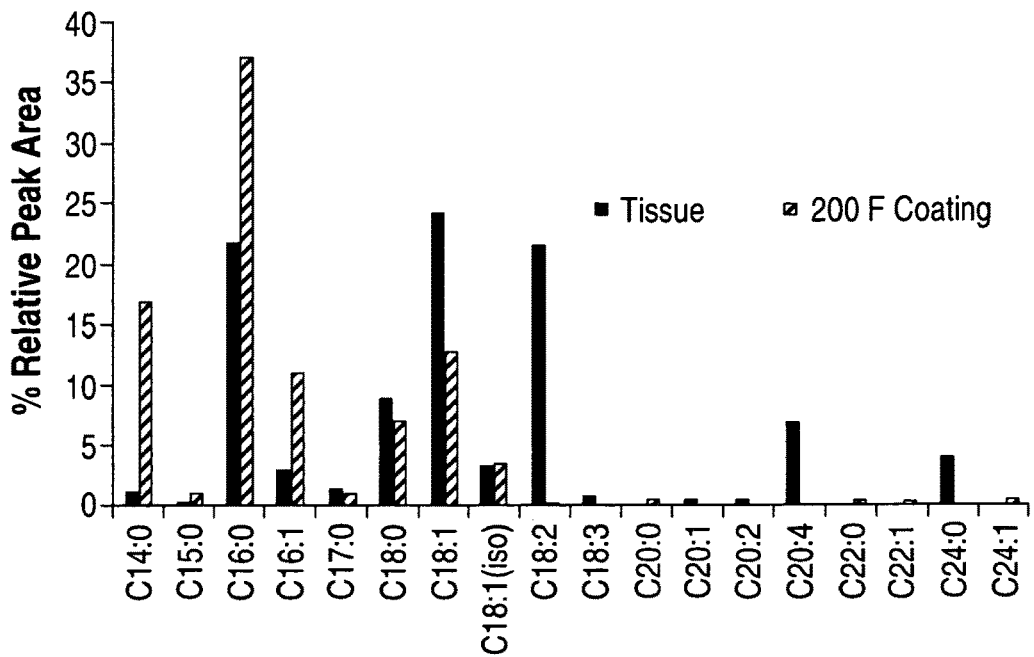
Fig. 7
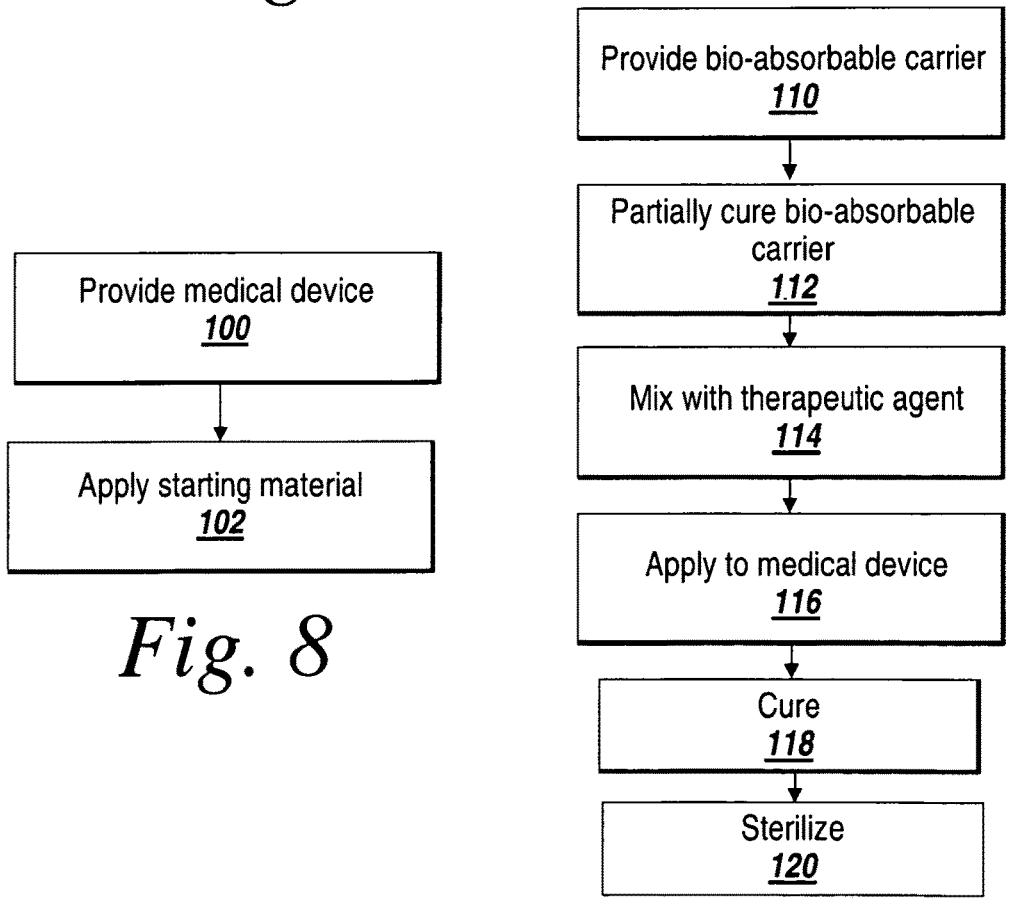
Fig. 8
Fig. 9

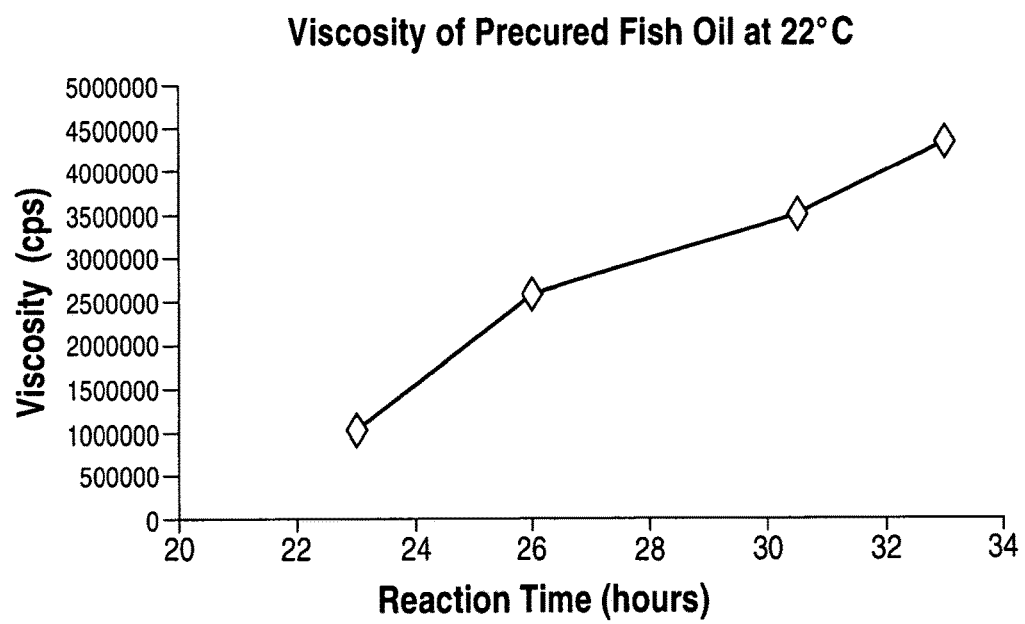
*Fig. 19*
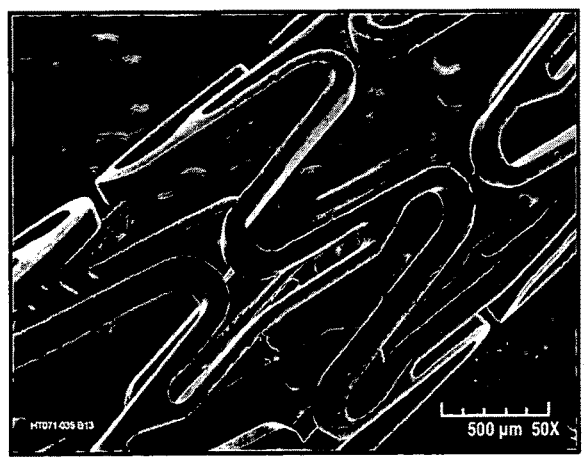 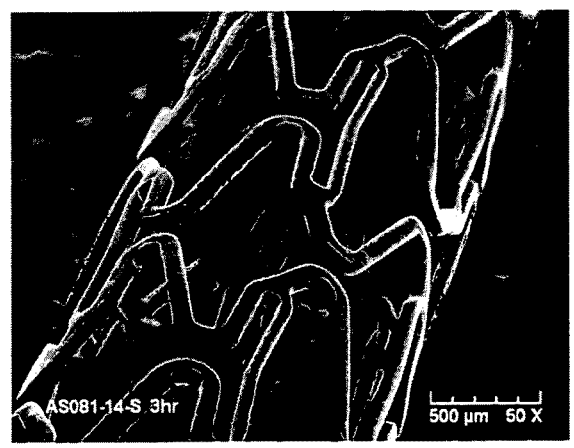
*Fig. 20A*        *Fig. 20B*

Representative low (4x) and high (20x) power images of BMS. Animal 03 / CV21077 LCX Distal. Sections shown are stained by Elastin Van Gieson (EVG, 2x), and Hematoxylin & Eosin (H&E 20x).

Representative low (4x) and high (20x) power images of XRG-RC. Animal 03 / CV21077 RCA Mid. Sections shown are stained by Elastin Van Gieson (EVG, 2x), and Hematoxylin & Eosin (H&E 20x).

Representative low (4x) and high (20x) power images of XRG-R100. Animal 02/CV21076 LCX Mid. Sections shown are stained by Elastin Van Gieson (EVG, 2x), and Hematoxylin & Eosin (H&E 20x).

CROSS-LINKED FATTY ACID-BASED BIOMATERIALS

RELATED APPLICATIONS

This application is a divisional application of U.S. patent application Ser. No. 15/794,086 filed on Oct. 26, 2017, which is a divisional application of U.S. patent application Ser. No. 14/679,368 filed on Apr. 6, 2015 (now U.S. Pat. No. 9,827,352 B2), which is a continuation application of U.S. patent application Ser. No. 12/364,763 filed on Feb. 3, 2009 (now U.S. Pat. No. 9,000,040, which claims priority to U.S. Provisional Application No. 61/104,568, filed on Oct. 10, 2008 and U.S. Provisional Application No. 61/104,575, filed on Oct. 10, 2008. U.S. patent application Ser. No. 12/364,763 is also a continuation-in-part of U.S. patent application Ser. No. 11/582,135, filed Oct. 16, 2006 (now U.S. Pat. No. 8,124,127), which claims priority to U.S. Provisional Patent Application Ser. No. 60/727,312, filed on Oct. 15, 2005. U.S. patent application Ser. No. 12/364,763 is also a continuation-in-part of U.S. patent application Ser. No. 11/236,908, filed Sep. 28, 2005 (now U.S. Pat. No. 8,263,102), which claims priority to U.S. Provisional Application No. 60/613,745, filed Sep. 28, 2004. U.S. patent application Ser. No. 12/364,763 is also a continuation-in-part of U.S. patent application Ser. No. 11/237,264 (now U.S. Pat. No. 8,795,703), filed Sep. 28, 2005, which claims priority to U.S. Provisional Application No. 60/613,808, filed Sep. 28, 2004. The entire contents of these previously filed applications and patents are hereby incorporated herein by reference.

BACKGROUND OF THE INVENTION

Vascular interventions, such as vascular reperfusion procedures, balloon angioplasty, and mechanical stent deployment, can often result in vascular injury following mechanical dilation and luminal expansion of a narrowed vessel. Often, subsequent to such intravascular procedures, neointimal proliferation and vascular injury remodeling occurs along the luminal surface of the injured blood vessel; more specifically, remodeling occurs in the heart, as well as in vulnerable peripheral blood vessels like the carotid artery, iliac artery, femoral and popliteal arteries. No known mechanical suppression means has been found to prevent or suppress such cellular proliferation from occurring immediately following vascular injury from mechanical reperfusion procedures. Left untreated, restenosis commonly occurs following a vascular intervention within the treated vessel lumen within weeks of a vascular injury. Restenosis, induced by localized mechanical injury, causes proliferation of remodeled vascular lumen tissue, resulting in re-narrowing of the vessel lumen, which can lead to thrombotic closure from turbulent blood flow fibrin activation, platelet deposition and accelerated vascular flow surface injury. Restenosis pre-disposes the patient to a thrombotic occlusion and the stoppage of flow to other locations, resulting in critical ischemic events, often with morbidity.

Restenosis initiated by mechanical induced vascular injury cellular remodeling can be a gradual process. Multiple processes, including fibrin activation, thrombin polymerization and platelet deposition, luminal thrombosis, inflammation, calcineurin activation, growth factor and cytokine release, cell proliferation, cell migration and extracellular matrix synthesis each contribute to the restenotic process. While the exact sequence of bio-mechanical mechanisms of restenosis is not completely understood, several suspected biochemical pathways involved in cell inflammation, growth factor stimulation and fibrin and platelet deposition have been postulated. Cell derived growth factors such as platelet derived growth factor, fibroblast growth factor, epidermal growth factor, thrombin, etc., released from platelets, invading macrophages and/or leukocytes, or directly from the smooth muscle cells, provoke proliferative and migratory responses in medial smooth muscle cells. These cells undergo a change from the contractile phenotype to a synthetic phenotype. Proliferation/migration usually begins within one to two days post-injury and peaks several days thereafter. In the normal arterial wall, smooth muscle cells proliferate at a low rate, approximately less than 0.1 percent per day.

However, daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired, at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells derived from the medial layer of the vessel wall continually invade and proliferate at the site of vascular injury as part of the healing process. Within three to seven days post-injury, substantial inflammatory cell formation and migration have begun to accumulate along the vessel wall to obscure and heal over the site of the vascular injury. In animal models, employing either balloon injury or stent implantation, inflammatory cells may persist at the site of vascular injury for at least thirty days. Inflammatory cells may contribute to both the acute and protracted chronic phases of restenosis and thrombosis.

Today, a preferred approach to the local delivery of a drug to the site of vascular injury caused by an intravascular medical device, such as a coronary stent, is to place a drug eluting coating on the device. Clinically, medical devices coated with a drug eluting coating comprised of either a permanent polymer or degradable polymer and an appropriate therapeutic agent have shown angiographic evidence that vascular wall proliferation following vascular injury and/or vascular reperfusion procedures can be reduced, if not eliminated, for a certain period of time subsequent to balloon angioplasty and/or mechanical stent deployment. Local delivery of a single sirolimus or taxol compound via a drug eluting medical device has been shown to be effective at minimizing or preventing cellular proliferation and cellular remodeling when applied immediately after vascular injury. Various analogs of these two anti-proliferative compound examples have also been shown experimentally and clinically to exhibit similar anti-proliferative activity with similar drug eluting coatings. However, anti-proliferative compounds such as sirolimus and taxol, together with a polymeric drug eluting coating have also been shown clinically to exhibit a number of toxic side effects, during and after principal drug release from the drug eluting coating. These chronic and or protracted side effects place limits on the amount of drug that can actually be delivered over a given period of time, as well as challenge the compatibility of the polymer coatings used to deliver a therapeutic agent locally to the site of the vascular injury when applied directly to a site of inflammation and or cellular remodeling. In addition, local overdosage of compounds like sirolimus and taxol can prevent, limit or even stop cellular remodeling or proliferation in and around the localized tissue area of the medical device. For example, a lack of endothelial cell coverage during the interruption of cell proliferation thoughout the vascular injury healing process exhibits a high potential for luminal thrombosis whereby fibrin and a constant deposition of platelets blanket the exposed and non-healed medical device and/or damaged vascular wall. Without uninterrupted systemic support or administration of an anti-platelet medication like clopidegrel combined with an anti-clotting agent, such as ASA, prior to and following deployment of a drug eluting medical device, such devices have been shown clinically to thrombose and occlude within days of deployment. In addition, although these commercially available drug eluting polymer coatings employed on medical devices are generally characterized as being biocompatible, the lack of chemical hydrolysis, degradation and absorption of these polymer-based chemistries into smaller, easier to metabolize chemical components or products have now been clinically demonstrated to initiate a protracted localized inflammatory response at the site of the vascular injury, which may lead to unexpected thrombotic occlusion within days of stopping anti-platelet medication.

Wound healing or response to in-vivo injury (e.g., hernia repair) follows the same general biological cascade as in vascular injury (see, e.g., Y. C. Cheong et al. *Human Reproduction Update.* 2001; Vol. 7, No. 6, pgs 556-566). This cascade includes inflammation of native tissue followed by migration and proliferation of cells to mitigate the inflammatory response, including platelets and macrophages, and a subsequent healing phase which includes fibrin deposition and the formation of fibrin matrix followed by tissue remodeling. In the case of hernia repair, abnormal peritoneal healing can occur when there is the expression of inflammatory cytokines from macrophages (e.g., $\alpha$-TNF) that can result in an inability of the fibrin matrix to be properly broken down and can result in the formation of adhesions (Y. C. Cheong et al., 2001). Abdominal adhesions formed after hernia repair can result in pain, bowel strangulation, infertility and in some cases death (Y. C. Cheong et al., 2001).

The sustained nature of the thrombotic and inflammatory response to injury makes it desirable to provide a biomaterial that can reduce the incidence of inflammatory and foreign body responses after implantation. It would also be preferable to have a biomaterial that provides release of one or more therapeutic agents over a period of time in order to minimize such cell activated responses. Additionally, such a biomaterial would also preferably be metabolized via a bioabsorption mechanism.

SUMMARY OF THE INVENTION

What is desired is a biomaterial (e.g., a coating or stand-alone film) that can be utilized alone or as a drug delivery carrier that prevents or diminishes chronic inflammation due to either the therapeutic agent or components of the coating. Furthermore, it is desirable that the biomaterial release and deliver therapeutic agents in a sustained and controlled fashion to local tissue. The present invention is directed toward various solutions that address this need.

What is also desired is a biomaterial (e.g., a coating or stand-alone film) that can be bioabsorbed by cells and that can deliver a drug without inducing chronic localized inflammation to tissues (e.g., the peritoneal or vascular tissue) that have been injured mechanically or by reperfusion injury, whereby the biomaterial (e.g., coating or stand-alone film) and the therapeutic agent are ingested and metabolized by the cell, as it consumes the hydrolysis products of the biomaterial with the drug.

In various aspects, the biomaterial is a coating for a medical device, or a stand alone film. The biomaterial can be a fatty acid-based, pre-cure-derived biomaterial. In various embodiments, the fatty acid-based, pre-cure-derived biomaterial is non-polymeric. In certain instances, as described herein, the source of the fatty acid is an oil, e.g., a fish oil. In such an instance, the fatty acid-based, pre-cure-derived biomaterial can also be referred to as an "oil-based, pre-cure-derived biomaterial."

In a particular aspect, the invention provides a fatty acid-based, pre-cure-derived biomaterial (e.g., coating or stand-alone film) that contains a pre-cure component. As described herein, a "pre-cure" component refers to fatty acids (e.g., from fish oil) that are partially cured (using heat, UV, etc.) to induce an initial amount of fatty-acid oxidation and crosslinking to form a viscous fatty acid-derived gel. The pre-cure component can be dissolved in a solvent, and sprayed onto a device, e.g., a medical device. Once the pre-cure component is associated with a medical device, the device can be used for treatment in a subject, or it can be further exposed to additional curing conditions, which may result in a smooth, conformal coating referred to herein as a "fatty-acid based, pre-cure-derived biomaterial (coating)." The pre-cure and/or the fatty-acid based, pre-cure-derived biomaterial can be characterized as a gel.

The pre-cured fatty acid component (also referred to herein as "pre-cured fatty acid component," or simply "pre-cure;" when the source of the fatty acid is an oil, such as fish oil, it can also be referred to as "pre-cured oil") can be added to a therapeutic agent, wherein the therapeutic agent is optionally combined with an oil, and the resulting combination can be further cured, thereby further cross-linking the fatty acids of the oil, to provide a fatty-acid based, pre-cure derived biomaterial, meaning a portion of the fatty acid-based biomaterial was pre-cured before formulation, and then exposed to further curing in the presence of a therapeutic agent. In one embodiment, the fatty-acid based, pre-cure derived biomaterial has tailored drug release properties. When the resulting pre-cure-derived biomaterial is used as a coating for a medical device or as a stand-alone film, it may also be referred to herein as a "fatty-acid based, pre-cure-derived coating" or a "fatty-acid based, pre-cure-derived stand-alone film."

The process of creating a pre-cure (e.g., of a fish oil) has the advantage of creating an initial platform of oxidized fatty acid cross-links that will be hydrolyzed by human tissue. In some embodiments, portions of the pre-cure curing process can be done in the absence of the therapeutic agent, enabling addition of the agent later in the process. In such embodiments, the pre-cure process can be conducted at a temperature and/or over a time period that would otherwise have lead to degradation of a thermally/chemically sensitive therapeutic agent of interest (e.g., a rap amycin or cyclosporine derivative), except that the agent is not present for such portions of the pre-cure process. This process results in a partially cross-linked composition, with reduced oxidizable reactive sites (e.g., C=C bonds), that contains no therapeutic agent. After the pre-cure is formed, the therapeutic agent is then added, and optionally vitamin E is also added. The vitamin E component has the advantage of protecting the drug and pre-cured oil from further oxidation, but does not inhibit further cross-linking (e.g., esterification) of the fatty acid and/or glyceride components of the oil.

Accordingly, in various aspects, the present invention provides methods for producing a hydrophobic, crosslinked, pre-cure-derived biomaterial, wherein the pre-cure-derived biomaterial is utilized with one or more therapeutic agents, wherein the therapeutic agents have a controlled loading and are released in a sustained manner as the coating is absorbed. In various embodiments, provided are methods of tailoring the drug release profile of a pre-cure-derived biomaterial by control of the curing conditions used to produce the pre-cure-derived biomaterial (e.g., coating or stand-alone film) from an oil containing starting material, the use of a free radical scavenger in an oil containing starting material from which the pre-cure-derived biomaterial is formed, or combinations thereof. In various embodiments, the methods of the present invention tailor the drug release properties of a fatty-acid based, pre-cure-derived biomaterial (e.g., coating or stand-alone film) by controlling the degree of cross-linking of fatty acids. In various embodiments, the methods of the present invention tailor the drug delivery properties of a pre-cure-derived biomaterial (e.g., coating or stand-alone film) by controlling the level of fatty acids, tocopherols, lipid oxidation products, and soluble components in the fatty acid-based, pre-cure-derived biomaterial.

In various aspects, the present invention may provide fatty acid-derived biomaterials with a pre-cured oil component (e.g., coating or stand-alone film) comprising one or more therapeutic agents with a tailored release profile for one or more of the therapeutic agents. Such a material is referred to herein as a "fatty acid-based, pre-cure-derived biomaterial." In various embodiments, the tailored release profile comprises a sustained release profile. In various embodiments, the tailored release profile properties are controlled by the level of fatty acids, tocopherols, lipid oxidation products, and soluble components in the fatty acid-based, pre-cure-derived biomaterial. In various aspects of the present invention, the fatty acid-based, pre-cure-derived biomaterial contains fatty acids, many of which originate as triglycerides. It has previously been demonstrated that triglyceride byproducts, such as partially hydrolyzed triglycerides and fatty acid molecules can integrate into cellular membranes and enhance the solubility of drugs into cellular membranes (M. Cote, *J. of Controlled Release.* 2004, Vol. 97, pgs 269-281.; C. P. Burns et al., *Cancer Research.* 1979, Vol. 39, pgs 1726-1732; R. Beck et al., *Circ. Res.* 1998, Vol 83, pgs 923-931.; B. Henning et al. *Arterioscler. Thromb. Vasc. Biol.* 1984, Vol 4, pgs 489-797). Whole triglycerides are known not to enhance cellular uptake as well as a partially hydrolyzed triglyceride, because it is difficult for whole triglycerides to cross cell membranes due to their relatively larger molecular size. Vitamin E compounds can also integrate into cellular membranes resulting in decreased membrane fluidity and cellular uptake (P.P. Constantinides. *Pharmaceutical Research.* 2006; Vol. 23, No. 2, 243-255).

In various aspects, the present invention may provide a pre-cure-derived biomaterial (e.g., coating or stand-alone film) containing fatty acids, glycerides, lipid oxidation products and alpha-tocopherol in differing amounts and ratios to contribute to a fatty acid-based, pre-cure-derived biomaterial in a manner that provides control over the cellular uptake characteristics of the fatty acid-based, pre-cure-derived biomaterial and any therapeutic agents mixed therein.

In various aspects, the present invention may provide coated medical devices having a fatty acid-based, pre-cure-derived biomaterial drug release coating comprising one or more layers of said pre-cure-derived biomaterial, wherein at least one of the pre-cure-derived biomaterial layers contains one or more therapeutic agents. The coating can be a hydrophobic, cross-linked pre-cure-derived biomaterial (derived, e.g., from fish oil, making it an "oil-derived, pre-cure-derived biomaterial"). In various embodiments, the coating is non-polymeric. In various embodiments, the drug release coating hydrolyzes in vivo, into substantially non-inflammatory compounds. In various embodiments, the pre-cure-derived biomaterial is coated onto a medical device that is implantable in a patient to effect long term local delivery of the therapeutic agent to the patient. In various embodiments the delivery is at least partially characterized by the total and relative amounts of the therapeutic agent released over time. In various embodiments, the tailored delivery profile is controlled by the level of lipid oxidation, vitamin E and/or soluble components in the fatty acid-based, pre-cure-derived biomaterial. In various embodiments, the delivery profile is a function of the solubility and lipophilicity of the coating components and therapeutic agent in-vivo. The pre-cure-derived biomaterial can be a stand-alone film, gel, suspension, or emulsion that has the properties discussed above.

In various embodiments, the present invention may provide fatty-acid based, pre-cure-derived coatings where the drug release profile of the coating is tailored through the provision of two or more coatings and selection of the location of the therapeutic agent. The drug location can be altered, e.g., by coating a bare portion of a medical device with a first starting material and creating a first cured coating, then coating at least a portion of the first cured-coating with the drug-oil formulation to create a second overlayer coating. It is to be understood that the process of providing two layers can be extended to provide three or more layers, wherein at least one of the layers comprises a fatty acid-based, pre-cure-derived biomaterial. In addition, one or more of the layers can be drug releasing, and the drug release profile of such layers can be tailored using the methods described herein.

In accordance with various embodiments of the present invention, the pre-cure-derived biomaterial (e.g., coating or stand-alone film) contains lipids. The pre-cure-derived biomaterial can be formed from an oil, such as fish oil, starting material. The pre-cure-derived biomaterial (e.g., coating or stand-alone film) can contain saturated, unsaturated, or polyunsaturated fatty acids. When the fatty acid-based, pre-cure-derived biomaterial is cross-linked, it can contain omega-3 fatty acids. The fatty acid-based, pre-cure-derived biomaterial can also contain alpha-tocopherol, or vitamin E derivatives, and/or a therapeutic agent.

The coatings of the present invention can be formulated to contain a variety of other chemicals and entities in addition to a therapeutic agent, including, but not limited to, one or more of: a pharmaceutically acceptable carrier, an excipient, a surfactant, a binding agent, an adjuvant agent, and/or a stabilizing agent (including preservatives, buffers and antioxidants). In one embodiment, alpha-tocopherol TPGS may be added to the coatings of the present invention.

In various aspects, the present invention may provide methods for treating injury in a mammal, such as, e.g., a human. In various embodiments, the injury is a vascular injury. In various embodiments, the methods comprise locally administering one or more therapeutic agents in a therapeutically effective amount by sustained release of the one or more therapeutic agents from a coating comprising a fatty acid-based, pre-cure-derived biomaterial.

The teachings herein demonstrate that the cured coatings and stand-alone films that comprise a fatty acid-based, pre-cure-derived biomaterial provide the ability to regulate the release profile of drug-loaded fatty acid-based, pre-cure-derived biomaterials from the films or from implantable devices. In various embodiments, the release profile can be controlled through changes in oil chemistry by varying fatty acid-based, pre-cure-derived biomaterial (e.g., coating or stand-alone film) composition and cure times. The teachings demonstrate that the release of therapeutic compounds from pre-cure-derived biomaterials (e.g., coating or stand-alone film) can be modified based on altering the oil curing conditions, the oil starting material, length of curing, and amount of cross-linking. The teachings demonstrate that the cross-linking and gelation of the fatty-acid based, pre-cure-derived oil coatings and fatty-acid based, pre-cure-derived stand-alone films can be directly dependent on the formation of hydroperoxides in the oil component, which increases with increasing temperature and degree of unsaturation of the oil. Dissolution experiments have shown that drug release and coating degradation are more rapid for the cross-linked coatings produced using lower temperature curing conditions (e.g., around 150° F.) than higher temperature curing conditions (e.g., around 200° F.).

In another aspect, the invention provides a fatty-acid based, pre-cure-derived coating for a medical device, comprising a cross-linked fish oil. The fish oil can optionally include a therapeutic agent. The coating can be prepared according to the methods described herein, such that, when the coating does include a therapeutic agent, the coating releases the therapeutic agent at a desired release rate in vivo.

In another aspect, the invention provides a coating for a medical device, comprising a fatty acid and a therapeutic agent, wherein the fatty acid was partially cross-linked before association with the therapeutic agent. That is, the fatty acid was partially cured to induce an initial amount of fatty-acid cross-linking, and then combined with the therapeutic agent. The resulting composition can then be exposed to an additional curing procedure, e.g., after being applied to a medical device, thereby further cross-linking the fatty acids to form a coating. In one embodiment, the therapeutic agent is contained within the coating in such a manner that the therapeutic agent has an enhanced release profile. As used herein, the phrase "enhanced release profile" refers to the release profile of a therapeutic agent by a pre-cure-derived biomaterial that is prepared using the methods of the current invention. That is, as discussed herein, by preparing a pre-cure, adding a therapeutic agent to the pre-cure, and further curing the therapeutic agent-pre-cure composition, a therapeutic cross-linked biomaterial is created that will release the therapeutic agent in a manner different from a preparation that was not prepared according to the methods of the invention (i.e., a fatty acid-derived biomaterial that was not prepared with the use of a pre-cure composition).

For example, by first preparing a pre-cure in the absence of a therapeutic agent, the therapeutic agent is not exposed to process conditions that would otherwise lead to its degradation. The therapeutic agent can then be added to the pre-cure for further processing. Because of this preservation of the therapeutic agent structure, there is less degradation of the therapeutic agent during manufacturing of the coating. Accordingly, there exists a higher amount of therapeutic agent in the coating that can be released, especially compared to a coating that was prepared without a pre-cure (i.e., compared to a coating in which the uncured, fatty-acid containing material is first combined with a therapeutic agent, and then cured). Thus, the therapeutic agent's release profile is "enhanced."

In one embodiment, the coating of the invention further comprises a pre-cured glyceride. The coating can comprise 5-25% $C_{14}$ fatty acids and/or 5-30% $C_{16}$ fatty acids. The coating can be configured to produce a glyceride upon metabolization in-vivo. The coating can comprise approximately 30-90% saturated fatty acids; approximately 30-80% unsaturated fatty acids; a glyceride; one or more of the group consisting of a glyceride, a glycerol, and a fatty alcohol, any of which can be partially cross-linked; and/or vitamin E.

In another embodiment, the coating is associated with an implantable device. The coating can be associated with a medical device, and the medical device is a stent, a catheter, a surgical mesh, or a balloon.

In one embodiment, the therapeutic agent that is associated with the coating is an anti-proliferative drug, an anti-inflammatory agent, an antimicrobial agent or antibiotic agent. In another embodiment, the therapeutic agent is Compound A, Compound B, Compound C, Compound D, Compound E (as described below), a cyclosporine derivative or rapamycin derivative.

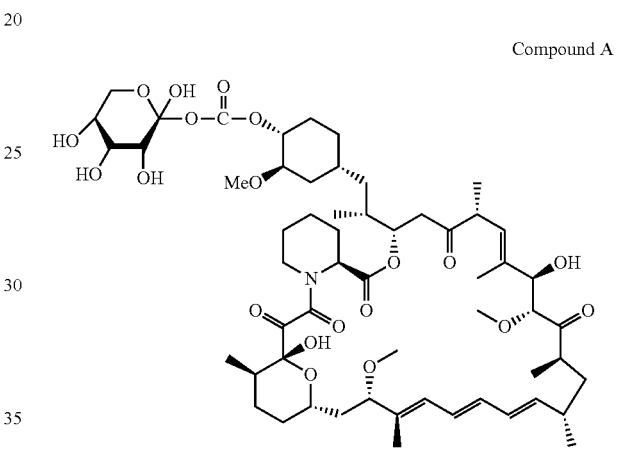

Compound A

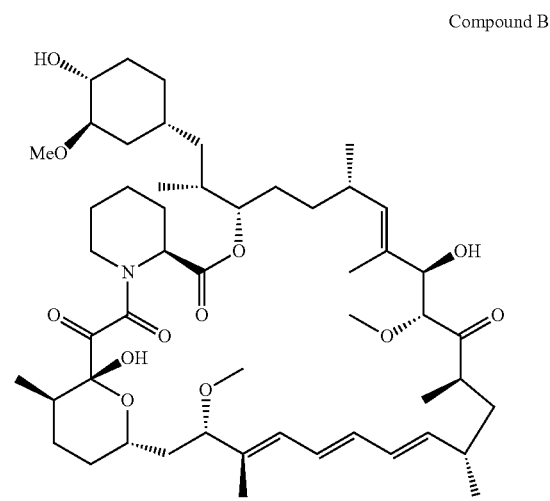

Compound B

-continued

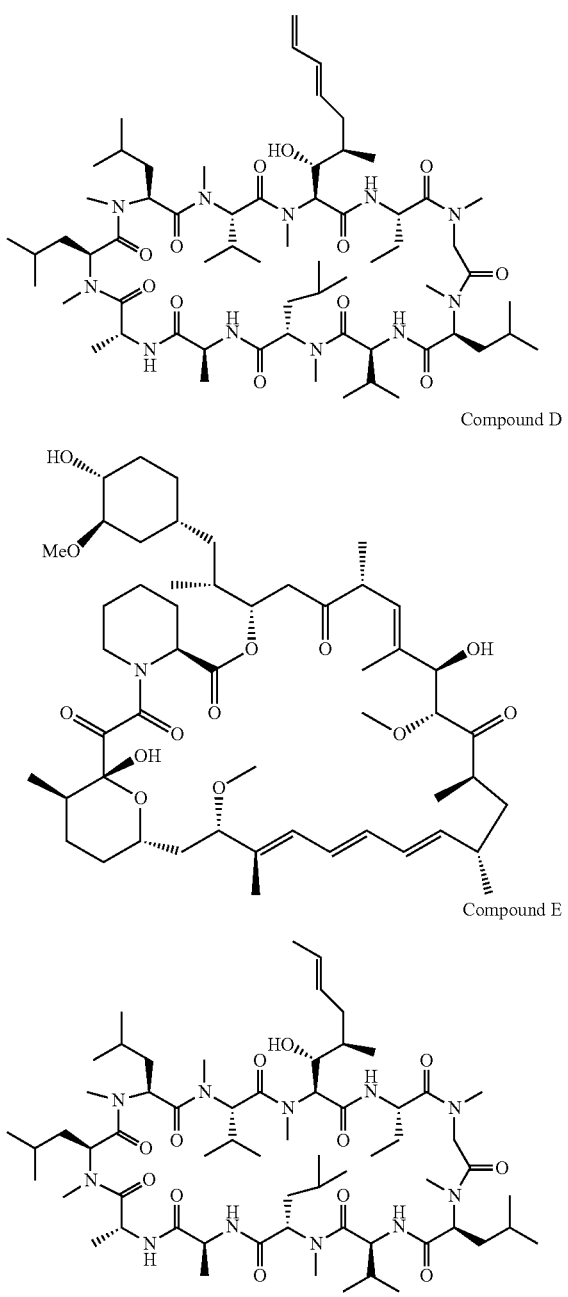

In another embodiment, the coating has a release profile of the therapeutic agent in 0.01 M phosphate buffered saline (PBS) out to about 5-20 days. The coating can release said therapeutic agent at a desired release rate in vivo. In one embodiment, the coating has a release profile of the therapeutic agent in 0.01 M phosphate buffered saline (PBS) out to more than 20 days.

In another embodiment, the coating comprises approximately 10-20% $C_{14}$ saturated fatty acids and approximately 25-50% $C_{16}$ saturated fatty acids. The coating can comprise lactone and ester cross links. The coating can contain disordered hydrocarbon chains as determined by infrared absorption and X-ray diffraction.

In another embodiment, the coating does not contain a cross-linking agent.

In still another embodiment, the coating hydrolyzes in vivo into fatty acids, glycerols, and glycerides; hydrolyzes in vivo into non-inflammatory components; and/or contains an amount of carboxylic acid groups sufficient to facilitate hydrolysis in vivo.

The coating can comprises approximately 50-90% saturated fatty acids; approximately 10-50% unsaturated fatty acids; a glyceride; and/or one or more of the group consisting of a glyceride, a glycerol, and a fatty alcohol, any of which can be partially cross-linked. In one embodiment, the source of the fatty acids is an oil, such as oil is a fish oil, olive oil, grape oil, palm oil, or flaxseed oil. In one embodiment, the source is a fish oil.

In another aspect, the invention provides a fatty-acid based, pre-cure-derived coating for a medical device, comprising: a pre-cured, cross-linked fatty acid, comprising approximately 5-50% $C_{16}$ fatty acids.

In still another aspect, the invention provides a fatty-acid based, pre-cure-derived coating for a medical device comprising a non-polymeric, cross-linked fatty acid, comprising approximately 5-25% $C_{14}$ fatty acids and 5-50% $C_{16}$ fatty acids.

In another aspect, the invention provides a fatty-acid based, pre-cure-derived coating for a medical device comprising cross-linked fatty acids and glycerides, wherein the fatty acids and glycerides have disordered alkyl groups, which cause the coating to be flexible and hydratable.

In yet another aspect, the invention provides a fatty-acid based, pre-cure-derived for a medical device comprising a fatty acid-derived biomaterial, wherein the fatty acid-derived biomaterial comprises delta-lactones.

In still another aspect, the invention provides a fatty-acid based, pre-cure-derived coating for a medical device, wherein the coating comprises lactone and ester cross links, as indicated by an infrared absorption spectrum having peaks at approximately 1740-1850 cm$^{-1}$, respectively.

In another aspect, the invention provides a fatty-acid based, pre-cure-derived coating for a medical device, comprising a cross-linked, fatty acid-derived biomaterial, wherein approximately 60-90% of the biomaterial is constituted by fatty acids with molecular weights below 500.

In yet another aspect, the invention provides a fatty-acid based, pre-cure-derived biomaterial suitable for achieving modulated healing in a tissue region in need thereof, wherein the biomaterial is administered in an amount sufficient to achieve said modulated healing, wherein the modulated healing comprises a modulation of platelet or fibrin deposition in or near said tissue region. In one embodiment, the tissue region is the vasculature of a subject.

In still another aspect, the invention provides a fatty-acid based, pre-cure-derived biomaterial suitable for achieving modulated healing at a site of vascular injury in need thereof, wherein the composition is administered in an amount sufficient to achieve said modulated healing, wherein the modulated healing comprises a modulation of at least one metric of organized tissue repair. In one embodiment, the vascular healing is the inflammatory stage of vascular healing. In another embodiment, the organized tissue repair comprises platelet or fibrin deposition at the site of vascular injury. In another embodiment, the modulation of at least one metric of organized tissue repair is a delay in the healing process at a site of vascular injury.

In another embodiment, the biomaterials of the invention are administered to the region in need thereof via a catheter, balloon, stent, surgical mesh, surgical dressing, or graft.

In another aspect, provided herein is a preparation for deriving a coating for a medical device, the preparation comprising:

a pre-cured cross-linked fatty acid oil, wherein the coating contains ester and lactone cross-links, and wherein a portion of the preparation comprises a pre-cured natural oil. The preparation can further comprise a therapeutic agent. The preparation has a viscosity of about $1.0 \times 10^5$ to about $1.0 \times 10^7$ cps. The preparation can be further dissolved in an organic solvent.

Also provided herein is a method for producing a fatty-acid based, pre-cure-derived coating for a medical device, wherein the method comprises:

curing an oil-containing starting material according to a first curing condition to form a second material;

combining a therapeutic agent with the second material to form a third material;

and curing the third material such that a coating is produced.

In one embodiment of the method, the therapeutic agent is combined with an oil-containing material or organic solvent before combining with the second material. In another embodiment, the curing temperature of the first curing condition and/or total curing duration exceed the degradation temperature of the therapeutic agent. In still another embodiment, the first curing condition results in appreciable formation of esters and lactones in the oil such that substantial cross linking of fatty acids occurs during the second curing condition. In still another embodiment, the curing temperature and duration is adjusted to tailor the release profile of the therapeutic agent. Vitamin E can be added to the second material. In another embodiment, the third material is combined with an organic solvent, and applied to a medical device before curing to form a conformal coating. The third material can then be sprayed on a medical device before curing to form a coating, e.g., a non-conformal coating. In another embodiment of the method, the oil-containing starting material is fish oil. In still another embodiment of the method, the medical device is a stent, a catheter, a surgical mesh or a balloon.

The second material produced by the method can have a viscosity of about $1.0 \times 10^5$ to about $1.0 \times 10^7$ cps.

The therapeutic agent used in the method can be an anti-proliferative drug or an anti-inflammatory agent. The therapeutic agent used in the method can also be Compound A, Compound B, Compound C, Compound D, Compound E, a cyclosporine derivative or rapamycin derivative.

In another embodiment of the method, the first curing condition is tailored such that the second material, when applied to a medical device, provides a non-conformal coating on the medical device; and wherein the second curing condition is tailored such that the third material, when applied to a coating, provides a conformal coating. In another embodiment, the curing time for the first curing condition can be substantially increased in order to reduce the curing time required for the second curing condition to obtain desired mechanical properties of the final coating. In another embodiment, the first curing condition can be substantially increased in order to reduce the curing time required for the second curing condition to obtain desired mechanical properties and preserve a thermally sensitive drug to the final coating.

In another aspect, provided herein is a fatty-acid based, pre-cure-derived coating for a medical device, wherein said coating comprises: a hydrophobic, non-polymeric cross-linked fish oil; and a therapeutic agent; wherein the coating can withstand 16-22 psi of compressive force.

In still another aspect, provided herein is a fatty-acid based, pre-cure-derived medical device coating, that hydrolyzes in vivo into fatty acids, glycerols, and glycerides.

In yet another aspect, provided herein is a fatty-acid based, pre-cure-derived coating for a medical device, comprising: a non-polymeric, partially cross-linked fatty acid, and a therapeutic agent, wherein the therapeutic agent is contained within the coating in such a manner that the therapeutic agent has an enhanced release profile.

In another aspect, provided herein is a preparation for deriving a coating for a medical device, the preparation comprising: a non-polymeric, partially cross-linked fatty acid, and a therapeutic agent, wherein the coating contains ester and lactone cross-links.

In still another aspect, provided herein is a fatty-acid based, pre-cure-derived coating for a medical device, comprising: a cross-linked fatty acid oil, and a therapeutic agent; wherein the coating is prepared by curing a natural oil-containing starting material to induce cross-linking of a portion of the fatty acids; adding a therapeutic agent to the partially-cross linked fatty acid oil to form a therapeutic agent-oil composition; and curing the therapeutic agent-oil composition to induce additional cross links in the fatty acids, such that the coating is formed. In one embodiment of the coating, the therapeutic agent is combined with a natural oil-containing material, organic solvent and/or vitamin E before combining with the partially-cross linked fatty acid oil. In another embodiment, the therapeutic agent is combined with vitamin E before combining with the partially-cross linked fatty acid oil, such that the therapeutic agent has an enhanced release profile.

In another aspect, provided herein is a stand-alone film comprising a pre-cured fatty acid. The stand-alone film can comprise approximately 5-50% $C_{16}$ fatty acids; 5-25% $C_{14}$ fatty acids, 5-40% $C_{16}$ fatty acids; and/or vitamin E. The film can be bioabsorbable, and/or maintain anti-adhesive properties. The stand-alone film can further comprise a therapeutic agent, such as Compound A, Compound B, Compound C, Compound D, Compound E, a cyclosporine derivative or rapamycin derivative. The therapeutic agent can be combined with the fatty acid compound prior to formation of the film, resulting in the therapeutic agent being interspersed throughout the film.

In another aspect, provided herein is a stand-alone film, comprising:

a cross-linked fatty acid oil, and a therapeutic agent;

wherein the stand-alone film is prepared by curing a natural oil-containing starting material to induce cross-linking of a portion of the fatty acids;

adding a therapeutic agent to the partially-cross linked fatty acid oil to form a therapeutic agent-oil composition; and curing the therapeutic agent-oil composition to induce additional cross links in the fatty acids, such that the stand-alone film is formed.

In another aspect, provided herein is a fatty-acid based, pre-cure-derived biomaterial comprising a partially cross-linked fatty acid and a therapeutic agent, wherein the therapeutic agent comprises at least 40%, by weight, of the biomaterial composition. In another embodiment, the therapeutic agent comprises at least 50%, by weight, of the biomaterial composition.

BRIEF DESCRIPTION OF THE DRAWINGS

The foregoing and other aspects, embodiments, objects, features and advantages of the invention can be more fully understood from the following description in conjunction with the accompanying drawings. In the drawings, like reference characters generally refer to like features and structural elements throughout the various figures. The drawings are not necessarily to scale, emphasis instead being placed upon illustrating the principles of the invention.

FIG. 4 shows a summary of pre-cured-derived biomaterial reaction chemistry;

FIG. 5 is a schematic of reactions of oils that result in the formation of ester groups;

FIG. 7 shows bar graphs showing similarity of fatty acid composition between fatty-acid based, pre-cure-derived biomaterial coating and biological tissue;

FIG. 8 is a flow chart illustrating a method of making the coated medical device of the present invention, in accordance with one embodiment of the present invention;

FIG. 9 is a flow chart illustrating a variation of the method of FIG. 8, in accordance with one embodiment of the present invention;

FIG. 19 shows the viscosity of the pre-cure-derived biomaterial described in Example 6A;

FIGS. 20A and 20B are SEMs of stents coated with a pre-cure-derived biomaterial;

DETAILED DESCRIPTION

Figure 1:
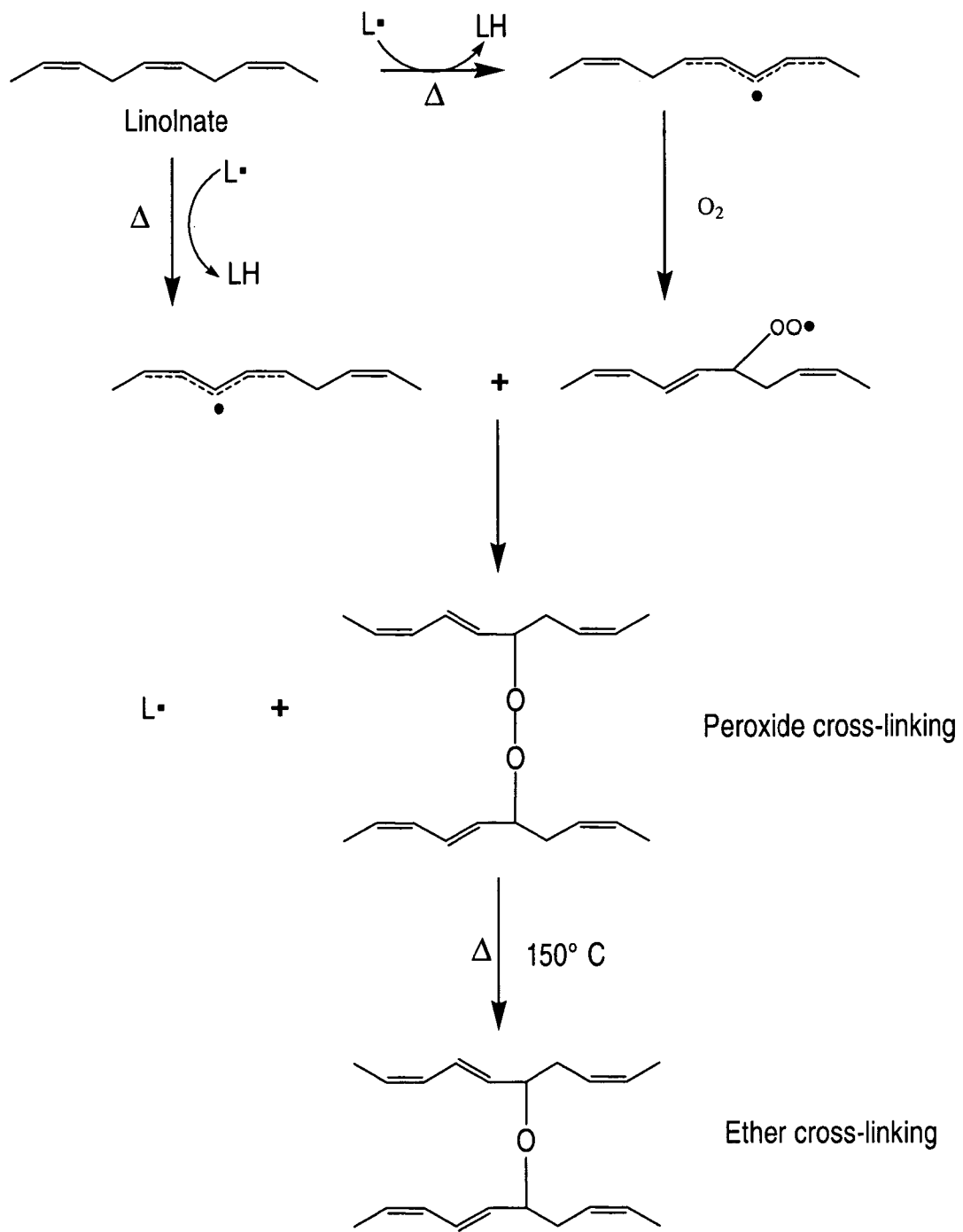
FIG. 1 is a schematic illustration of an example of the creation of peroxide and ether cross-linking in a polyunsaturated oil.

The present invention is directed toward the formation of a fatty-acid based, pre-cure-derived biomaterial that can be utilized alone or in combination with a medical device for the release and local delivery of one or more therapeutic agents, methods of forming and tailoring the properties of said coatings and methods of using said coatings for treating injury in a mammal. Additionally, due to the unique properties of the underlying chemistry of the biomaterial, it will be demonstrated that the coating contains specific chemical components that assist in reducing a foreign body response and inflammation at the site of tissue injury during implantation that improves its in-vivo performance. The fatty-acid based, pre-cure-derived biomaterial can be formed from a pre-cure, e.g., a pre-cured fatty acid.

Prior to further describing the invention, it may be helpful to generally and briefly describe injury and the biological response thereto.

Vascular Injury

Vascular injury causing intimal thickening can be broadly categorized as being either biologically or mechanically induced. Biologically mediated vascular injury includes, but is not limited to, injury attributed to infectious disorders including endotoxins and herpes viruses, such as cytomegalovirus; metabolic disorders, such as atherosclerosis; and vascular injury resulting from hypothermia, and irradiation. Mechanically mediated vascular injury includes, but is not limited to, vascular injury caused by catheterization procedures or vascular scraping procedures, such as percutaneous transluminal coronary angioplasty; vascular surgery; transplantation surgery; laser treatment; and other invasive procedures which disrupt the integrity of the vascular intima or endothelium. Generally, neointima formation is a healing response to a vascular injury.

Inflammatory Response

Wound healing upon vascular injury occurs in several stages. The first stage is the inflammatory phase. The inflammatory phase is characterized by hemostasis and inflammation. Collagen exposed during wound formation activates the clotting cascade (both the intrinsic and extrinsic pathways), initiating the inflammatory phase. After injury to tissue occurs, the cell membranes, damaged from the wound formation, release thromboxane A2 and prostaglandin 2-alpha, which are potent vasoconstrictors. This initial response helps to limit hemorrhage. After a short period, capillary vasodilatation occurs secondary to local histamine release, and the cells of inflammation are able to migrate to the wound bed. The timeline for cell migration in a normal wound healing process is predictable. Platelets, the first response cell, release multiple chemokines, including epidermal growth factor (EGF), fibronectin, fibrinogen, histamine, platelet-derived growth factor (PDGF), serotonin, and von Willebrand factor. These factors help stabilize the wound through clot formation. These mediators act to control bleeding and limit the extent of injury. Platelet degranulation also activates the complement cascade, specifically C5a, which is a potent chemoattractant for neutrophils.

As the inflammatory phase continues, more immune response cells migrate to the wound. The second response cell to migrate to the wound, the neutrophil, is responsible for debris scavenging, complement-mediated opsonization of bacteria, and bacteria destruction via oxidative burst mechanisms (i.e., superoxide and hydrogen peroxide formation). The neutrophils kill bacteria and decontaminate the wound from foreign debris.

The next cells present in the wound are the leukocytes and the macrophages (monocytes). The macrophage, referred to as the orchestrator, is essential for wound healing. Numerous enzymes and cytokines are secreted by the macrophage. These include collagenases, which debride the wound; interleukins and tumor necrosis factor (TNF), which stimulate fibroblasts (produce collagen) and promote angiogenesis; and transforming growth factor (TGF), which stimulates keratinocytes. This step marks the transition into the process of tissue reconstruction, i.e., the proliferative phase.

Cell Proliferation

The second stage of wound healing is the proliferative phase.

Epithelialization, angiogenesis, granulation tissue formation, and collagen deposition are the principal steps in this anabolic portion of wound healing. Epithelialization occurs early in wound repair. At the edges of wounds, the epidermis immediately begins thickening. Marginal basal cells begin to migrate across the wound along fibrin strands stopping when they contact each other (contact inhibition). Within the first 48 hours after injury, the entire wound is epithelialized. Layering of epithelialization is re-established. The depths of the wound at this point contain inflammatory cells and fibrin strands. Aging effects are important in wound healing as many, if not most, problem wounds occur in an older population. For example, cells from older patients are less likely to proliferate and have shorter life spans and cells from older patients are less responsive to cytokines.

Heart disease can be caused by a partial vascular occlusion of the blood vessels that supply the heart, which is preceded by intimal smooth muscle cell hyperplasia. The underlying cause of the intimal smooth muscle cell hyperplasia is vascular smooth muscle injury and disruption of the integrity of the endothelial lining. Intimal thickening following arterial injury can be divided into three sequential steps: 1) initiation of smooth muscle cell proliferation following vascular injury, 2) smooth muscle cell migration to the intima, and 3) further proliferation of smooth muscle cells in the intima with deposition of matrix. Investigations of the pathogenesis of intimal thickening have shown that, following arterial injury, platelets, endothelial cells, macrophages and smooth muscle cells release paracrine and autocrine growth factors (such as platelet derived growth factor, epidermal growth factor, insulin-like growth factor, and transforming growth factor) and cytokines that result in the smooth muscle cell proliferation and migration. T-cells and macrophages also migrate into the neointima. This cascade of events is not limited to arterial injury, but also occurs following injury to veins and arterioles.

Granulomatous Inflammation

Chronic inflammation, or granulomatous inflammation, can cause further complications during the healing of vascular injury. Granulomas are aggregates of particular types of chronic inflamatory cells which form nodules in the millimeter size range. Granulomas may be confluent, forming larger areas. Essential components of a granuloma are collections of modified macrophages, termed epithelioid cells, usually with a surrounding zone of lymphocytes. Epithelioid cells are so named by tradition because of their histological resemblance to epithelial cells, but are not in fact epithelial; they are derived from blood monocytes, like all macrophages. Epithelioid cells are less phagocytic than other macrophages and appear to be modified for secretory functions. The full extent of their functions is still unclear.

Macrophages in granulomas are commonly further modified to form multinucleate giant cells. These arise by fusion of epithelioid macrophages without nuclear or cellular division forming huge single cells which may contain dozens of nuclei. In some circumstances the nuclei are arranged round the periphery of the cell, termed a Langhans-type giant cell; in other circumstances the nuclei are randomly scattered throughout the cytoplasm (i.e., the foreign body type of giant cell which is formed in response to the presence of other indigestible foreign material in the tissue). Areas of granulomatous inflammation commonly undergo necrosis.

Formation of granulomatous inflammation seems to require the presence of indigestible foreign material (derived from bacteria or other sources) and/or a cell-mediated immune reaction against the injurious agent (type IV hypersensitivity reaction).

Drug Eluting, Fatty-Acid Based, Pre-Cure-Derived Biomaterials: Coatings and Stand-Alone Films The fatty-acid based, pre-cure-derived biomaterials (e.g., coatings and stand-alone films) of the present invention comprise a hydrophobic cross-linked fatty acid-derived biomaterial and optionally one or more therapeutic agents contained in the fatty-acid based, pre-cure-derived biomaterial. In addition, the pre-cure-derived biomaterials (e.g., coatings and stand-alone films) of the present invention are bio-absorbable as described herein. The therapeutic agent can be an active agent as contained in the coating and/or a prodrug that, e.g., becomes active once released from the coating. In one embodiment of the invention, the drug eluting pre-cure-derived biomaterial comprised of a cross-linked fatty acid, e.g., an omega-3 fatty acid. The cross-linked fatty acid can be non-polymeric. The source of the omega-3 fatty acid can be a naturally occurring oil, e.g., a fish oil.

The hydrophobic pre-cure-derived pre-cure biomaterial coatings and stand-alone films of the present invention may be formed from an oil component. The oil component can be either an oil, or an oil composition. The oil component can be a synthetic oil, or a naturally occurring oil, such as fish oil, cod liver oil, flaxseed oil, grape seed oil, or other oils having desired characteristics. One embodiment of the present invention makes use of a fish oil in part because of the high content of omega-3 fatty acids. The fish oil can also serve as an anti-adhesion agent. In addition, the fish oil maintains anti-inflammatory or non-inflammatory properties as well. The present invention is not limited to formation of the pre-cure-derived biomaterials with fish oil as the oil starting material. However, the following description makes reference to the use of fish oil as one example embodiment. Other naturally occurring oils can be utilized in accordance with the present invention as described herein.

It should be noted that as utilized herein, the term fish oil fatty acid includes, but is not limited to, omega-3 fatty acid, oil fatty acid, free fatty acid, monoglycerides, di-glycerides, or triglycerides, esters of fatty acids, or a combination thereof. The fish oil fatty acid includes one or more of arachidic acid, gadoleic acid, arachidonic acid, eicosapentaenoic acid, docosahexaenoic acid or derivatives, analogs and pharmaceuticlly acceptable salts thereof.

Furthermore, as utilized herein, the term free fatty acid includes but is not limited to one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof. The naturally occurring oils, including fish oil, are cured as described herein to form a hydrophobic cross-linked fatty acid-derived pre-cure biomaterial, creating the coating.

The present invention relates to a bio-absorbable medical device coatings and stand-alone films that can exhibit anti-inflammatory properties, non-inflammatory properties, and anti-adhesion properties, and the corresponding method of making. The stand-alone film is generally formed of a naturally occurring oil, such as a fish oil. In addition, the oil composition can include a therapeutic agent component, such as a drug or other bioactive agent. The stand-alone film is implantable in a patient for short term or long term applications. As implemented herein, the stand-alone film is a fatty-acid based, pre-cure-derived biomaterial derived at least in part from a fatty acid compound, wherein the stand-alone film is prepared in accordance with the methods of the invention. In accordance with further aspects of the present invention, the stand-alone film can further include a vitamin E compound forming a portion of the fatty acid compound.

In accordance with further aspects of the present invention, the stand-alone film further includes a therapeutic agent. The therapeutic agent can include an agent selected from the group consisting of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

In accordance with further aspects of the present invention, the therapeutic agent is combined with the fatty acid compound prior to formation of the film, resulting in the therapeutic agent being interspersed throughout the film. Alternatively, the therapeutic agent is applied to the film in the form of a coating. In accordance with further aspects of the present invention, the stand-alone film is bioabsorbable. The stand-alone film can further maintain anti-adhesive properties.

In accordance with still another embodiment of the present invention, a method of forming a stand-alone film is introduced. The method includes providing a fatty acid compound in liquid form and applying the fatty acid compound to a substrate. The method also includes curing the fatty acid compound to form the stand-alone film. In accordance with one aspect of the present invention, the substrate includes expanded polytetrafluoroethylene (ePTFE) or polytetrafluoroethylene (PTFE). In accordance with further aspects of the present invention, the curing includes using at least one curing method selected from a group of curing methods including application of UV light and application of heat. The UV light can also be applied to set the fatty acid compound by forming a skin on the top surface of the fatty acid compound in liquid form prior to additional curing. In accordance with further aspects of the present invention, the substrate has an indentation that is used as a mold to shape the stand-alone film. Alternatively, the method can further include the step of cutting the film to a desirable shape.

The stand-alone film of the present invention may be used as a barrier to keep tissues separated to avoid adhesion. Application examples for adhesion prevention include abdominal surgeries, spinal repair, orthopedic surgeries, tendon and ligament repairs, gynecological and pelvic surgeries, and nerve repair applications. The stand-alone film may be applied over the trauma site or wrapped around the tissue or organ to limit adhesion formation. The addition of therapeutic agents to the stand-alone films used in these adhesion prevention applications can be utilized for additional beneficial effects, such as pain relief or infection minimization. Other surgical applications of the stand-alone film may include using a stand-alone film as a dura patch, buttressing material, internal wound care (such as a graft anastomotic site), and internal drug delivery system. The stand-alone film may also be used in applications in transdermal, wound healing, and non-surgical fields. The stand-alone film may be used in external wound care, such as a treatment for burns or skin ulcers. The stand-alone film may be used without any therapeutic agent as a clean, non-permeable, non-adhesive, non-inflammatory, anti-inflammatory dressing, or the stand-alone film may be used with one or more therapeutic agents for additional beneficial effects. The stand-alone film may also be used as a transdermal drug delivery patch when the stand-alone film is loaded or coated with one or more therapeutic agents.

Oils

With regard to the aforementioned oils, it is generally known that the greater the degree of unsaturation in the fatty acids the lower the melting point of a fat, and the longer the hydrocarbon chain the higher the melting point of the fat. A polyunsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, polyunsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Under the convention of naming the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both monounsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

As utilized herein, the term "bio-absorbable" generally refers to having the property or characteristic of being able to penetrate the tissue of a patient's body. In certain embodiments of the present invention bio-absorption occurs through a lipophilic mechanism. The bio-absorbable substance can be soluble in the phospholipid bi-layer of cells of body tissue, and therefore impact how the bio-absorbable substance penetrates into the cells.

It should be noted that a bio-absorbable substance is different from a biodegradable substance. Biodegradable is generally defined as capable of being decomposed by biological agents, or capable of being broken down by microorganisms or biological processes. Biodegradable substances can cause inflammatory response due to either the parent substance or those formed during breakdown, and they may or may not be absorbed by tissues. Because the materials of the invention are biocompatible, and they hydrolyze into non-inflammatory components, and are subsequently bio-absorbed by surrounding tissue, they are referred to as "biomaterials."

Drug Delivery

The pre-cure-derived biomaterials (e.g, coatings and stand-alone films) of the present invention deliver one or more therapeutic agents locally to a targeted area using a stand-alone film, medical device or apparatus bearing the coating at a selected targeted tissue location of the patient that requires treatment. The therapeutic agent is released from the biomaterial to the targeted tissue location. The local delivery of a therapeutic agent enables a more concentrated and higher quantity of therapeutic agent to be delivered directly at the targeted tissue location, without having broader systemic side effects. With local delivery, the therapeutic agent that escapes the targeted tissue location dilutes as it travels to the remainder of the patient's body, substantially reducing or eliminating systemic side effects.

Targeted local therapeutic agent delivery using a fatty-acid based, pre-cure-derived biomaterial (e.g, coatings and stand-alone films) can be further broken into two categories, namely, short term and long term. The short term delivery of a therapeutic agent occurs generally within a matter of seconds or minutes to a few days or weeks. The long term delivery of a therapeutic agent occurs generally within weeks to months.

The phrase "sustained release" as used herein generally refers to the release of a biologically active agent that results in the long term delivery of the active agent.

The phrase "controlled release" as used herein generally refers to the release of a biologically active agent in a substantially predictable manner over the time period of weeks or months, as desired and predetermined upon formation of the biologically active agent on the medical device from which it is being released. Controlled release includes the provision of an initial burst of release upon implantation, followed by the substantially predictable release over the aforementioned time period.

Drug Release Mechanisms

Prior attempts to create films and drug delivery platforms, such as in the field of stents, primarily make use of high molecular weight synthetic polymer based materials to provide the ability to better control the release of the therapeutic agent. Essentially, the polymer in the platform releases the drug or agent at a predetermined rate once implanted at a location within the patient. Regardless of how much of the therapeutic agent would be most beneficial to the damaged tissue, the polymer releases the therapeutic agent based on properties of the polymer, e.g., diffusion in a biostable polymer and bulk erosion in a biodegradable polymeric material. Accordingly, the effect of the therapeutic agent is substantially local at the surface of the tissue making contact with the medical device having the coating. In some instances the effect of the therapeutic agent is further localized to the specific locations of, for example, stent struts or mesh pressed against the tissue location being treated. High concentrations of therapeutic agent present in tissue adjacent to a polymer that elicits an inflammatory response can create the potential for a localized toxic effect.

In various embodiments of the present invention, the fatty-acid based, pre-cure-derived biomaterial of the invention (e.g., coatings and stand-alone films) release one or more therapeutic agents by a dissolution mechanism, e.g., dissolution of a therapeutic agent contained in a soluble component of the coating into the medium in contact with the coating, (e.g., tissue), in addition to an erosion based release mechanism. As a result, the drug release mechanism can be based on the solubility of the therapeutic agent in the surrounding medium. For example, a therapeutic agent near the interface between the hydrophobic coating and the surrounding medium can experience a chemical potential gradient that can motivate the therapeutic agent out of the oil based coating and into solution in the surrounding medium. Accordingly, in various embodiments, the release of a therapeutic agent is not rate-limited by the break-down or bulk erosion of the coating.

In various embodiments, the break-down products of the fatty-acid based, pre-cure-derived biomaterial of the invention are non-inflammatory byproducts, e.g., free fatty acids and glycerides, that themselves can release one or more of the therapeutic agents via a dissolution mechanism.

In various embodiments, the fatty-acid based, pre-cure derived biomaterial breaks-down according to a controlled surface erosion mechanism, thereby releasing one or more therapeutic agents to the surrounding medium, e.g., tissue, via a dissolution mechanism.

Therapeutic Agents

As utilized herein, the phrase "therapeutic agent(s)" refers to a number of different drugs or agents available, as well as future agents that may be beneficial for use with the fatty acid-derived, pre-cured biomaterials (e.g., coatings and stand-alone films) of the present invention. The therapeutic agent component can take a number of different forms including anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, anti-septics, analgesics, prodrugs thereof, and any additional desired therapeutic agents such as those listed in Table 1 below.

TABLE 1

| CLASS | EXAMPLES |
|---|---|
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |
| Antiplatelet Agents | Aspirin, dipyridamole, ticlopidine, clopidogrel, GP IIb/IIIa inhibitors, abcximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine, mTOR targeting compounds |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibition of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma -1b, Interluekin - 10 |
| Immunosuppressive/ Immunomodulatory Agents | Cyclosporine, rapamycin, mycophenolate motefil, leflunomide, tacrolimus, tranilast, interferon gamma-1b, mizoribine, mTOR targeting compounds |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative (for example, as described in U.S. Pat. No. 7,160,867), a rapamycin derivative (for example, as described in U.S. Pat. No. 6,200,985), everolimus, seco-rapamycin, seco-everolimus, and simvastatin. With systemic administration, the therapeutic agent is administered orally or intravenously to be systemically processed by the patient. However, there are drawbacks to a systemic delivery of a therapeutic agent, one of which is that the therapeutic agent travels to all portions of the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

The term "mTOR targeting compound" refers to any compound that modulates mTOR directly or indirectly. An example of an "mTOR targeting compound" is a compound that binds to FKBP 12 to form, e.g., a complex, which in turn inhibits phosphoinostide (PI)-3 kinase, that is, mTOR. In various embodiments, mTOR targeting compounds inhibit mTOR. Suitable mTOR targeting compounds include, for example, rapamycin and its derivatives, analogs, prodrugs, esters and pharmaceutically acceptable salts.

Calcineurin is a serine/threonine phospho-protein phosphatase and is composed of a catalytic (calcineurin A) and regulatory (calcineurin B) subunit (about 60 and about 18 kDa, respectively). In mammals, three distinct genes (A-alpha, A-beta, A-gamma) for the catalytic subunit have been characterized, each of which can undergo alternative splicing to yield additional variants. Although mRNA for all three genes appears to be expressed in most tissues, two isoforms (A-alpha and A-beta) are most predominant in brain.

The calcineurin signaling pathway is involved in immune response as well as apoptosis induction by glutamate excitotoxicity in neuronal cells. Low enzymatic levels of calcineurin have been associated with Alzheimers disease. In the heart or in the brain calcineurin also plays a key role in the stress response after hypoxia or ischemia.

Substances that are able to block the calcineurin signal pathway can be suitable therapeutic agents for the present invention. Examples of such therapeutic agents include, but are not limited to, FK506, tacrolimus, cyclosporin and include derivatives, analogs, esters, prodrugs, pharmaceutically acceptably salts thereof, and conjugates thereof which have or whose metabolic products have the same mechanism of action. Further examples of cyclosporin derivatives include, but are not limited to, naturally occurring and non-natural cyclosporins prepared by total- or semi-synthetic means or by the application of modified culture techniques. The class comprising cyclosporins includes, for example, the naturally occurring Cyclosporins A through Z, as well as various non-natural cyclosporin derivatives, artificial or synthetic cyclosporin derivatives. Artificial or synthetic cyclosporins can include dihydrocyclosporins, derivatized cyclosporins, and cyclosporins in which variant amino acids are incorporated at specific positions within the peptide sequence, for example, dihydro-cyclosporin D.

In various embodiments, the therapeutic agent comprises one or more of a mTOR targeting compound and a calcineurin inhibitor. In various embodiments, the mTOR targeting compound is a rapamycin or a derivative, analog, ester, prodrug, pharmaceutically acceptably salts thereof, or conjugate thereof which has or whose metabolic products have the same mechanism of action. In various embodiments, the calcineurin inhibitor is a compound of Tacrolimus, or a derivative, analog, ester, prodrug, pharmaceutically acceptably salts thereof, or conjugate thereof which has or whose metabolic products have the same mechanism of action or a compound of Cyclosporin or a derivative, analog, ester, prodrug, pharmaceutically acceptably salts thereof, or conjugate thereof which has or whose metabolic products have the same mechanism of action.

The therapeutic agents that can be used with the fatty acid-derived, pre-cured biomaterials of the invention can also include antimicrobial agents, including antivirals antibiotics, antifungals and antiparasitics. Specific antimicrobial agents that can be used with the fatty acid-derived, pre-cured biomaterials of the invention include Penicillin G, ephalothin, Ampicillin, Amoxicillin, Augmentin, Aztreonam, Imipenem, Streptomycin, Gentamicin, Vancomycin, Clindamycin, Erythromycin, Azithromycin, Polymyxin, Bacitracin, Amphotericin, Nystatin, Rifampicin, Tetracycline, Doxycycline, Chloramphenicol, Nalidixic acid, Ciprofloxacin, Sulfanilamide, Gantrisin, Trimethoprim Isoniazid (INH), para-aminosalicylic acid (PAS), and Gentamicin.

Therapeutically Effective Amounts and Dosage Levels

A therapeutically effective amount refers to that amount of a compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective amount refers to that ingredient alone. When applied to a combination, a therapeutically effective amount can refer to combined amounts of the active ingredients that result in the therapeutic effect, whether administered in combination, serially or simultaneously. In various embodiments, where formulations comprise two or more therapeutic agents, such formulations can be described as a therapeutically effective amount of compound A for indication A and a therapeutically effective amount of compound B for indication B, such descriptions refer to amounts of A that have a therapeutic effect for indication A, but not necessarily indication B, and amounts of B that have a therapeutic effect for indication B, but not necessarily indication A.

Actual dosage levels of the active ingredients in a fattyacid based, pre-cure-derived biomaterial (e.g., coating and stand-alone film) of the present invention may be varied so as to obtain an amount of the active ingredients which is effective to achieve the desired therapeutic response without being unacceptably toxic. The selected dosage level will depend upon a variety of pharmacokinetic factors including the activity of the particular therapeutic agent (drug) employed, or the ester, salt or amide thereof, the mechanism of drug action, the time of administration, the drug release profile of the coating, the rate of excretion of the particular compounds being employed, the duration of the treatment, other drugs, compounds and/or materials used in combination with the particular compounds employed, and like factors known in the medical arts. For example, the invention provides a fatty-acid based, pre-cure-derived biomaterial comprising a partially cross-linked fatty acid and a therapeutic agent, wherein the therapeutic agent comprises at least 30%, e.g., at least 40%, e.g., at least 50%, e.g., at least 60%, e.g., at least 70%, by weight, of the biomaterial composition. In addition to the therapeutic agent, the biomaterial can include vitamin E in addition to the therapeutic agent.

Other Agents

The pre-cure-derived biomaterials (e.g., coatings and stand-alone films) of the present invention may also comprise one or more other chemicals and entities in addition to the therapeutic agent, including, but not limited to, one or more of: a pharmaceutically acceptable carrier, an excipient, a surfactant, a binding agent, an adjuvant agent, and/or a stabilizing agent (including preservatives, buffers and antioxidants). The other agents can perform one or more functions, such as, e.g., an adjuvant may also serve as a stabilizing agent.

In various embodiments, the coatings and stand-alone films of the present invention include one or more of a free radical scavenger and uptake enhancer. In various embodiments, the coatings and stand-alone films comprise vitamin E.

It should be noted that as utilized herein to describe the present invention, the term vitamin E and the term alpha-tocopherol, are intended to refer to the same or substantially similar substance, such that they are interchangeable and the use of one includes an implicit reference to both. Further included in association with the term vitamin E are such variations including but not limited to one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha-tocopherol can be used alone or in combination to provide an effective transport of a given compound to a given region or location. Both fatty acids and alpha-tocopherol can be included in the fatty acid-derived, pre-cured biomaterials (e.g., coatings and stand-alone films) of the present invention described herein. Accordingly, fatty acids and alpha-tocopherol can be combined in differing amounts and ratios to contribute to an fatty acid-derived, pre-cured biomaterial (e.g., coating and stand-alone film) in a manner that provides control over the cellular uptake characteristics of the coating and any therapeutic agents mixed therein.

For example, the amount of alpha-tocopherol can be varied in the coating. Alpha-tocopherol is known to slow autoxidation in fish oil by reducing hydroperoxide formation, which results in a decrease in the amount of cross-linking in a cured fatty acid-derived, pre-cured biomaterial. In addition, alpha-tocopherol can be used to increase solubility of drugs in the oil forming the coating. In various embodiments, alpha-tocopherol can actually protect the therapeutic drug during curing, which increases the resulting drug load in the coating after curing. Furthermore, with certain therapeutic drugs, the increase of alpha-tocopherol in the coating can serve to slow and extend drug release due to the increased solubility of the drug in the alpha-tocopherol component of the coating. This reflects the cellular uptake inhibitor functionality of alpha-tocopherol, in that the uptake of the drug is slowed and extended over time.

Curing and the Formation of Pre-Cures and Fatty-Acid-Based, Pre-Cure Derived Biomaterials Several methods are available to cure the oil starting material to form the pre-cure, and then to cure the pre-cure (optionally containing one or more therapeutic agents) to produce a fatty-acid-based, pre-cure-derived biomaterial for a drug release and delivery coating or stand-alone film in accordance with the present invention (for example, as described in US Patent Application Publications 2008/0118550, 2007/0202149, 2007/0071798, 2006/0110457, 2006/0078586, 2006/0067983, 2006/0067976, 2006/0067975). Preferred methods for curing the starting material to produce a pre-cure, and then a fatty-acid-based, pre-cure-derived biomaterial include, but are not limited to, heating (e.g., employing an oven, a broadband infrared (IR) light source, a coherent IR light source (e.g., laser), and combinations thereof) and ultraviolet (UV) irradiation. The starting material may be cross-linked through auto-oxidation (i.e., oxidative cross-linking).

In accordance with various embodiments described herein, the drug release coatings of the present invention are formed of a pre-cure-derived biomaterial, which can be derived from saturated and unsaturated fatty acid compounds (e.g., free fatty acids, fatty acid ester, monoglycerides, diglycerides, triglycerides, metal salts, etc.). Preferably, the source of fatty acids described herein is saturated and unsaturated fatty acids such as those readily available in triglyceride form in various oils (e.g., fish oils). One method of the formation of a pre-cure-derived biomaterial is accomplished through autoxidation of the oil. As a liquid oil containing unsaturated fatty acid is heated, autoxidation occurs with the absorption of oxygen into the oil to create hydroperoxides in an amount dependent upon the amount of unsaturated (C=C) sites in the oil. However, the (C=C) bonds are not consumed in this initial reaction. Concurrent with the formation of hydroperoxides is the isomerization of (C=C) double bonds from cis to trans in addition to double bond conjugation. Continued heating of the oil results in the solidifying of the coating through the formation of cross-linking and by the further reaction of the hydroperoxides and the cleavage of C=C double bonds, which convert them into lower molecular weight secondary oxidation byproducts including aldehydes, ketones, alcohols, fatty acids, esters, lactones, ethers, and hydrocarbons which can either remain within the coating and/or are volatilized during the process.

Figure 2:
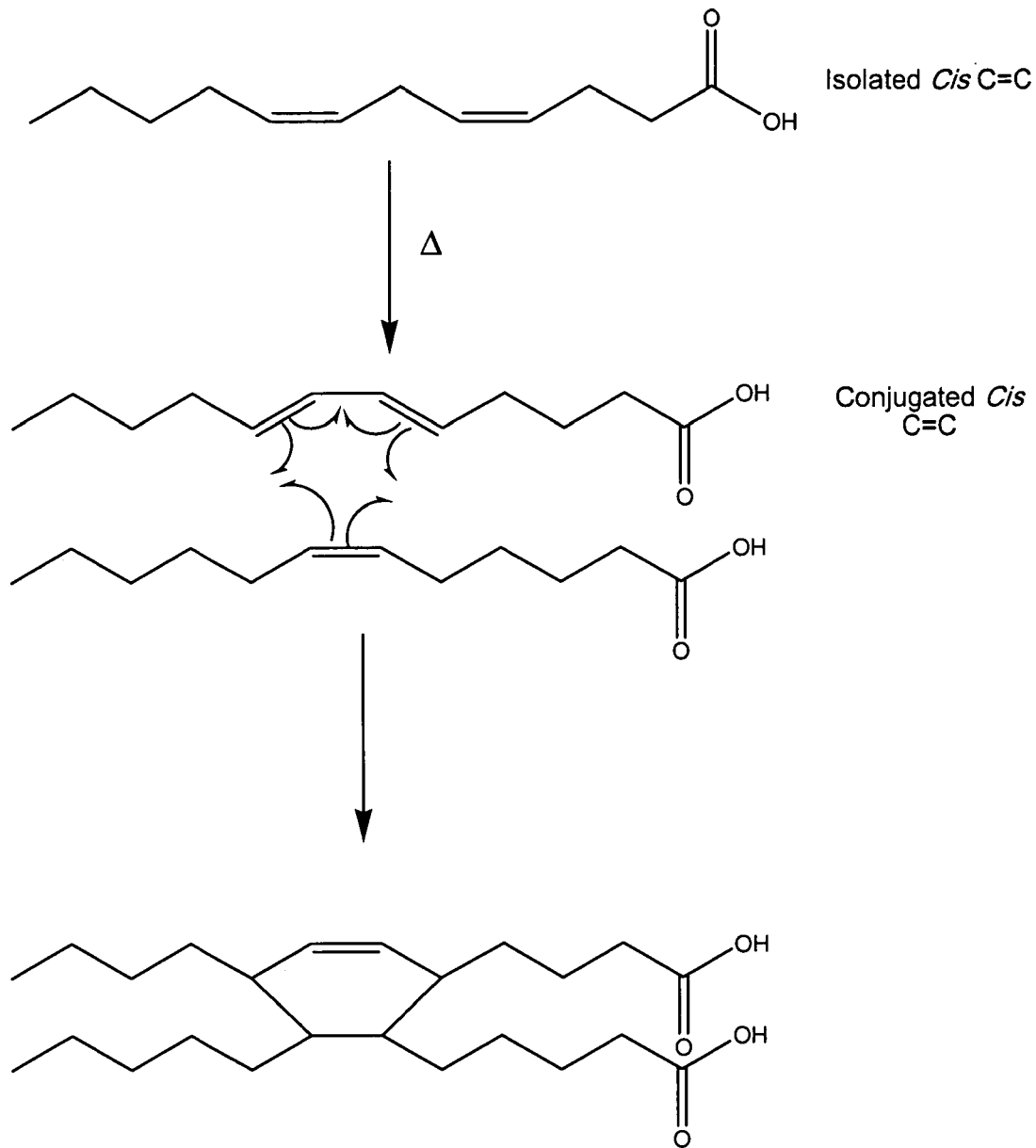
FIG. 2 is a schematic illustration of an example of the creation carbon-carbon cross-linking in a polyunsaturated oil (Diels-Alder type reaction)

The type and amount of cross-links formed during oil oxidation can be tailored depending on the conditions selected (e.g., coating thickness, temperature, metal composition, etc.). For instance, heating of the oil allows for cross-linking between the fish oil unsaturated chains using a combination of peroxide (C—O—O—C), ether (C—O—C), and hydrocarbon (C—C) bridges (see, e.g., F. D. Gunstone, "Fatty Acid and Lipid Chemistry." 1999.). However, heating at lower temperatures (i.e., below 150° C.) results in the formation of predominantly peroxide cross-links where heating at higher temperatures (i.e., above 150° C.) results in the thermal degradation of peroxides and C=C and ether cross-links dominate (F. D. Gunstone, 1999). Schematic illustrations of various cross-linking mechanisms and schemes are shown in FIGS. 1-2.

In addition to thermal curing processes, oxidation of oils can also be induced by light (e.g., photo-oxygenation).

Photo-oxygenation is limited to C═C carbon atoms and results in a conversion from cis to trans C═C isomers during curing (as occurs with heat initiated curing). However, photo-oxygenation using UV is a relatively quicker reaction than autoxidation from heat curing, in the realm of about 1000-1500 times faster. The quicker reaction especially holds true for methylene interrupted polyunsaturated fatty acids, such as EPA and DHA, which are found in the fish oil based embodiments of the present invention.

An important aspect of UV curing when compared to heat curing is that although the byproducts obtained by both curing methods are similar, they are not necessarily identical in amount or chemical structure. One reason for this is due to the ability of photo-oxygenation to create hydroperoxides at more possible C═C sites.

Photo-oxygenation, such as that which results from UV curing, due to its enhanced ability to create inner hydroperoxides, also results in the ability to form relatively greater amounts of cyclic byproducts, which also relates to peroxide cross-linking between fish oil hydrocarbon chains. For example, photo-oxygenation of linolenate results in 6 different types of hydroperoxides to be formed, whereas autoxidation results in only 4. The greater amount of hydroperoxides created using photo-oxygenation results in a similar, but slightly different, structure and amount of secondary byproducts to be formed relative to autoxidation from heat curing. Specifically, these byproducts are aldehydes, ketones, alcohols, fatty acids, esters, lactones, ethers, and hydrocarbons.

Figure 3:
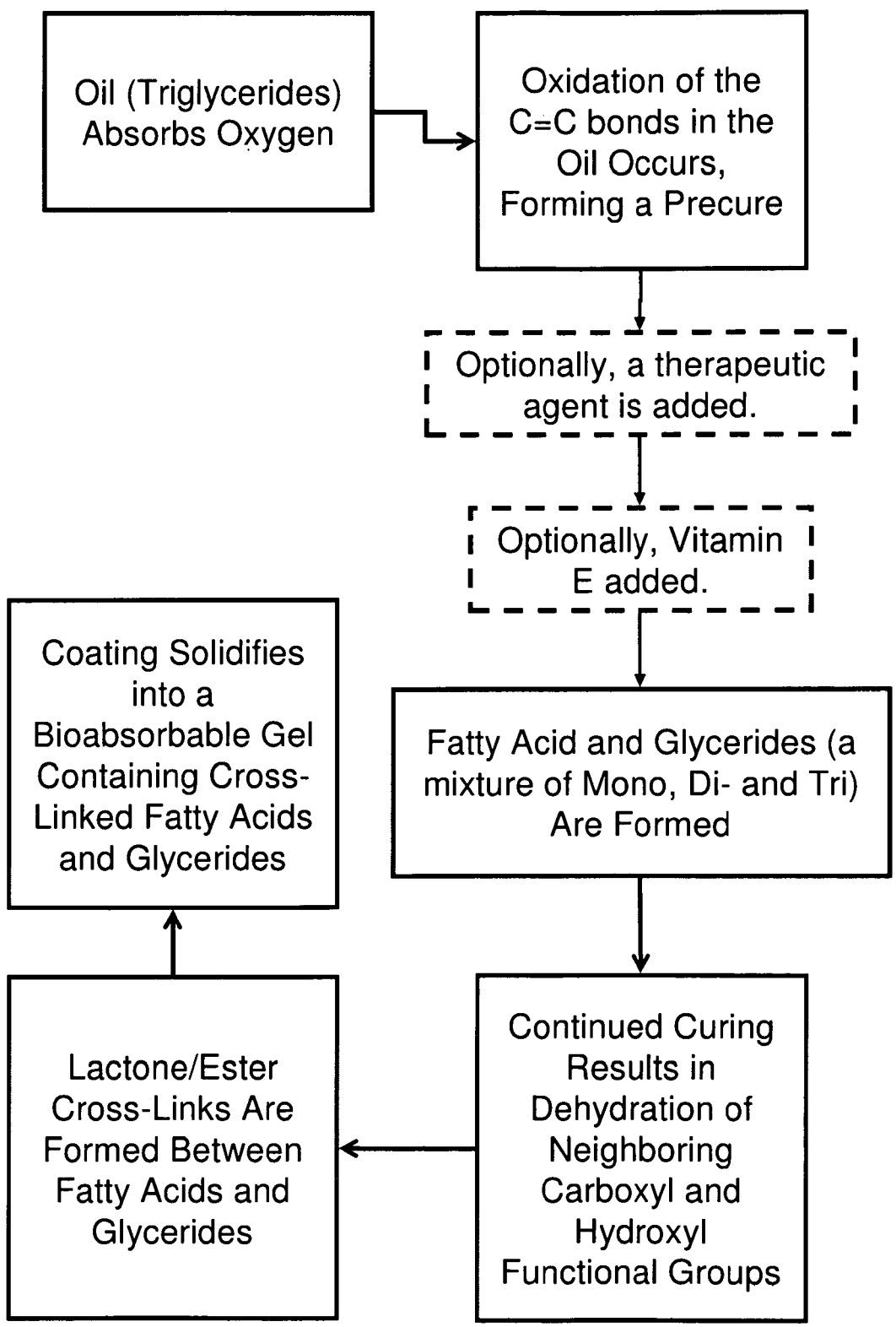
FIG. 3 shows the mechanism for the formation of the hydrophobic pre-cured-derived biomaterial coating.

Depending on the oil curing conditions and the fatty acid composition of the starting oil, a fatty acid-derived biomaterial (i.e., pre-cure and pre-cure derived) can be produced by curing the oil so as to oxidize the double bonds of the unsaturated fatty acid chains while predominantly preserving triglyceride ester functional groups. The oxidation of the unsaturated fatty acid chains results in the formation of hydroperoxides, which, with continued curing, are converted into aldehydes, ketones, alcohols, fatty acids, esters, lactones, ethers, and hydrocarbons. With continued heating of the oxidized oil, the byproducts are volatilized, resulting in an increase in the coating viscosity in addition to the formation of ester cross-links. The formation of ester and lactone cross-links can occur different types of mechanisms (i.e., esterification, alcoholysis, acidolysis, interesterification as described in F. D. Gunstone, 1999) between the hydroxyl and carboxyl functional components in the coating formed from the oxidation process (i.e., glyceride and fatty acid). The cross-linking reaction can form different types of ester linkages such as ester, anhydride, aliphatic peroxide, and lactones. FIGS. 3-4 summarize the mechanism for the formation of the oil derived biomaterial and reaction chemistry, respectively. As described in FIG. 3, after oxidation of the oil, i.e., after forming the precure, a therapeutic agent can optionally be added. Vitamin E can also be added in addition to the therapeutic agent, which will protect the agent and pre-cured oil from further oxidation, but does not inhibit further cross linking of the fatty acid and/or glyceride components of the oil. FIG. 5 provides a schematic of different methods to form esters from oils reaction schemes for illustrative purposes, but is not meant to be limiting in its scope to the invention.

Pre-cure-derived biomaterial coatings and stand-alone films of the present invention can be formed from an oil component. The term "oil component" is also referred to herein as the "oil-containing starting material." The "oil-containing starting material" may be natural or derived from synthetic sources. Preferably, the "oil containing starting material" comprises unsaturated fatty acids. The oil component can be either an oil, or an oil composition. The oil component can be a naturally occurring oil, such as fish oil, flax seed oil, grape seed oil, a synthetic oil, or other oils having desired characteristics. One example embodiment of the present invention makes use of a fish oil in part because of the high content of omega-3 fatty acids, which can provide healing support for damaged tissue, as discussed herein. The fish oil can also serve as an anti-adhesion agent. In addition, the fish oil maintains anti-inflammatory or non-inflammatory properties as well. The present invention is not limited to formation of the fatty acid-derived, pre-cured biomaterial with fish oil as the naturally occurring oil. However, the following description makes reference to the use of fish oil as one example embodiment. Other naturally occurring oils or synthetic oils can be utilized in accordance with the present invention as described herein.

Figure 6:
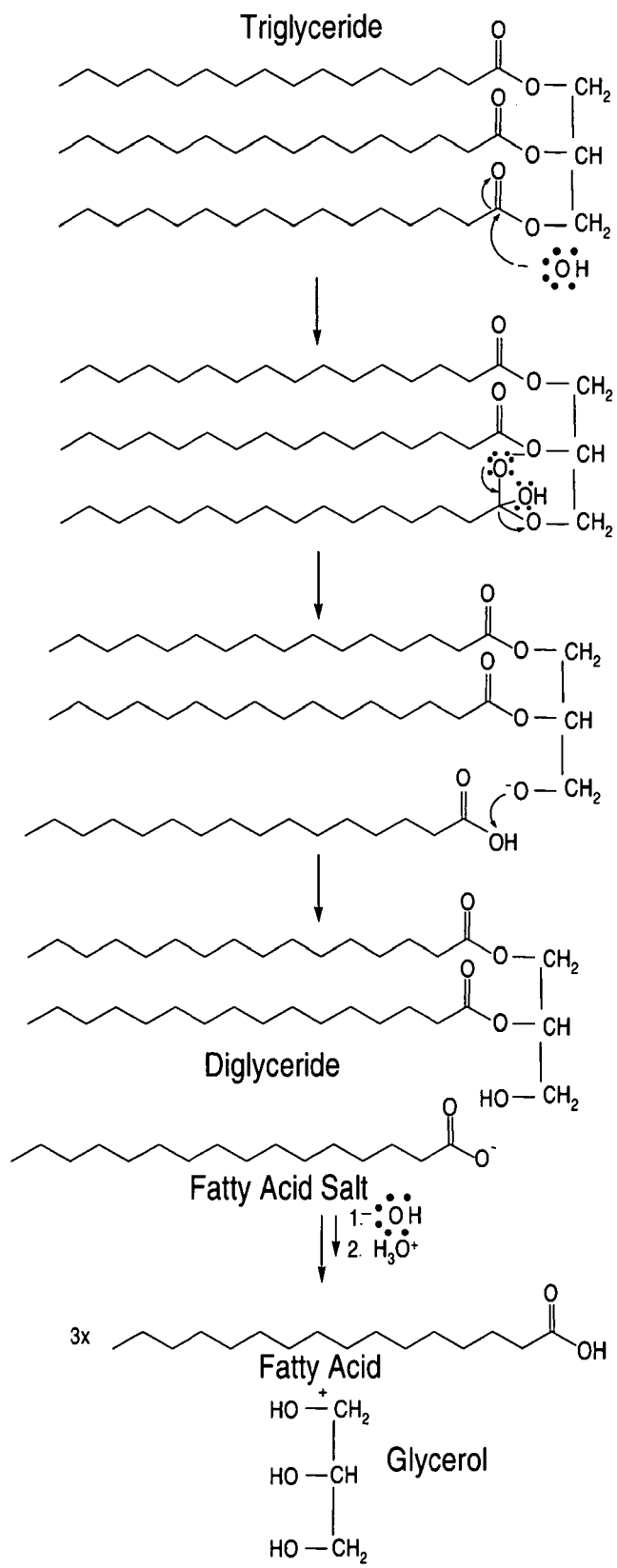
FIG. 6 schematically depicts the hydrolysis of the ester links in a triglyceride.

Coating Hydrolysis and Bioabsorption Chemistry of Fatty-Acid-Based, Pre-Cure Derived Biomaterials Biodegradable and bioabsorbable implantable materials with ester, lactone, and anhydride functional groups are typically broken down by either chemical and/or enzymatic hydrolysis mechanisms (K. Park et al., "Biodegradable Hydrogels for Drug Delivery." 1993; J. M. Andersen, "Perspectives on the In-Vivo Responses of Biodegradable Polymers." in *Biomedical Applications of Synthetic Biodegradable Polymers*, edited by Jeffrey O. Hollinger. 1995, pgs 223-233). Chemical hydrolysis of a pre-cure-derived biomaterial occurs when the functional group present in the material is cleaved by water. An example of chemical hydrolysis of a triglyceride under basic conditions is presented in FIG. 6. Enzymatic hydrolysis is the cleavage of functional groups in a pre-cure-derived biomaterial caused by the reaction with a specific enzyme (i.e., triglycerides are broken down by lipases (enzymes) that result in free fatty acids that can then be transported across cell membranes). The length of time a biodegradable and/or biodegradable pre-cure-derived biomaterial takes to be hydrolyzed is dependent on several factors such as the cross-linking density of the material, the thickness, the hydration ability of the coating, the crystallinity of the pre-cure-derived biomaterial, and the ability for the hydrolysis products to be metabolized by the body (K. Park et al., 1993 and J. M. Andersen, 1995).

A bio-absorbable substance is different from a biodegradable substance. Biodegradable is generally defined as capable of being decomposed by biological agents, or capable of being broken down by microorganisms or biological processes. Biodegradable substances can cause an inflammatory response due to either the parent substance or those formed during breakdown, and they may or may not be absorbed by tissues. Some biodegradable substances are limited to bulk erosion mechanism for breakdown. For example, a commonly used biodegradable polymer, PLGA (poly(lactic-co-glycolic acid)) undergoes chemical hydrolysis in-vivo to form two alpha-hydroxy acids, specifically glycolic and lactic acids. Although glycolic and lactic acids are byproducts of various metabolic pathways in the body, it has been previously demonstrated in previous medical implant and local drug delivery applications that a local concentration of these products results in an acidic environment to be produced, which can lead to inflammation and damage to local tissue (S. Dumitriu, "Polymeric Biomaterials." 2002). Clinically, this can lead to impaired clinical outcomes such as restenosis (D. E. Drachman and D. I. Simon. Current Atherosclerosis Reports. 2005, Vol 7, pgs 44-49; S. E. Goldblum et al. Infection and Immunity. 1989, Vol. 57, No. 4, pgs 1218-1226) and impaired healing in a coronary stent application which can lead to late-stent thrombosis or adhesion formation in an abdominal hernia repair (Y. C. Cheong et al. *Human Reproduction Update.* 2001; Vol. 7, No. 6: pgs 556-566). Thus, an ideal pre-cure-derived biomaterial should not only demonstrate excellent biocompatibility upon implantation, but should also maintain that biocompatibility during the life of its implantation with its hydrolysis byproducts being absorbable by local tissue.

The bio-absorbable nature of the pre-cure-derived biomaterials used as a stand-alone film, a coating for a medical device, or in drug delivery applications results in the bio-material being absorbed over time by the cells of the body tissue. In various embodiments, there are substantially no substances in the coating, or in vivo conversion by-products of the coating, that induce an inflammatory response, e.g., the coating converts in vivo into non-inflammatory components. For example, in various embodiments, the coatings of the present invention upon absorption and hydrolysis do not produce lactic acid and glycolic acid break-down products in measurable amounts. The chemistry of the pre-cure-derived biomaterial described herein consists of predominantly fatty acid and glyceride components that can either be hydrolyzed in-vivo by chemical and/or enzymatic means which results in the release of fatty acid and glyceride components that can be transported across cell membranes. Subsequently, the fatty acid and glyceride components eluted from the pre-cure-derived biomaterial are directly metabolized by cells (i.e., they are bio-absorbable). The bio-absorbable nature of the coating and stand-alone film of the present invention results in the coating being absorbed over time, leaving only an underlying delivery or other medical device structure that is biocompatible. There is substantially no foreign body inflammatory response to the bio-absorbable coating or its hydrolysis breakdown products in the preferred embodiments of the present invention.

Fatty-Acid-Based, Pre-Cure Derived Biomaterial Biocompatibility and In-Vivo Performance The process of making the pre-cure-derived biomaterials (e.g., coating or stand-alone film) as described herein led to some unexpected chemical processes and characteristics in view of traditional scientific reports in the literature about the oxidation of oils (J. Dubois et al. *JAOCS.* 1996, Vol. 73, No. 6., pgs 787-794.H. Ohkawa et al., *Analytical Biochemistry,* 1979, Vol. 95, pgs 351-358.; H. H. Draper, 2000, Vol. 29, No. 11, pgs 1071-1077). Oil oxidation has traditionally been of concern for oil curing procedures due to the formation of reactive byproducts such as hydroperoxides and alpha-beta unsaturated aldehydes that are not considered to be biocompatible (H. C. Yeo et al. *Methods in Enzymology.* 1999, Vol. 300, pgs 70-78.; S-S. Kim et al. *Lipids.* 1999, Vol. 34, No. 5, pgs 489-496.). However, the oxidation of fatty acids from oils and fats are normal and important in the control of biochemical processes in-vivo. For example, the regulation of certain biochemical pathways, such as to promote or reduce inflammation, is controlled by different lipid oxidation products (V. N. Bochkov and N. Leitinger. *J. Mol. Med.* 2003; Vol. 81, pgs 613-626). Additionally, omega-3 fatty acids are known to be important for human health and specifically EPA and DHA are known to have anti-inflammatory properties in-vivo. However, EPA and DHA are not anti-inflammatory themselves, but it is the oxidative byproducts they are biochemically converted into that produce anti-inflammatory effects in-vivo (V. N. Bochkov and N. Leitinger, 2003; L. J. Roberts II et al. *The Journal of Biological Chemistry.* 1998; Vol. 273, No. 22, pgs 13605-13612.). Thus, although there are certain oil oxidation products that are not biocompatible, there are also several others that have positive biochemical properties in-vivo (V. N. Bochkov and N. Leitinger, 2003; F. M. Sacks and H. Campos. *J Clin Endocrinol Metab.* 2006; Vol. 91, No. 2, pgs 398-400; A. Mishra et al. *Arterioscler Thromb Vasc Biol.* 2004; pgs 1621-1627). Thus, by selecting the appropriate process conditions, a fatty acid-derived cross-linked hydrophobic fatty acid-derived, pre-cured biomaterial (from, e.g., fish oil) can be created and controlled using oil oxidation chemistry with a final chemical profile that will have a favorable biological performance in-vivo.

The process of making a pre-cure-derived biomaterial as described herein leads to a final chemical profile that is biocompatible, minimizes adhesion formation, acts as a tissue separating barrier, and is non-inflammatory with respect to the material chemistry and the products produced upon hydrolysis and absorption by the body in-vivo. The reason for these properties is due to several unique characteristics of the fatty acid-derived, pre-cured biomaterials (e.g., coatings or stand-alone films) of the invention.

One important aspect of the invention is that no toxic, short-chained cross-linking agents (such as glutaraldehyde) are used to form the fatty acid-derived, pre-cured biomaterials (e.g., coatings or stand-alone films) of the invention. It has been previously demonstrated in the literature that short chain cross-linking agents can elute during hydrolysis of biodegradable polymers and cause local tissue inflammation. The process of creating pre-cure-derived biomaterials does not involve cross-linking agents because the oil is solely cured into a coating using oil autoxidation or photo-oxidation chemistry. The oxidation process results in the formation of carboxyl and hydroxyl functional groups that allow for the pre-cure-derived biomaterial to become hydrated very rapidly and become slippery, which allows for frictional injury during and after implantation to be significantly reduced and/or eliminated. The methods of making the pre-cure-derived biomaterials described herein allow the alkyl chains of the fatty acid, glyceride and other lipid byproducts present in the coating to be disordered, which creates a coating that is flexible and aids in handling of the material while being implanted.

There are several individual chemical components of the coating that aid in its biocompatibility and its low to non-inflammatory response observed in-vivo. One critical aspect is that the process of creating a pre-cure-derived biomaterial as described herein results in low to non-detectable amounts of oxidized lipid byproducts of biocompatibility concern, such as aldehydes. These products are either almost completely reacted or volatilized during the curing process as described herein. The process of creating a pre-cure-derived biomaterial largely preserves the esters of the native oil triglycerides and forms ester and/or lactone cross-links, which are biocompatible (K. Park et al., 1993; J. M. Andersen, 1995).

In addition to general chemical properties of a pre-cure-derived biomaterial that assists in its biocompatibility, there are also specific chemical components that have positive biological properties. Another aspect is that the fatty acid chemistry produced upon creation of a pre-cure-derived biomaterial is similar to the fatty acid chemistry of tissue, as presented in FIG. 7. Thus, as fatty acids are eluting from the coating they are not viewed as being "foreign" by the body and cause an inflammatory response. In fact, C14 (myristic) and C16 (palmitic) fatty acids present in the coating have been shown in the literature to reduce production of α-TNF, an inflammatory cytokine. The expression of α-TNF has been identified as one of the key cytokines responsible for "turning on" inflammation in the peoritoneal after hernia repair, which can then lead to abnormal healing and adhesion formation (Y. C. Cheong et al., 2001). α-TNF is also an important cytokine in vascular injury and inflammation (D. E. Drachman and D. I. Simon, 2005; S. E. Goldblum, 1989), such as vascular injury caused during a stent deployment. In addition to the fatty acids just specified, there have also been additional oxidized fatty acids identified that have anti-inflammatory properties. A final component identified from the fatty acid-derived coatings as described herein are delta-lactones (i.e., 6-membered ring cyclic esters). Delta-lactones have been identified as having anti-tumor properties (H. Tanaka et al. *Life Sciences* 2007; Vol. 80, pgs 1851-1855).

These components identified are not meant to be limiting in scope to the present invention as changes in starting oil composition and/or process conditions can invariably alter the fatty acid and/or oxidative byproduct profiles and can be tailored as needed depending on the intended purpose and site of application of the fatty acid-derived, pre-cured biomaterial.

In summary, the biocompatibility and observed in in-vivo performance of pre-cure-derived biomaterials described herein is due to the elution of fatty acids during hydrolysis of the material during implantation and healing and is not only beneficial as to prevent a foreign body response in-vivo due to the similarity of the fatty acid composition of the material to native tissue (i.e., a biological "stealth" coating), but the specific fatty acids and/or other lipid oxidation components eluting from the coating aid in preventing foreign body reactions and reducing or eliminating inflammation, which leads to improved patient outcomes. Additionally, the fatty acid and glyceride components eluted from the pre-cure-derived biomaterial are able to be absorbed by local tissue and metabolized by cells, in, for example, the Citric Acid Cycle (M. J. Campell, "Biochemistry: Second Edition." 1995, pgs 366-389). Hence, the pre-cure-derived biomaterial (e.g., coating or stand-alone film) described herein is also bioabsorbable.

Accordingly, in one aspect, the invention provides a bio-absorbable, oil-based coating for a medical device, comprising a cross-linked fatty acid oil-derived biomaterial with a pre-cured component and a therapeutic agent. The invention also provides a bio-absorbable, oil-based stand-alone film, comprising a cross-linked fatty acid oil-derived biomaterial with a pre-cured component and a therapeutic agent. The coating and stand-alone film can be prepared according to the methods discussed herein.

Methods of Treatment Using Fatty Acid-Derived Materials

Also provided herein is a fatty acid-based, pre-cure-derived biomaterial suitable for treating or preventing disorders related to vascular injury and/or vascular inflammation. The fatty acid-based, pre-cure-derived biomaterial can also be used to treat or prevent injury to tissue, e.g., soft tissue. The fatty acid-based, pre-cure-derived biomaterial can be a coating for a medical device or a stand-alone film. In another embodiment, the source of the fatty acid for the biomaterial is an oil, such as fish oil.

In general, four types of soft tissue are present in humans: epithelial tissue, e.g., the skin and the lining of the vessels and many organs; connective tissue, e.g., tendons, ligaments, cartilage, fat, blood vessels, and bone; muscle, e.g., skeletal (striated), cardiac, or smooth; and nervous tissue, e.g., brain, spinal cord and nerves. The fatty acid-based, pre-cure-derived biomateri al of the invention (e.g., pre-cure-derived stand-alone film) can be used to treat injury to these soft tissue areas. Thus, in one embodiment, the fatty acid-based, pre-cure-derived biomaterial of the invention (e.g., pre-cured stand-alone film) can be used for promotion of proliferation of soft tissue for wound healing. Furthermore, following acute trauma, soft tissue can undergo changes and adaptations as a result of healing and the rehabilitative process. Such changes include, but are not limited to, metaplasia, which is conversion of one kind of tissue into a form that is not normal for that tissue; dysplasia, with is the abnormal development of tissue; hyperplasia, which is excessive proliferation of normal cells in the normal tissue arrangement; and atrophy, which is a decrease in the size of tissue due to cell death and resorption or decreased cell proliferation. Accordingly, the fatty acid-based, pre-cure-derived biomaterial of the invention (e.g., pre-cured stand-alone film) can be used for the diminishment or alleviation of at least one symptom associated with or caused by acute trauma in soft tissue.

In one embodiment of the present invention, as described below, the fatty acid-based, pre-cure-derived biomaterial can be used, for example, to prevent tissue adhesion. The tissue adhesion can be, for example, a result of blunt dissection. Blunt dissection can be generally described as dissection accomplished by separating tissues along natural cleavage lines without cutting. Blunt dissection is executed using a number of different blunt surgical tools, as is understood by those of ordinary skill in the art. Blunt dissection is often performed in cardiovascular, colo-rectal, urology, gynecology, upper GI, and plastic surgery applications, among others.

After the blunt dissection separates the desired tissues into separate areas, there is often a need to maintain the separation of those tissues. In fact, post surgical adhesions can occur following almost any type of surgery, resulting in serious postoperative complications. The formation of surgical adhesions is a complex inflammatory process in which tissues that normally remain separated in the body come into physical contact with one another and attach to each other as a result of surgical trauma.

It is believed that adhesions are formed when bleeding and leakage of plasma proteins from damaged tissue deposit in the abdominal cavity and form what is called a fibrinous exudate. Fibrin, which restores injured tissues, is sticky, so the fibrinous exudate may attach to adjacent anatomical structures in the abdomen. Post-traumatic or continuous inflammation exaggerates this process, as fibrin deposition is a uniform host response to local inflammation. This attachment seems to be reversible during the first few days after injury because the fibrinous exudates go through enzymatic degradation caused by the release of fibrinolytic factors, most notably tissue-type plasminogen activator (t-PA). There is constant play between t-PA and plasminogen-activator inhibitors. Surgical trauma usually decreases t-PA activity and increases plasminogen-activator inhibitors. When this happens, the fibrin in the fibrinous exudate is replaced by collagen. Blood vessels begin to form, which leads to the development of an adhesion. Once this has occurred, the adhesion is believed to be irreversible. Therefore, the balance between fibrin deposition and degradation during the first few days post-trauma is critical to the development of adhesions (Holmdahl L. *Lancet* 1999; 353: 1456-57). If normal fibrinolytic activity can be maintained or quickly restored, fibrous deposits are lysed and permanent adhesions can be avoided. Adhesions can appear as thin sheets of tissue or as thick fibrous bands.

Often, the inflammatory response is also triggered by a foreign substance in vivo, such as an implanted medical device. The body sees this implant as a foreign substance, and the inflammatory response is a cellular reaction to wall off the foreign material. This inflammation can lead to adhesion formation to the implanted device; therefore a material that causes little to no inflammatory response is desired.

Thus, the fatty acid-based, pre-cure-derived biomaterial (e.g., stand-alone film) of the present invention may be used as a barrier to keep tissues separated to avoid the formation of adhesions, e.g., surgical adhesions. Application examples for adhesion prevention include abdominal surgeries, spinal repair, orthopedic surgeries, tendon and ligament repairs, gynecological and pelvic surgeries, and nerve repair applications. The fatty acid-based, pre-cure-derived biomaterial (e.g., stand-alone film) may be applied over the trauma site or wrapped around the tissue or organ to limit adhesion formation. The addition of therapeutic agents to the fatty acid-based, pre-cure-derived biomaterial used in these adhesion prevention applications can be utilized for additional beneficial effects, such as pain relief or infection minimization. Other surgical applications of the fatty acid-based, pre-cure-derived biomaterial may include using a stand-alone film as a dura patch, buttressing material, internal wound care (such as a graft anastomotic site), and internal drug delivery system. The fatty acid-based, pre-cure-derived biomaterial may also be used in applications in transdermal, wound healing, and non-surgical fields. The fatty acid-based, pre-cure-derived biomaterial may be used in external wound care, such as a treatment for burns or skin ulcers. The fatty acid-based, pre-cure-derived biomaterial may be used without any therapeutic agent as a clean, non-permeable, non-adhesive, non-inflammatory, anti-inflammatory dressing, or the fatty acid-based, pre-cure-derived biomaterial may be used with one or more therapeutic agents for additional beneficial effects. The fatty acid-based, pre-cure-derived biomaterial may also be used as a transdermal drug delivery patch when the fatty acid-based, pre-cure-derived biomaterial is loaded or coated with one or more therapeutic agents.

The process of wound healing involves tissue repair in response to injury and it encompasses many different biologic processes, including epithelial growth and differentiation, fibrous tissue production and function, angiogenesis, and inflammation. Accordingly, the fatty acid-based, pre-cure-derived biomaterial (e.g., stand-alone film) provides an excellent material suitable for wound healing applications.

Modulated Healing

Also provided herein is a fatty acid-based, pre-cure-derived biomaterial suitable for achieving modulated healing in a tissue region in need thereof, wherein the composition is administered in an amount sufficient to achieve said modulated healing. In one embodiment, the fatty acid-based, pre-cure-derived biomaterial is a medical coating for a medical device or a stand-alone film. In another embodiment, the source of the fatty acid for the biomaterial is an oil, such as fish oil.

Modulated healing can be described as the in-vivo effect observed post-implant in which the biological response is altered resulting in a significant reduction in foreign body response. As utilized herein, the phrase "modulated healing" and variants of this language generally refers to the modulation (e.g., alteration, delay, retardation, reduction, detaining) of a process involving different cascades or sequences of naturally occurring tissue repair in response to localized tissue injury, substantially reducing their inflammatory effect. Modulated healing encompasses many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other. For example, the fatty acids described herein can alter, delay, retard, reduce, and/or detain one or more of the phases associated with healing of vascular injury caused by medical procedures, including, but not limited to, the inflammatory phase (e.g., platelet or fibrin deposition), and the proliferative phase. In one embodiment, "modulated healing" refers to the ability of a fatty acid derived biomaterial to alter a substantial inflammatory phase (e.g., platelet or fibrin deposition) at the beginning of the tissue healing process. As used herein, the phrase "alter a substantial inflammatory phase" refers to the ability of the fatty acid derived biomaterial to substantially reduce the inflammatory response at an injury site. In such an instance, a minor amount of inflammation may ensue in response to tissue injury, but this level of inflammation response, e.g., platelet and/or fibrin deposition, is substantially reduced when compared to inflammation that takes place in the absence of the fatty acid derived biomaterial.

For example, the fatty acid-based, pre-cure-derived biomaterial (e.g., fatty acid-based, pre-cure-derived coating or fatty acid-based, pre-cure-derived stand-alone film) of the present invention has been shown experimentally in animal models to delay or alter the inflammatory response associated with vascular injury, as well as excessive formation of connective fibrous tissue following tissue injury. The fatty acid-based, pre-cure-derived biomaterial (e.g., coating or stand-alone film) of the present invention can delay or reduce fibrin deposition and platelet attachment to a blood contact surface following vascular injury.

Accordingly, the fatty acid-based, pre-cure-derived biomaterial (e.g., coating or stand-alone film) of the present invention provides an excellent absorbable cellular interface suitable for use with a surgical instrument or medical device that results in a modulated healing effect, avoiding the generation of scar tissue and promoting the formation of healthy tissue at a modulated or delayed period in time following the injury. Without being bound by theory, this modulated healing effect can be attributed to the modulation (e.g., alteration, delay, retardation, reduction, detaining) of any of the molecular processes associated with the healing processes of vascular injury. For example, the fatty acid-based, pre-cure-derived biomaterial (e.g., fatty acid-based, pre-cure-derived coating or fatty acid-based, pre-cure-derived film) of the present invention can act as a barrier or blocking layer between a medical device implant (e.g., a surgical mesh, graft, or stent), or surgical instrument, and the cells and proteins that compose the vessel wall, such as the endothelial cells and smooth muscle cells that line the vessel's interior surface. The barrier layer prevents the interaction between the surgical implant and the vessel surface, thereby preventing the initiation of the healing process by the cells and proteins of the vessel wall. In this respect, the barrier layer acts as a patch that binds to the vessel wall and blocks cells and proteins of the vessel wall from recognizing the surgical implant (i.e., the barrier layer blocks cell-device and/or protein-device interactions), thereby blocking the initiation of the vascular healing process, and avoiding the fibrin activation and deposition and platelet activation and deposition.

In another non-binding example, the modulated healing effect can be attributed to the modulation (e.g., alteration, delay, retardation, reduction, detaining) of signaling between the cells and proteins that compose the vessel wall and various components of the bloodstream that would otherwise initiate the vascular healing process. Stated differently, at the site of vascular injury, the fatty acid derived biomaterial (e.g., coating or stand-alone film) of the present invention can modulate the interaction of cells of the vessel wall, such as endothelial cells and/or smooth muscle cells, with other cells and/or proteins of the blood that would otherwise interact with the damaged cells to initiate the healing process. Additionally, at the site of vascular injury, the fatty acid-based, pre-cure-derived biomaterial (e.g., coating or stand-alone film) of the present invention can modulate the interaction of proteins of the vessel wall with other cells and/or proteins of the blood, thereby modulating the healing process.

The fatty acid-based, pre-cure-derived biomaterial (e.g., coating or stand-alone film) of the present invention can be designed to maintain its integrity for a desired period of time, and then begin to hydrolyze and be absorbed into the tissue that it is surrounded by. Alternatively, the fatty acid-based, pre-cure-derived biomaterial can be designed such that, to some degree, it is absorbed into surrounding tissue immediately after the fatty acid derived biomaterial is inserted in the subject. Depending on the formulation of the fatty acid-based, pre-cure-derived biomaterial, it can be completely absorbed into surrounding tissue within a time period of 1 day to 24 months, e.g., 1 week to 12 months, e.g., 1 month to 10 months, e.g., 3 months to 6 months. Animal studies have shown resorption of the fatty acid derived biomaterial occurring upon implantation and continuing over a 3 to 6 month period, and beyond.

Tailoring of Drug Release Profiles

In various aspects, the present invention provides methods of curing a of a fatty acid-derived coating, preferably fish oil, to provide a fatty acid-derived, pre-cured biomaterial coating or stand-alone film containing one or more therapeutic agents that can tailor the release profile of a therapeutic agent from the coating or film. The release profile can be tailored, e.g., through changes in oil (e.g., fish oil) chemistry by varying coating composition, temperature, and cure times. The position of the drug-containing layer on the coated device provides an additional mechanism to alter the release profile of the non-polymeric cross-linked fatty acid-derived, pre-cured biomaterial coating. This can be achieved, e.g., by loading a drug into a cured base coating layer and coating a topcoat overlayer cured coating onto the previously cured encapsulating base layer.

An advantage of the cured fish oil coating and stand-alone film in various embodiments of the present invention is that the curing conditions utilized (i.e., cure time and temperature) can directly influence the amount of coating cross-linking density and byproduct formation, which in turn effects the coating degradation. Thus, by altering the curing conditions employed, the dissolution rate of a therapeutic compound of interest contained in the coating can also be altered.

In various embodiments of the present invention, an agent, such as, e.g., a free radical scavenger, can be added to the starting material to tailor the drug release profile of the fatty acid-derived, pre-cured biomaterial that is formed. In various embodiments, vitamin E is added to the starting material to, for example, to slow down autoxidation in fish oil by reducing hydroperoxide formation, which can result in a decrease in the amount of cross-linking observed in a cured fish oil coating. In addition, other agents can be used to increase the solubility of a therapeutic agent in the oil component of the starting material, protect the drug from degradation during the curing process, or both. For example, vitamin E can also be used to increase the solubility of certain drugs in a fish oil starting material, and thereby facilitate tailoring the drug load of the eventual cured coating. Thus, varying the amount of vitamin E present in the coating provides an additional mechanism to alter the cross-linking and chemical composition of the fatty acid-derived, pre-cured biomaterials (e.g., coatings and stand-alone films) of the present invention.

In various embodiments, the present invention provides coatings and stand-alone films where the drug release profile of the fatty acid-derived, pre-cured biomaterial is tailored through the provision of two or more coatings and selection of the location of the therapeutic agent. The drug location can be altered, e.g., by coating a bare portion of a medical device with a first starting material and creating a first cured coating, then coating at least a portion of the first cured-coating with the drug-oil formulation to create a second overlayer coating. The first starting material can contain one or more therapeutic agents. In various embodiments, the second overlayer coating is also cured. The drug load, drug release profiles, or both, of the first coating, the overlay coating, or both, can be tailored through the use of different curing conditions and/or addition of free radical scavengers (e.g., vitamin E), as described herein. The process of providing two layers can be extended to provide three or more layers, wherein at least one of the layers comprises a hydrophobic, cross-linked fatty acid-derived, pre-cured biomaterial prepared from a fatty-acid containing oil, such as fish oil. In addition, one or more of the layers can be drug eluting, and the drug release profile of such layers can be tailored using the methods described herein.

In various embodiments, the present invention provides coatings where the drug release profile of the overall coating is tailored through the provision of two or more coating regions with different drug release profiles and selection of the location of the therapeutic agent. In various embodiments, the formation of different coating regions with different drug release properties is obtained by location specific curing conditions, e.g., location specific UV irradiation, and/or location specific deposition of a starting material on the coated device, e.g., by ink jet printing methods.

Coating Approaches

FIG. 8 illustrates one method of making a medical device of the present invention, such as, e.g., a drug eluting coated stent, in accordance with one embodiment of the present invention. The process involves providing a medical device, such as the stent (step 100). A coating of a starting material, which is a non-polymeric cross-linked fatty acid-derived, pre-cured biomaterial coating, is then applied to the medical device (step 102). One of ordinary skill in the art will appreciate that this basic method of application of a coating to a medical device, such as a stent, can have a number of different variations falling within the process described. The step of applying a coating substance to form a coating on the medical device can include a number of different application methods. For example, the medical device can be dipped into a liquid solution of the coating substance. The coating substance can be sprayed onto the device. Another application method is painting the coating substance on to the medical device. One of ordinary skill in the art will appreciate that other methods, such as electrostatic adhesion, can be utilized to apply the coating substance to the medical device. Some application methods may be particular to the coating substance and/or to the structure of the medical device receiving the coating. Accordingly, the present invention is not limited to the specific embodiments of starting material application described herein, but is intended to apply generally to the application of the starting material which is to become a fatty acid-derived, pre-cured biomaterial coating of a medical device, taking whatever precautions are necessary to make the resulting coating maintain desired characteristics.

FIG. 9 is a flowchart illustrating one example implementation of the method of FIG. 8. In accordance with the steps illustrated in FIG. 9, a bio-absorbable carrier component (e.g., a fatty acid source, such as a naturally occurring oil) is provided (step 110). The carrier is then pre-cured ("partially cured") to induce an initial amount of cross linking (step 112). The resulting material can then be combined with a therapeutic agent, to form a pre-cured material that is to become a fatty acid-based, pre-cure-derived biomaterial coating (step 114). The pre-cured material is applied to the medical device, such as the stent 10, to form the coating (step 116). The coating is then cured (step 118) by any of the curing methods described herein to form a fatty acid-derived, pre-cured biomaterial coating.

In certain instances, a therapeutic agent that is desired for incorporation into a fatty acid-derived biomaterial coating is not stable to the thermal/UV curing process utilized to create the device coating (e.g., there is a significant amount of drug degradation observed). In order to maintain therapeutic agent composition and minimize degradation of the therapeutic agent, the fatty acid starting material (e.g., fish oil) can be first partially cured ("pre-cured"), in the absence of the therapeutic agent, to oxidize the unsaturated components in the oil. Such a process increases the viscosity of the oil and reduces its reactivity by partially cross-linking the fatty acids of the oil, for, e.g., medical device coating applications. The therapeutic agent can then be combined with the pre-cure in an organic solvent and sprayed and/or cast onto a medical device and/or as a stand-alone film material, and subsequently heated to form a final cross-linked material (i.e., a fatty acid-based, pre-cure-derived coating) for use in its intended application. This process results in incorporating the therapeutic agent into the fatty acid-derived, pre-cured biomaterial for extended drug release from the coating. Alternatively, after the creation of the pre-cure, an anti-oxidant such as Vitamin E can be combined with the therapeutic agent and an organic solvent for application onto a medical device or to create a stand-alone film. This coating is then also final cured into a fatty acid-derived, pre-cured biomaterial. While the antioxidant (e.g., Vitamin E) is oxidized during the final cure step, it prevents the therapeutic and oil components from being further oxidized and preserves the drug composition and activity. Although the antioxidant prevents further oxidation of the therapeutic and pre-cured oil components, it does not inhibit the formation of ester cross-links between the fatty acids upon cure, because the reactive carboxyl and hydroxyl functional groups needed to create the fatty acid-derived, pre-cured biomaterial were created during the initial thermal/UV curing treatment of the oil starting material, i.e., during the creation of the pre-cure.

The coated medical device is then sterilized using any number of different sterilization processes (step 118). For example, sterilization can be implemented utilizing ethylene oxide, gamma radiation, E beam, steam, gas plasma, or vaporized hydrogen peroxide. One of ordinary skill in the art will appreciate that other sterilization processes can also be applied, and that those listed herein are merely examples of sterilization processes that result in a sterilization of the coated stent, preferably without having a detrimental effect on the coating 20.

It should be noted that the fatty acid component (e.g., a fish oil) can be added multiple times to create multiple tiers in forming the coating. For example, if a thicker coating is desired, additional tiers of the fatty acid component can be added after steps 100, 102, 110, 112, 114, 116, 118 and/or 120. Different variations relating to when the fatty acid is cured and when other substances are added are possible in a number of different process configurations. Accordingly, the present invention is not limited to the specific sequence illustrated. Rather, different combinations of the basic steps illustrated are anticipated by the present invention.

Figure 10A:
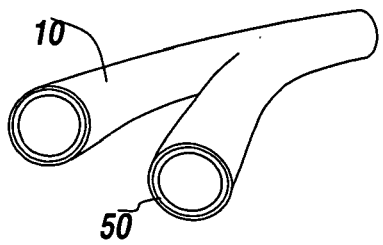
FIGS. 10A-10E are various images of coated medical devices.
Figure 10B:
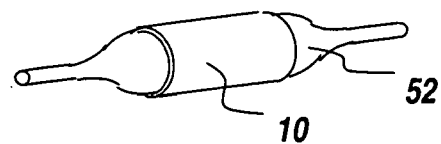
Figure 10C:
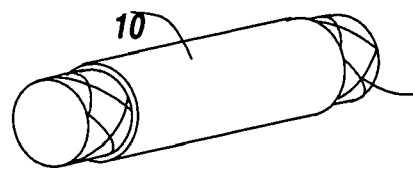
Figure 10D:
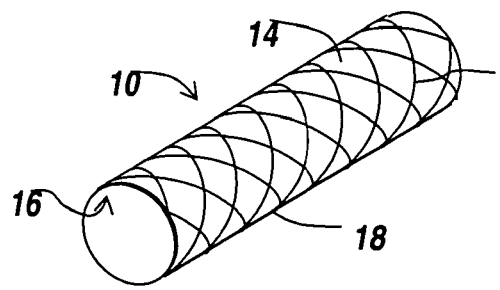
Figure 10E:
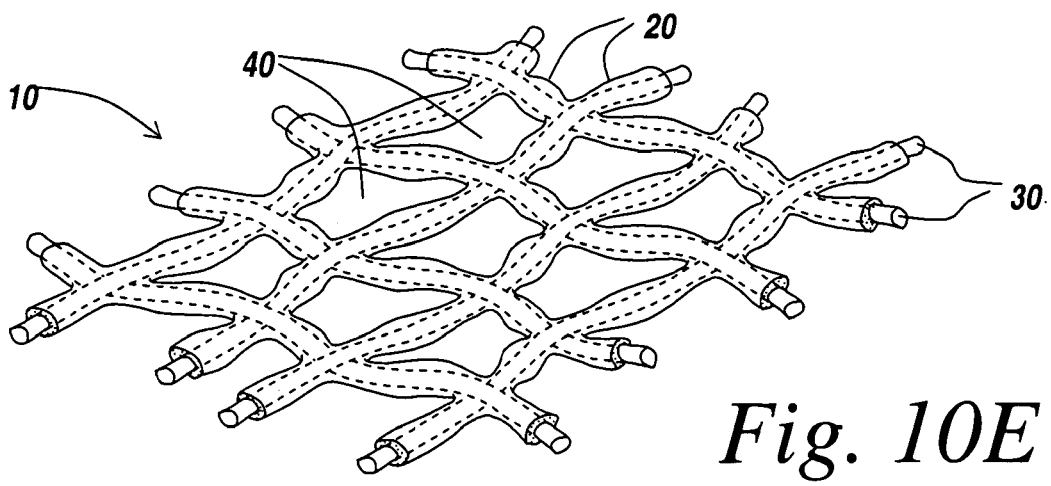

FIGS. 10A-10E illustrate some of the other forms of medical devices mentioned above in combination with the coating 10 of the present invention. FIG. 10A shows a graft 50 with the coating 10 coupled or adhered thereto. FIG. 10B shows a catheter balloon 52 with the coating 10 coupled or adhered thereto. FIG. 10C shows a stent 54 with the coating 10 coupled or adhered thereto. FIG. 10D illustrates a stent 10 in accordance with one embodiment of the present invention. The stent 10 is representative of a medical device that is suitable for having a coating applied thereon to effect a therapeutic result. The stent 10 is formed of a series of interconnected struts 12 having gaps 14 formed therebetween. The stent 10 is generally cylindrically shaped. Accordingly, the stent 10 maintains an interior surface 16 and an exterior surface 18. FIG. 10E illustrates a coated surgical mesh, represented as a biocompatible mesh structure 10, in accordance with one embodiment of the present invention. The biocompatible mesh structure 10 is flexible, to the extent that it can be placed in a flat, curved, or rolled configuration within a patient. The biocompatible mesh structure 10 is implantable, for both short term and long term applications. Depending on the particular formulation of the biocompatible mesh structure 10, the biocompatible mesh structure 10 will be present after implantation for a period of hours to days, or possibly months, or permanently.

Each of the medical devices illustrated, in addition to others not specifically illustrated or discussed, can be combined with the coating 10 using the methods described herein, or variations thereof. Accordingly, the present invention is not limited to the example embodiments illustrated. Rather the embodiments illustrated are merely example implementations of the present invention.

In another embodiment, the biomaterials of the invention, i.e., a pre-cure biomaterial, or a fatty acid-based, pre-cure-derived biomaterial can be used in the form of an emulsion. An "emulsion," which is a type of suspension, is a combination of two or more immiscible liquids in a particular energetically unstable state. Although an emulsion can be a combination of more than two immiscible liquids, for the sake of clarity, the following explanation will be presented assuming an emulsion of only two liquids. The first liquid is dispersed or suspended in a continuous phase of the second liquid. This may be thought of as "droplets" of the first suspended liquid distributed throughout a continuous "pool" of the second liquid. The first liquid can include a mixture of any number of miscible liquids and the second liquid can include a mixture of any number of miscible liquids as long as the mixture of the first liquid is immiscible with respect to the mixture of the second liquid. One of ordinary skill in the art will appreciate that emulsions can be formulated using a combination of three or more immiscible liquids, and although such embodiments are not described further herein, they are considered to fall within the scope of the present invention.

Various aspects and embodiments of the present invention are further described by way of the following Examples. The Examples are offered by way of illustration and not by way of limitation.

EXAMPLES

The following examples characterize the novel fatty acid-derived biomaterial chemistry described herein and illustrate some of the boundaries associated with the chemical mechanisms of formation and how alteration of those mechanisms influences the properties (e.g., therapeutic benefits and/or drug release profile) of the final product. The identity of some of the hydrolysis products are identified through in-vitro experiments and correlated with in-vivo experiments to demonstrate the ability for the coating or stand-alone film to be bioabsorbed. Finally, examples showing the utility of the fatty acid-derived biomaterials described herein in drug delivery applications on coronary stents and hernia mesh devices are presented.

The following examples are for demonstration purposes and are not meant to be limiting.

Example 1: Analysis of In-Vitro Hydrolysis Chemistry of a Novel Biomaterial Derived from Fish Oil in 0.1 M PBS Solution In the following example, coated medical devices (e.g., a polypropylene mesh) were cured in a high airflow oven at 200° F. for 24 hours, after which the fish oil was converted into a cross-linked biomaterial gel coating encapsulating the polypropylene mesh by oxidation of the C═C bonds present in the fish oil resulting in the formation of oxidative byproducts (i.e., hydrocarbons, aldehydes, ketones, glycerides, fatty acids) while largely preserving the esters derived from the original oil triglycerides. Volatilization of the byproducts followed by the formation of ester and lactone cross-links result in the solidification of oil into a bioabsorbable hydrophobic cross-linked biomaterial. The ability for the coating to be slowly hydrolyzed was investigated using 0.1 M PBS solution. The PBS solution was analyzed using GC-FID fatty acid profile and GPC chromatographic measurements after hydrolysis of the oil-derived biomaterial in PBS for 30 days.

Figure 11:
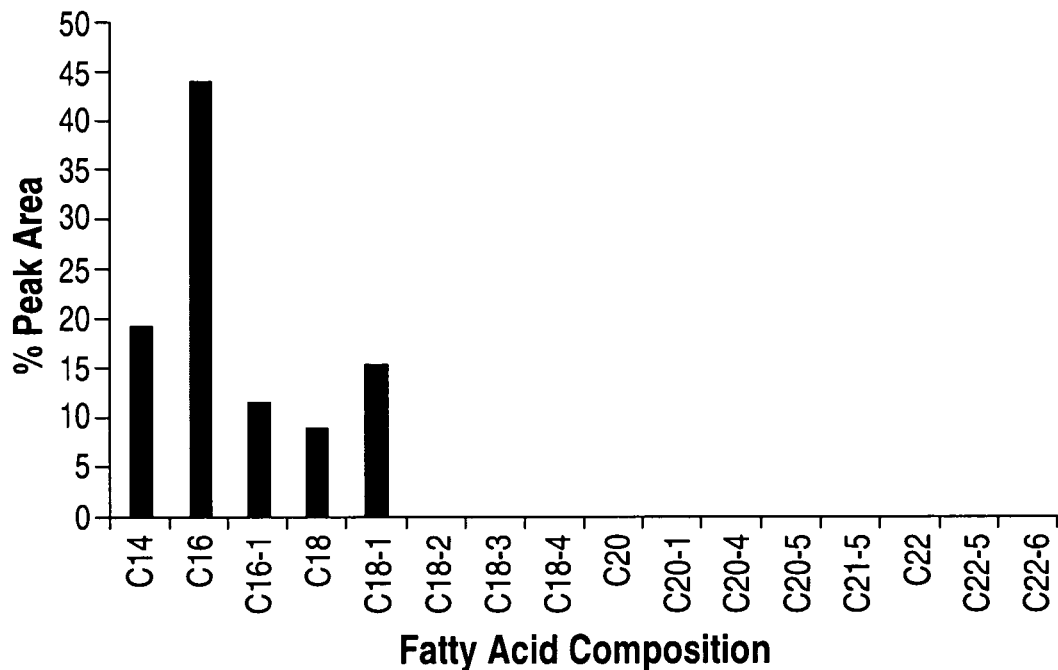
FIG. 11 provides the GC-FID fatty acid profile from a 0.1 M PBS solution after 30 day exposure of a totally cured biomaterial (no pre-cure component) as described in Example 1.

FIG. 11 summarizes the fatty acid profile results obtained after drying the PBS solution and then performing a GC-FID fatty acid profile analysis as described in the AOCS official method Ce 1-89b to identify the fatty acids present in solution. FIG. 11 shows that the fatty acids identified from the PBS solution are the same as those detected from the coating itself. GPC analysis was also conducted on the hydrolysis solution and the results are summarized in Table 5. The GPC results showed that the vast majority of molecular weight components identified (80%) were below a molecular weight of 500, which is consistent with the fatty acid components of the coating. Also, glyceride components of the coating could be identified with molecular weights around 1000 (15% of the coating). The GPC results also showed a negligible amount (approximately 4%) of high molecular weight gel. The GPC results support the other analytical characterization experiments on the oil-derived coatings which show that the oil-derived biomaterial is comprised of cross-linked glycerides and fatty acids, and that the majority of the coating is non-polymeric (i.e., approximately 80% of the components identified had a molecular weight of less than 500).

TABLE 5

GPC Analysis of PBS Hydrolysis Solution after Contact with Fish Fatty acid-Derived Biomaterial for 30 days.

| Molecular Weight | % Peak Area | Potential Identity |
| --- | --- | --- |
| >110,000 | 4 | High Molecular Weight Gel |
| >1000 | 1 | Partially Hydrolyzed Gel |
| 1000 | 15 | Glycerides |
| <500 | 80 | Fatty Acids |

Figure 13:
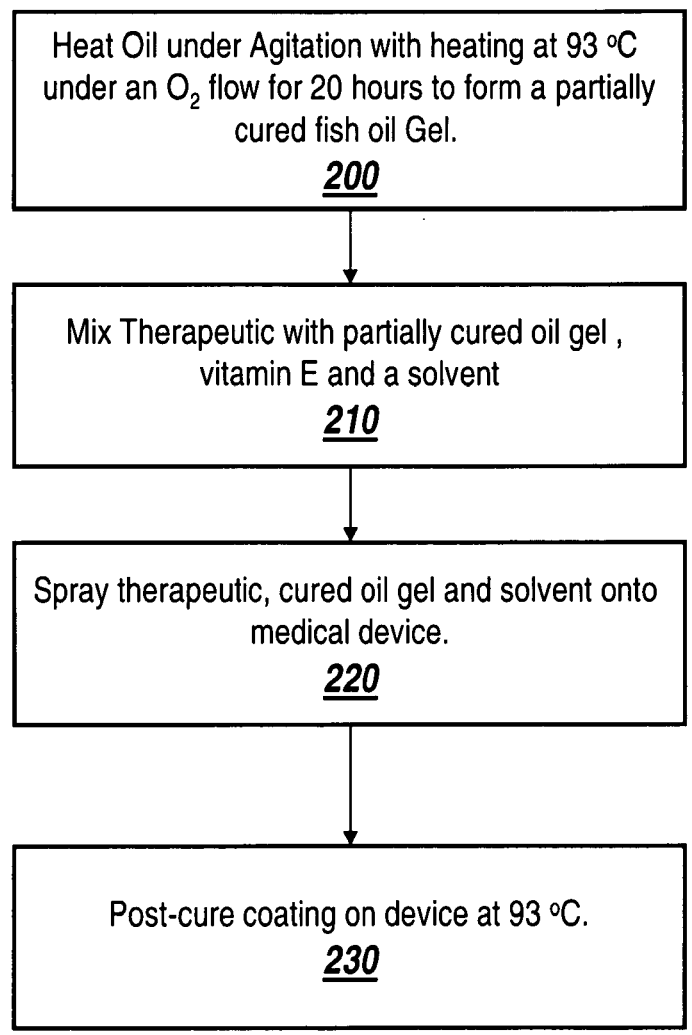
FIG. 13 depicts a flow diagram presenting the process to create a fatty-acid based, pre-cure-derived coating on a stent loaded with a therapeutic is outlined in Example 2.
Figure 14:
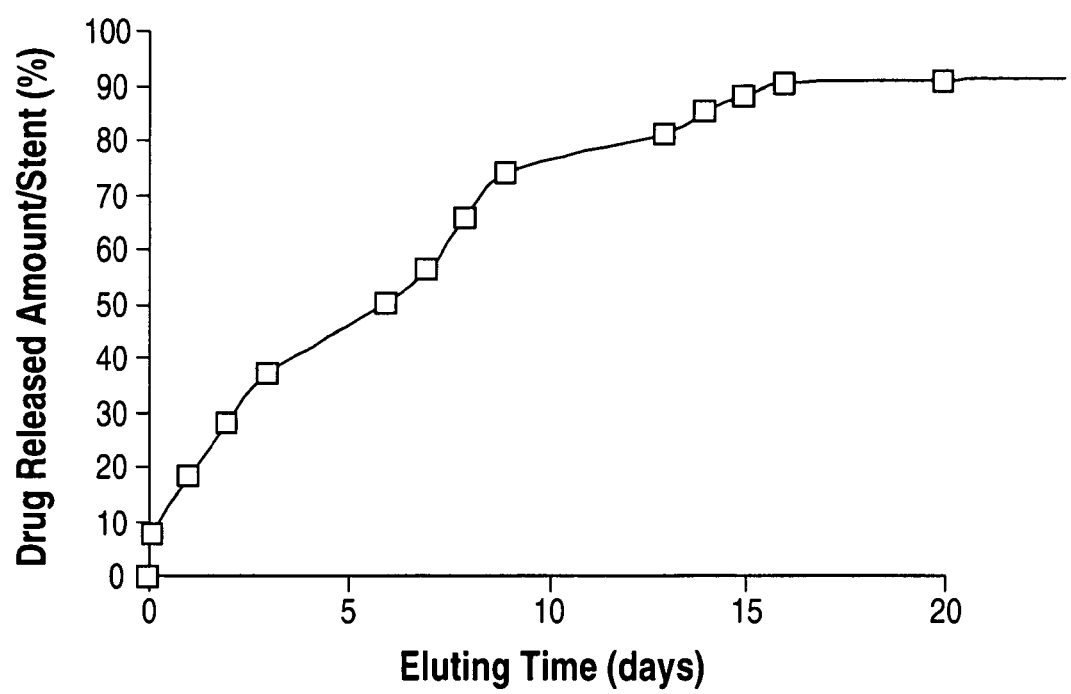
FIG. 14 shows the drug release profile for a cured oil therapeutic coating in 0.01 M PBS buffer as described in Example 2.

Example 2: Fatty Acid Based, Pre-Cure Derived Coatings Loaded with Therapeutics and Applied to Metallic Stents In this particular embodiment of the present invention, the application of cured oil coatings loaded with a therapeutic and applied to a cardiac stent are presented. The flow diagram presenting the process to create a cured coating on a stent loaded with a therapeutic is outlined in FIG. 13. Briefly, a pre-cured fish oil coating is created in a reaction vessel under agitation with heating in the presence of oxygen at 200° F. for 20 hours. The coating is mixed with the therapeutic of interest, and vitamin E with a solvent and then sprayed onto the stent to create a coating. The coating is annealed to the stent surface by heating at 200° F. for 7 hours to create a uniform coating. A coating with a model anti-inflammatory agent showed that this process allowed for 90% of the drug to be recovered after curing as determined using extraction of the drug from the device with HPLC analysis. FIG. 14 shows the drug release profile for this coating in 0.01 M PBS buffer going out to 20 days with over a 90% recovery of the drug using this process.

Example 3: Controlled Release of the Fatty Acid Based, Pre-Cure Derived Coating Drug release was quantified for 3 batches of 16 mm stainless steel stents, coated with a Compound C drug coating formulation consisting of 60% Compound C, 30% pre-cured Fish Oil, 10% tocopherol Pre-cured fish oil was produced using fish oil, pre-cured at 93° C., to achieve a pre-cure viscosity of $1.3 \times 10^5$ cps as measured at 22° C. The coating was applied to surface of a 16 mm Atrium Flyer stainless steel stent by spraying to achieve an overall stent drug load of approximately 100 μg of Compound C per stent. The coated stents were subjected to a second thermal cure process whereby the coating was post-cured in an oven at 93° C. for a period of 7.5 hours. Dissolution was carried out in a 4 ml solution containing 0.01M purified buffered saline (PBS) at a temperature of 37° C.

Figure 15:
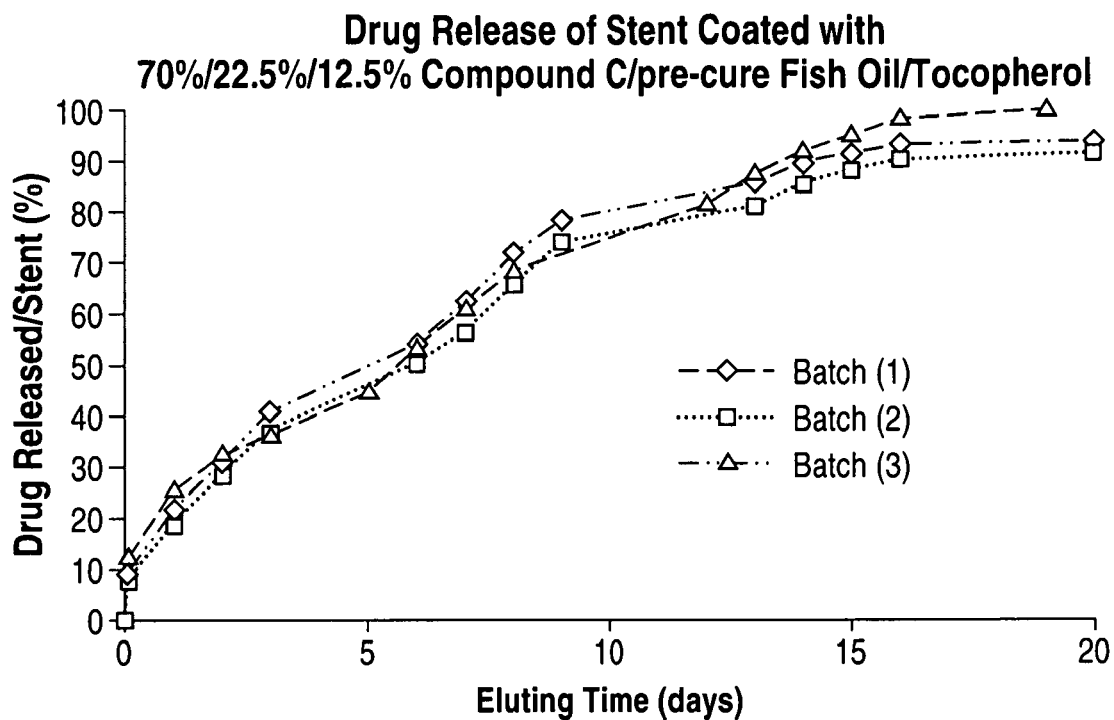
FIG. 15 shows the drug release profile for the fatty-acid based, pre-cure-derived biomaterial described in Example 3.

An HPLC method was used to quantify drug dissolution in vitro of the Compound C drug coated stent. The drug release profile data is shown in FIG. 15, which illustrates that the drug release from the Compound C drug coating extends over a period of 20 days and that the release profile is reproducible from batch to batch.

Example 4: Trackability Forces for Bare Metal, Coated and Drug Coated Stent

Device trackability forces were quantified for 3.0 mm×13 mm CoCr stents mounted on a balloon catheter. Trackability forces were quantified for 3 distinct stent coating groups, a bare metal CoCr stent, a CoCr stent coated with a 75% pre-cured fish oil, 25% tocopherol coating and a CoCr stent coated with a 60% Compound B, 22.5% pre-cured fish oil, 12.5% tocopherol coating. Pre-cured fish oil was produced using fish oil, pre-cured at 93° C., to achieve a pre-cure viscosity of $1.0 \times 10^6$ cps as measured at 22° C. The fatty acid-derived, pre-cured biomaterial was prepared by dissolving 75% pre-cured fish oil with 25% tocopherol in MTBE solvent to achieve a 1% solids formulation. The formulation is vortexed for 1 minute at 3000 RPM. The formulation is then applied to the stent via a spray process to achieve a total stent coating weight of approximately 167 μg. The coated stents are subjected to thermal post-curing at 93° C. for 6 hours. Following the post-curing process, the stents are crimped onto balloon catheters to achieve a stent profile dimension of approximately 0.04 inches using a 12 point crimping instrument exerting compressive loads of between 16 and 22 psi. The Compound B, pre-cured fish oil, tocopherol formulation was prepared by dissolving 75% pre-cured fish oil with 25% tocopherol in MTBE solvent to achieve a 25% solids formulation. A quantity of Compound B is weighed out in a proper glass vial and a volume of the pre-cured FO and tocopherol formulation is added into the glass vial to achieve a 60% Compound B, 40% pre-cure fish oil-tocopherol ratio. Additional MTBE is added to the glass vial to achieve a total solids ratio of 1%. The formulation is vortexed for 1 minute at 3000 rpm. The formulation is then applied to the stent via a spray process to achieve a total stent coating weight of approximately 167 μg. The coated stents are subjected to thermal post-curing at 93° C. for 6 hours. Following the post-curing process, the stents are crimped onto balloon catheters to achieve a stent profile dimension of approximately 0.04 inches. Catheters with stents mounted over the balloon segment are then threaded through a 6Fr Medtronic Launcher guide catheter inserted within a torturous path consisting of an anatomical model containing 2 bends having radii of 22 mm and 14 mm with a total set travel distance of 395 mm. De-Ionized water was used as the test environment. Forces are measured by a load cell on the mechanism used to drive the catheter forward.

Figure 16:
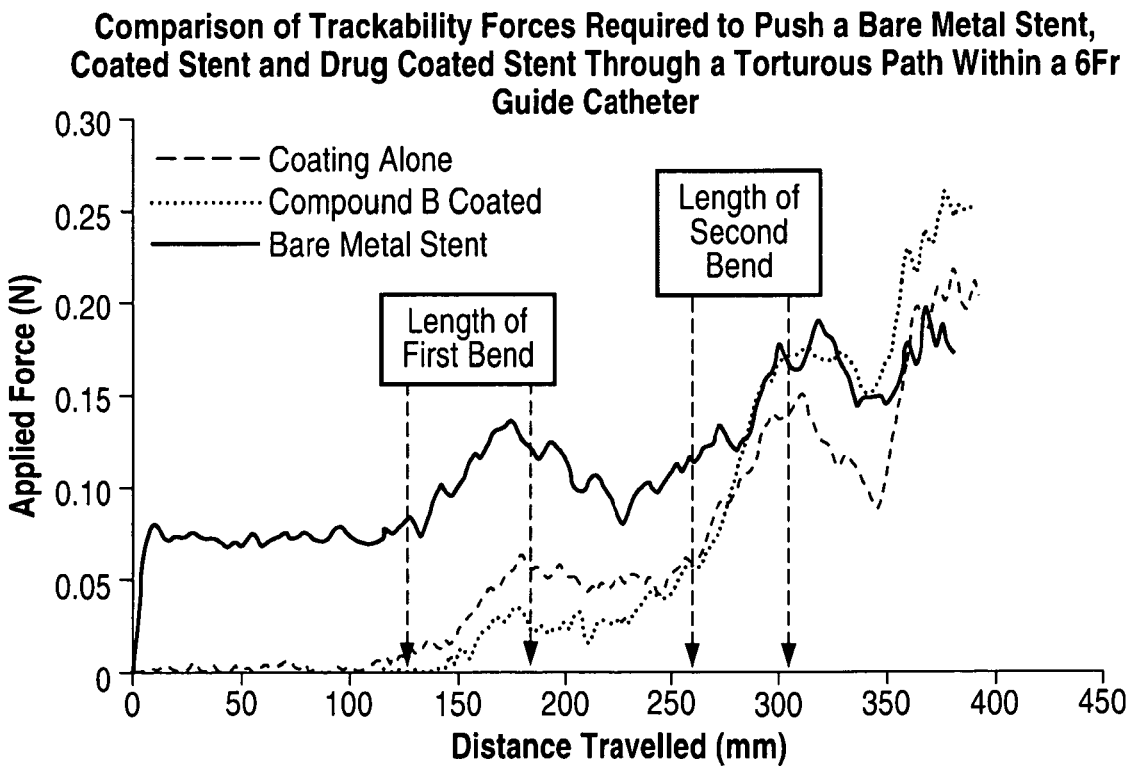
FIG. 16 shows trackability force data for the fatty-acid based, pre-cure-derived biomaterial described in Example 4.

Trackability force data is shown in FIG. 16. This data indicates lower overall trackability forces required to push the devices incorporating the fatty acid-derived, pre-cured biomaterial coating containing tocopherol, Compound B and pre-cured fish oil as compared to the bare metal stent, suggesting that the coatings substantially reduce the coefficient of friction of the stent surface and subsequently the frictional forces between the stent and the guide catheter wall during the process of advancing the balloon catheter within the guide catheter through a torturous pathway.

Example 5: Post Curing Time and Temperature Affects on Mechanical Properties

The effects of post curing time and temperature on coating mechanical properties were evaluated in a study in which CoCr stents were coated with an oil-derived, pre-cured biomaterial coating of Compound B/pre-cured fish oil/tocopherol.

CoCr stents were pre-cleaned with acetone, and coated with a formulation of 60% Compound B, 30% pre-cured fish oil, 10% tocopherol. The Compound B, pre-cured fish oil, tocopherol formulation was prepared by dissolving 75% pre-cured fish oil with 25% tocopherol in MTBE solvent to achieve a 25% solids formulation. A quantity of Compound B is weighed out in a glass vial and a volume of the pre-cured FO and tocopherol formulation is added into the glass vial to achieve a 60% Compound B, 40% pre-cure fish oil-tocopherol ratio. Additional MTBE is added to the glass vial to achieve a total solids ratio of 1%. The formulation is vortexed for 1 minute at 3000 RPM. The formulation is then applied to the stent via a spray process to achieve a total stent coating weight of approximately 167 μg. The coated stents were then subjected to thermal post-curing process at temperatures ranging from 60° C. to 100° C.

Following the post-curing process, the stents are crimped onto balloon catheters using a twelve point crimping instrument to achieve a stent profile dimension of approximately 0.043 inches, requiring 16-22 psi of crimping pressure. Subsequently, the balloon catheters were inflated in air to a nominal inflation pressure of 9 atm. Following crimping and expansion the drug coating is evaluated visually for physical damage. The results of this testing demonstrate that stents post cured at temperatures above 80° C. show substantially less coating damage following crimping and subsequent expansion than stents post cured at 80° C. or less, demonstrating that mechanical properties of the coating can be significantly altered by changing the final cross link density of the coating by altering the temperature at which the coating is post cured.

Figure 18:
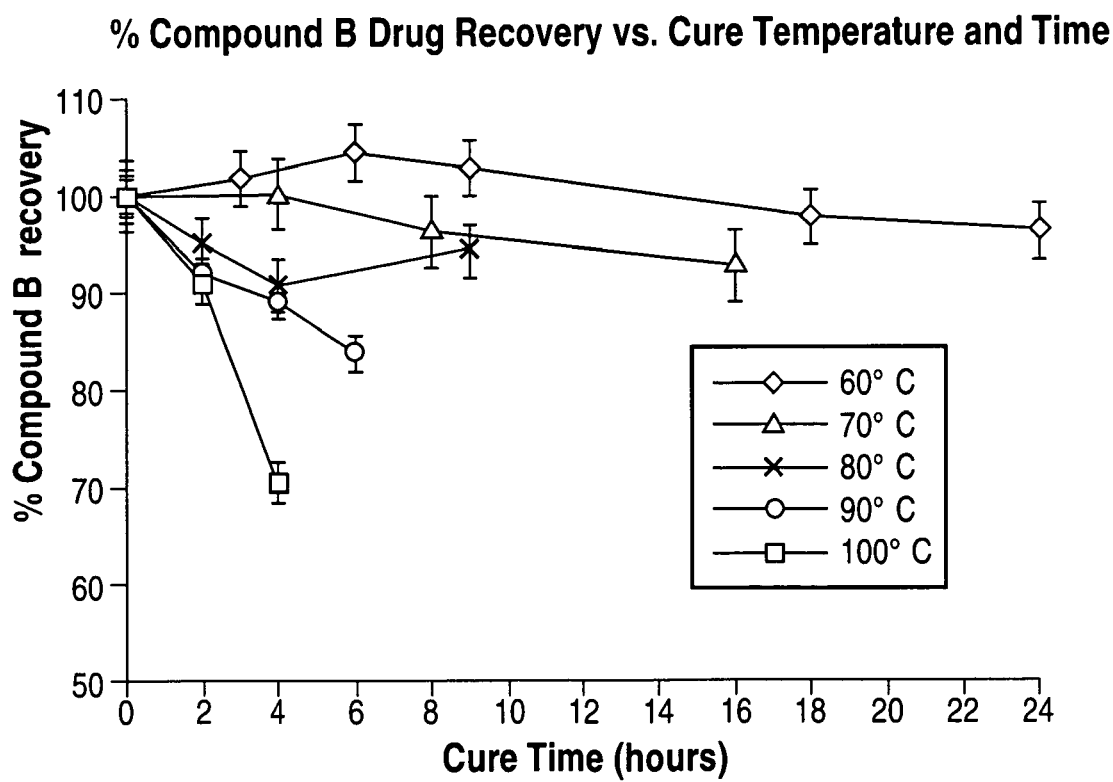
FIG. 18 shows the drug recovery for the fatty-acid based, pre-cure-derived biomaterial described in Example 4.

Example 6: Influence of Curing Time and Temperature on Drug Recovery of Thermally Sensitive Drugs The effect of curing time and temperature on drug recovery of a thermally sensitive drug incorporated within hydrophobic cross linked gel coating was evaluated and quantified. Pre-cured fish oil (PCFO) was prepared by heating fish oil in a reactor at 93° C. for a total of 26 hours, while infusing oxygen through a diffuser. The resultant viscosity of the pre-cured fish oil was $5 \times 10^6$ cps as measured at 22° C. The formulation consisting of 60% Compound B, 30% PCFO, and 10% Vitamin E was made by combining 3.76 g PCFO and 1.3 g Vitamin E to form a 75% PCFO, 25% Vitamin E base coating. 15.04 g methyl-tert-butyl-ether (MTBE) was added to produce a base coating solution of 75% solvent, 25% solids. This solution was vortexed for 30 min until clear. Next, 529 mg of the base coating solution was added to 198.8 mg Compound B. This mixture was diluted with 32.8 g methyl-tert-butyl-ether (MTBE) to produce a final solution of 1.0% solids for spray coating. CoCr stents (3.0×13 mm) were spray coated using an ultrasonic spray coating system (SonoTek, Inc.) with a target load of 100 μg Compound B. Each coated stent was weighed before coating and after coating to determine the actual weight of coating applied to each stent gravimetrically. Coated stents were subjected to oven post curing at a temperature range between 60° C. to 100° C. with post curing time ranging from 0 hrs to 24 hours. Following post curing the drug coating was extracted in a 100% acetonitrile solution and analyzed via HPLC to determine the drug concentration in solution from which the total drug mass extracted from the stent is determined. The total drug mass extracted from the stents along with the actual coating weight on the stent determined gravimetrically is used to calculate the percent of drug applied to the stent in coating which is recovered following the post curing process. Percent drug recovery data is shown in FIG. 18. This data illustrates that 100% of the drug is recovered after spray coating the stent and prior to post curing. However, drug recovery drops with post curing and as post curing time increases. The data also shows that the rate at which drug recovery drops over time is directly influenced by the temperature at which post curing is carried out.

Example 6A: Influence of Curing Time on the Crosslink Density of a Pre-Cured Fish Oil as Measured by Viscosity The effect of curing time on pre-cured fish oil viscosity was evaluated and quantified. Pre-cured fish oil (PCFO) was prepared by heating fish oil (Ocean Nutrition 18/12TG fish oil) in a reactor at 93° C. for a total of 33 hours, while infusing oxygen through a diffuser. During this reaction, oxidation of the oil occurs and cross links are formed. The duration of the reaction directly influences the extent of oxidation and cross linking that occurs, and results in an increase in viscosity of the oil over time during the reaction. Thus the final viscosity of the pre cured fish oil can be correlated to the extent of cross linking and oxidation. Fish oil was reacted at 93° C. with oxygen for 23 h, 26 h, 30.5 h, and 33 h. Viscosity was measured at 22° C. The results (FIG. 19) show an increase in viscosity corresponds to longer reaction times and thus indirectly confirm that increase crosslink density associated with higher viscosities also increases with the time of curing.

Example 7: Method of Producing a Fatty Acid Based, Pre-Cure Derived Coating on a Stent Using the Therapeutic Agent Compound C Pre-cured fish oil (PCFO) was prepared by heating fish oil (Ocean Nutrition 18/12TG fish oil) in a reactor at 93° C. for a total of 23 hours, while infusing oxygen through a diffuser. The resultant viscosity of the pre-cured fish oil was $1 \times 10^6$ cps as measured at 22° C. The Compound C drug coating formulation consisting of 70% Compound C, 22.5% PCFO, and 7.5% Vitamin E (DSM Nutritional Products) was made by combining 3.7561 g PCFO and 1.2567 g Vitamin E to form a 75% PCFO, 25% Vitamin E base coating. 15.04 g methyl-tert-butyl-ether (MTBE) was added to produce a base coating solution of 75% solvent, 25% solids. This solution was vortexed for 30 min until clear. Next, 767.6 mg of the base coating solution was added to 447.8 mg Compound C. This mixture was diluted with 7.84 g methyl-tert-butyl-ether (MTBE) to produce a final solution of 7.6% solids for spray coating. Atrium Cinatra™ CoCr stents (3.5×13 mm) were spray coated using a Badger airbrush equipped with a medium sized needle. The target coating load was 100 μg Compound C per stent. Each stent was spray coated for 1.5 seconds using an air pressure of 30 psi, while the stent was rotated. This yielded an average coating load of 95.2 μg Compound C. Coated stents were cured in an oven set to 93° C. for 7 hours. This process yields a conformal stent coating having a smooth surface characteristic when imaged using scanning electron microscopy (SEM). FIG. 20A is an SEM of the Compound C drug coated stent at 50× magnification following 7 hours of post curing at 93° C.

Example 8: Method of Producing a Fatty Acid Based, Pre-Cure Derived Coating on a Stent Using Therapeutic Agent Compound B Pre-cured fish oil (PCFO) was prepared by heating fish oil (Ocean Nutrition 18/12TG fish oil) in a reactor at 93° C. for a total of 23 hours, while infusing oxygen through a diffuser. The resultant viscosity of the pre-cured fish oil was $1 \times 10^6$ cps. The formulation consisting of 60% Compound B, 30% PCFO, and 10% Vitamin E (DSM Nutritional Products) was made by combining 3.7582 g PCFO and 1.2562 g Vitamin E to form a 75% PCFO, 25% Vitamin E base coating. 15.04 g methyl-tert-butyl-ether (MTBE) was added to produce a base coating solution of 75% solvent, 25% solids. This solution was vortexed for 30 min until clear. Next, 529 mg of the base coating solution was added to 198.8 mg Compound B. This mixture was diluted with 32.8 g methyl-tert-butyl-ether (MTBE) to produce a final solution of 1.0% solids for spray coating. CoCr stents (3.0×13 mm) were spray coated using an ultrasonic spray coating system (SonoTek, Inc.) with a target load of 100 μg Compound B. Coated stents were cured in a 93° C. oven for 6 hours. This process yields a conformal stent coating having a smooth surface characteristic when imaged using scanning electron microscopy (SEM). FIG. 20B is an SEM of the Compound B drug coated stent at 50× magnification following 6 hours of post curing at 93° C.

Example 9: Simulation of the Chemical Effects of the Fatty Acid Based, Pre-Cure Derived STent Coating Process on Individual Formulation Components Each individual formulation component (i.e., pre-cured fish oil, vitamin E, and Compound B) was studied before and after final curing to understand the effects of the process on the chemistry of the Compound B oil-derived, pre-cured biomaterial coating. In this set of experiments, each individual component was sprayed on coupons after being diluted in methyl-tert-butyl-ether (MBTE) to mimic coated stents. The separate components were analyzed using appropriate spectroscopic and chromatographic techniques before and after final curing at 200° F. for six hours.

Figure 21A:
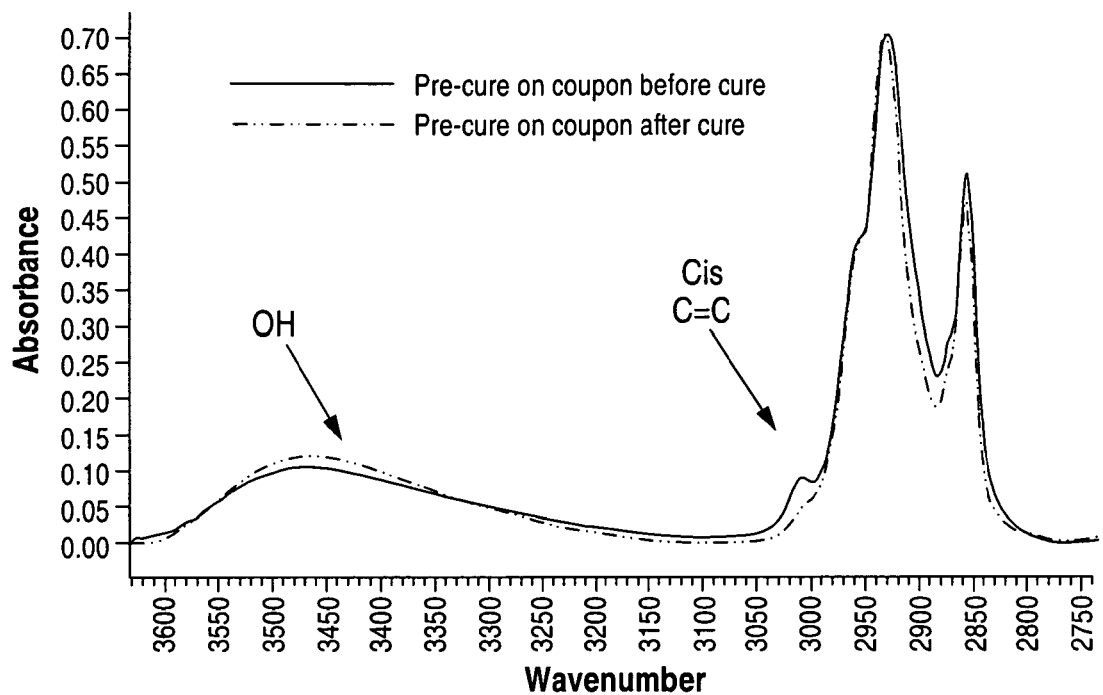
FIGS. 21A, 21B, and 21C shows FTIR analysis of pre-cured fish oil before and after curing.
Figure 21B:
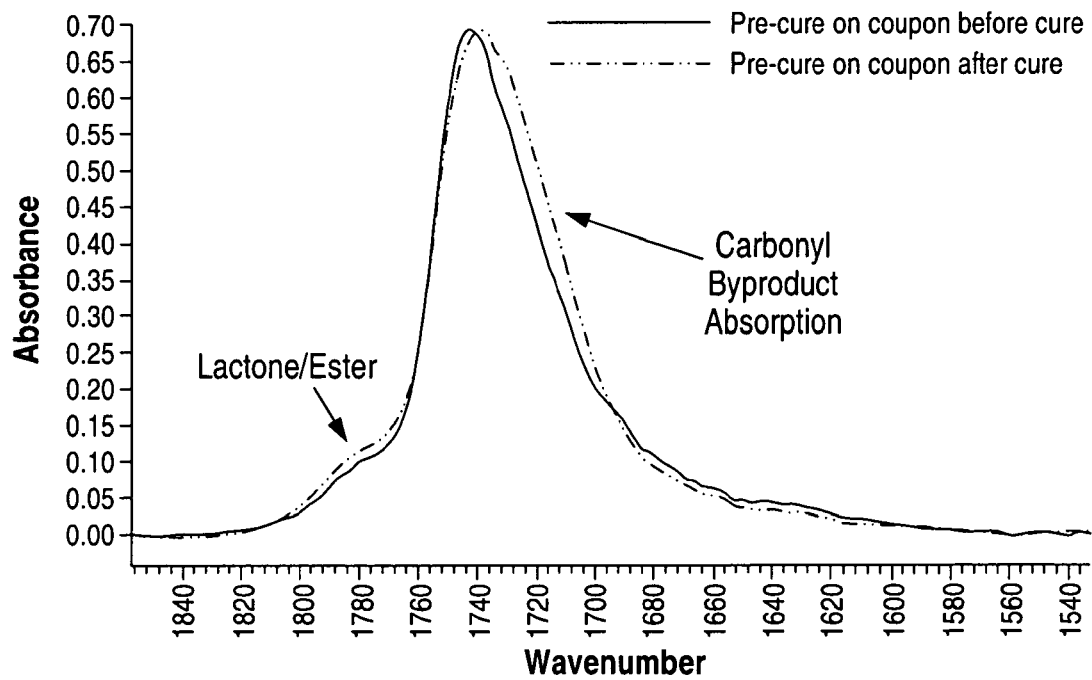
Figure 21C:
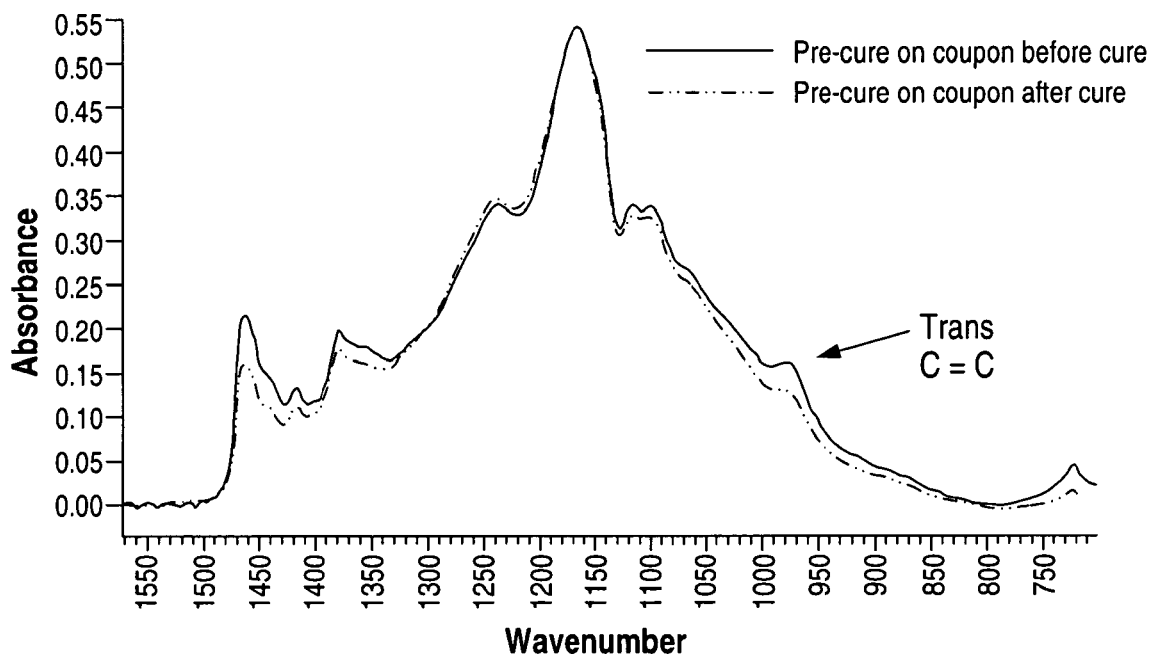
Figure 22:
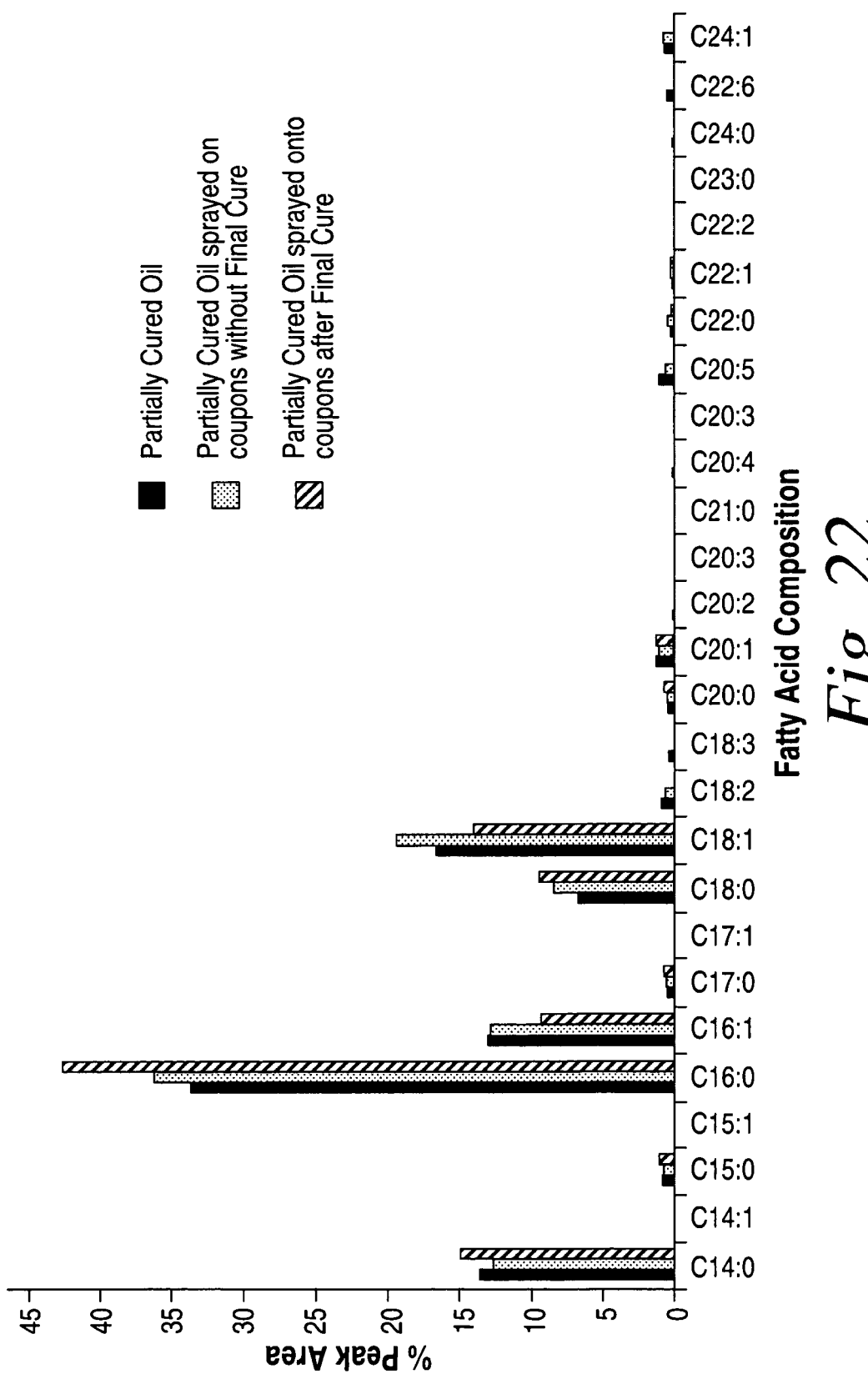
FIG. 22 shows GC fatty acid profile data acquired for a pre-cure fish oil sprayed onto coupons in MTBE before and after final curing.
Figure 23:
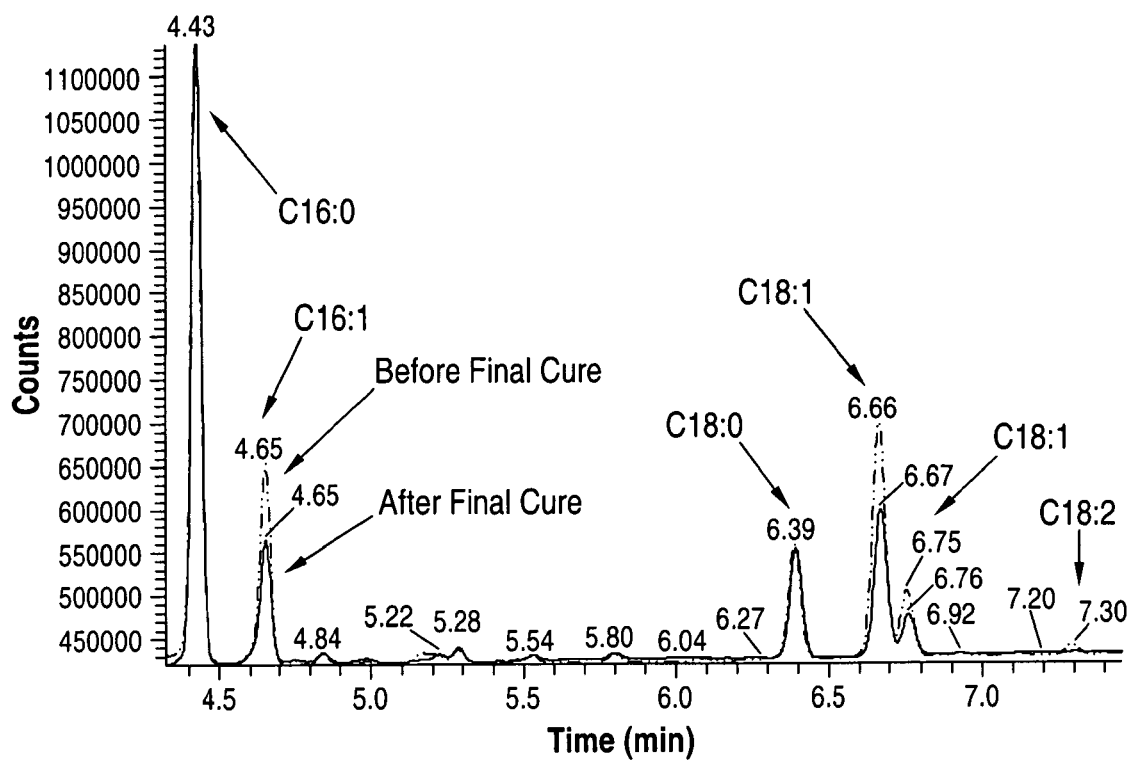
FIG. 23 shows a fatty acid profile chromatogram acquired for partially cured (i.e., pre-cure) fish oil sprayed onto coupons in MTBE before and after final curing.

The effects of dissolving pre-cured fish oil into MTBE solvent and spraying it onto a stainless steel coupon before and after final curing using FTIR analysis is presented in FIGS. 21A, 21B, and 21C. FTIR analysis of the pre-cured fish oil before and after curing reveals that the double bonds in the oil are oxidizing and forming lactone/ester cross-links resulting from the 6 hr curing process. Oxidation is evidenced by an increase in OH band absorption and a decrease in the cis and trans C=C peaks (FIGS. 21A and 21C), and broadening of the carbonyl peak indicating the formation of carbonyl byproducts (FIG. 21B). Evidence of cross-linking in the final cure is observed by the increase in the lactone/ester peak absorption band (FIG. 21B). GC fatty acid profile analysis of coupons is also consistent with oxidation of the oil before and after the final curing process. FIG. 22 presents the fatty acid compositional profile of pre-cured fish oil sprayed onto coupons before and after the curing process. The GC fatty acid profile results show a shift in the profile showing a reduction of unsaturated fatty acids and an increase in the saturated fatty acids after final curing (FIG. 22), which is consistent with oxidation of the unsaturated fatty acids. This result is also reflected in the pre and post curing GC chromatograms where the C16:1 and C18:1 unsaturated fatty acids peaks are reduced in the chromatogram (FIG. 23).

Figure 24A:
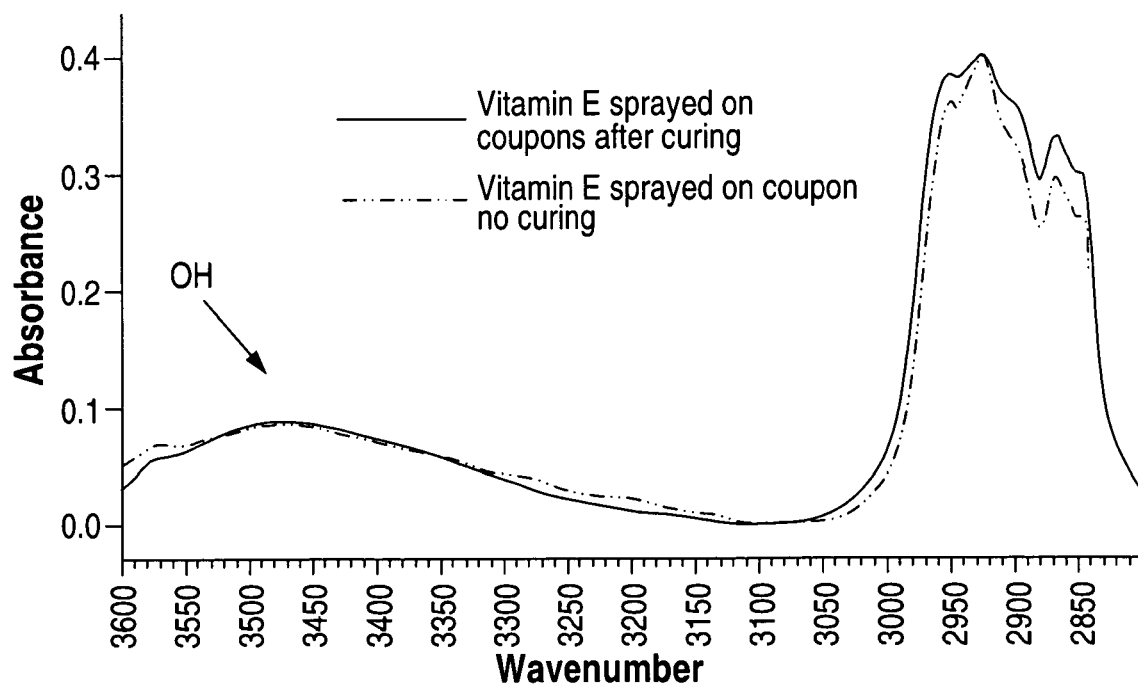
FIGS. 24A, 24B and 24C shows FTIR spectra of vitamin E dissolved in MTBE and sprayed onto coupons with and without final curing.
Figure 24B:
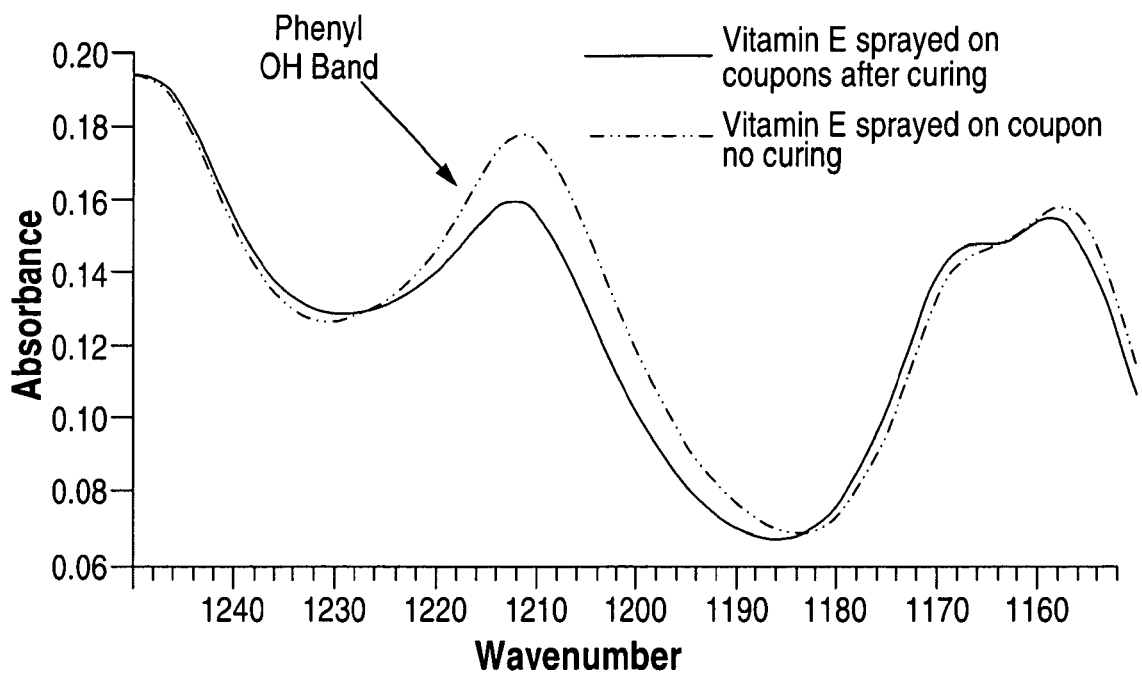
Figure 24C:
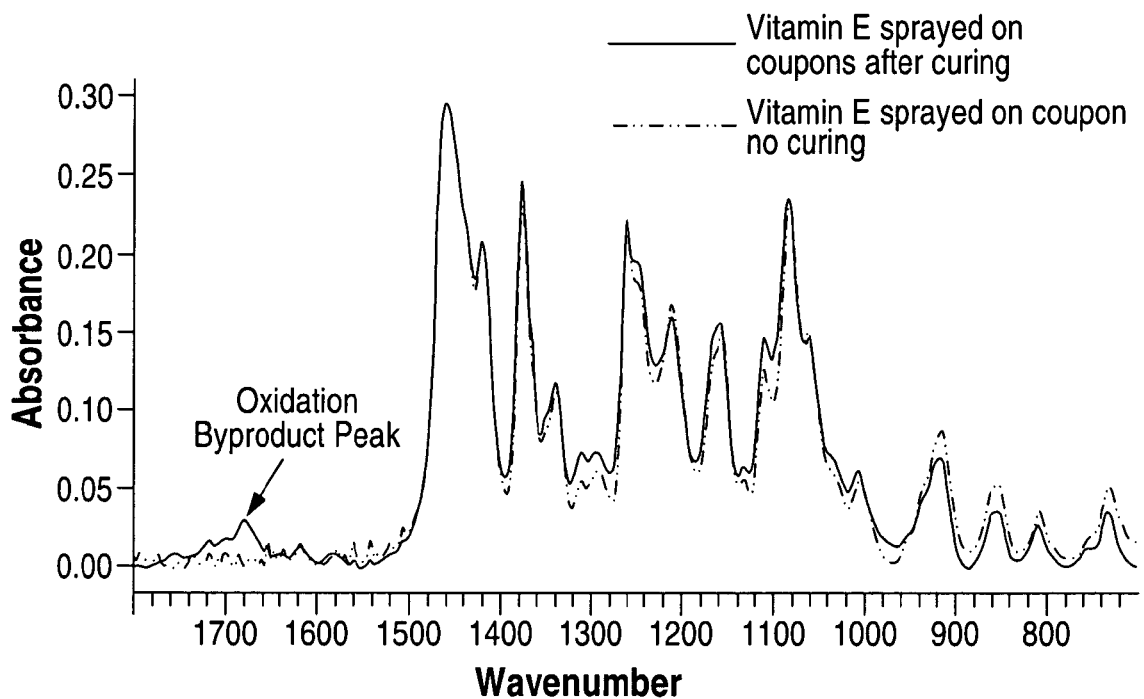
Figure 25A:
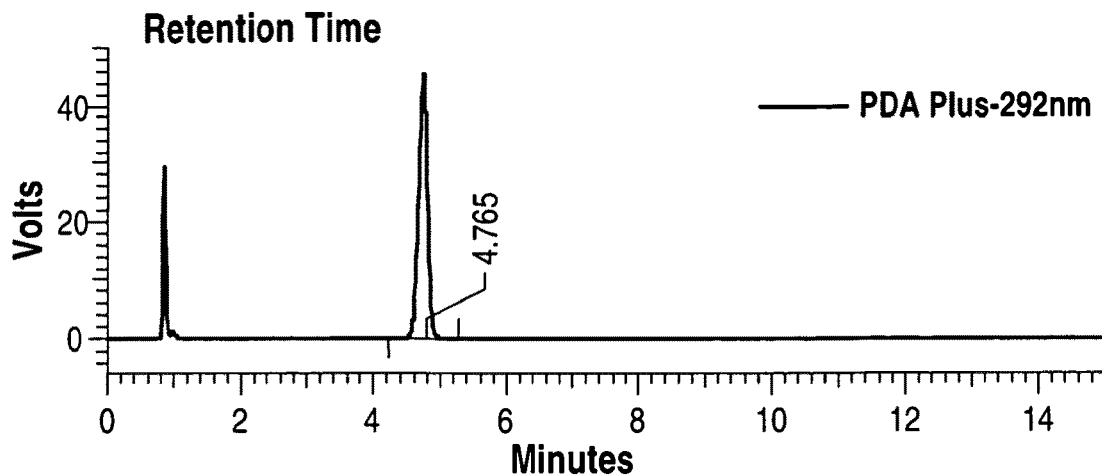
FIGS. 25A, 25B and 25C show HPLC chromatograms of a vitamin E control overlaid with vitamin E sprayed onto coupons before and after curing.
Figure 25B:
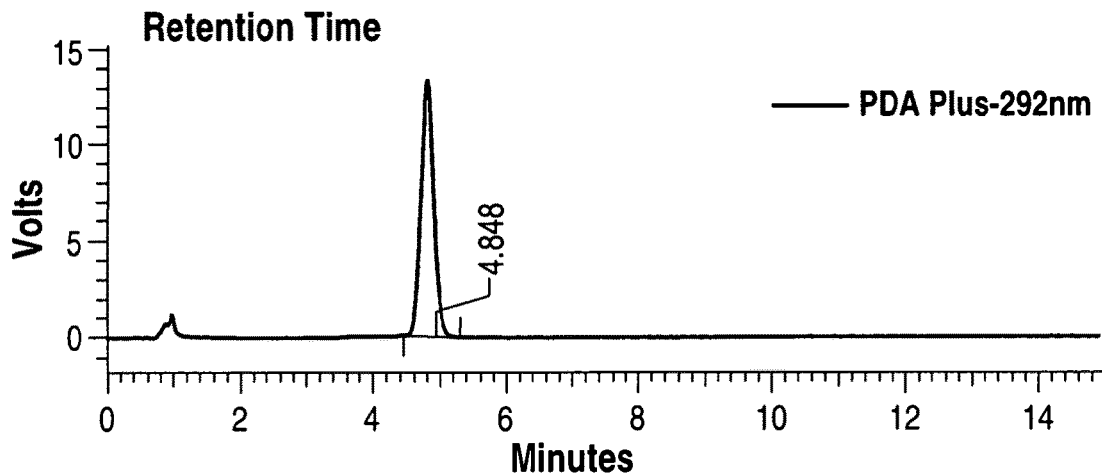
Figure 25C:
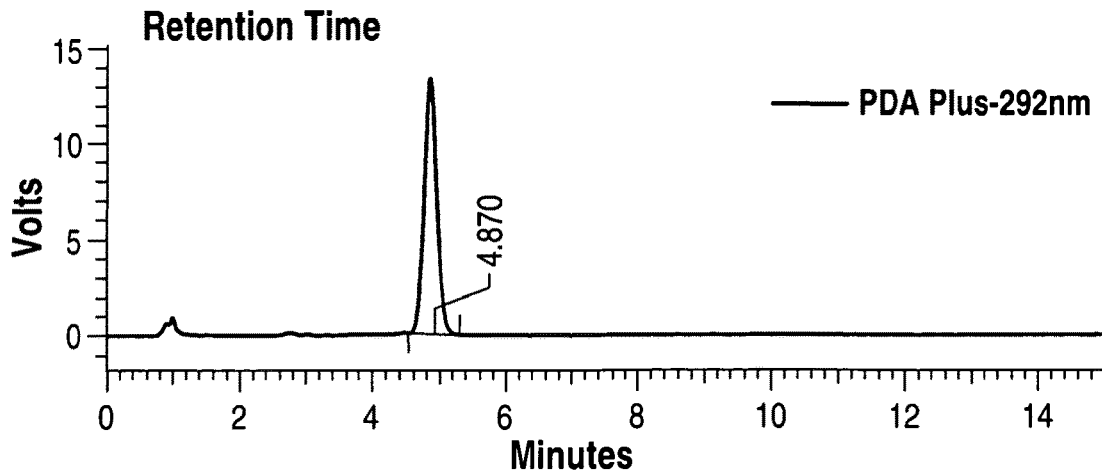

FTIR spectra of vitamin E dissolved in MTBE and sprayed onto coupons with and without final curing are presented in FIGS. 24A, 24B and 24C. FTIR results show that the final curing process results in oxidation which is supported by the formation of a peak at 1800-1600 $cm^{-1}$ (FIG. 24C). This result is further supported by the loss of the phenol OH absorption band after the final curing step (FIG. 24B), which occurs after oxidation of vitamin E. The vitamin E coated onto coupons before and after curing was extracted off the coupons and assayed by HPLC (Table 8). Each test represents an average of three samples. The results of this study show that when vitamin E is cured (i.e., oxidized) the recovery is reduced to 81%. HPLC chromatograms of a vitamin E control overlaid with vitamin E sprayed onto coupons before and after curing at 292 nm are presented in FIGS. 25A, 25B and 25C.

TABLE 8

Summary of Vitamin E HPLC Assay Results

| Sample Description | % Recovery |
| --- | --- |
| Vitamin E sprayed onto coupon in MTBE. | 96.2 |
| Vitamin E sprayed onto coupon in MTBE, after final cure. | 80.5 |

Figure 26A:
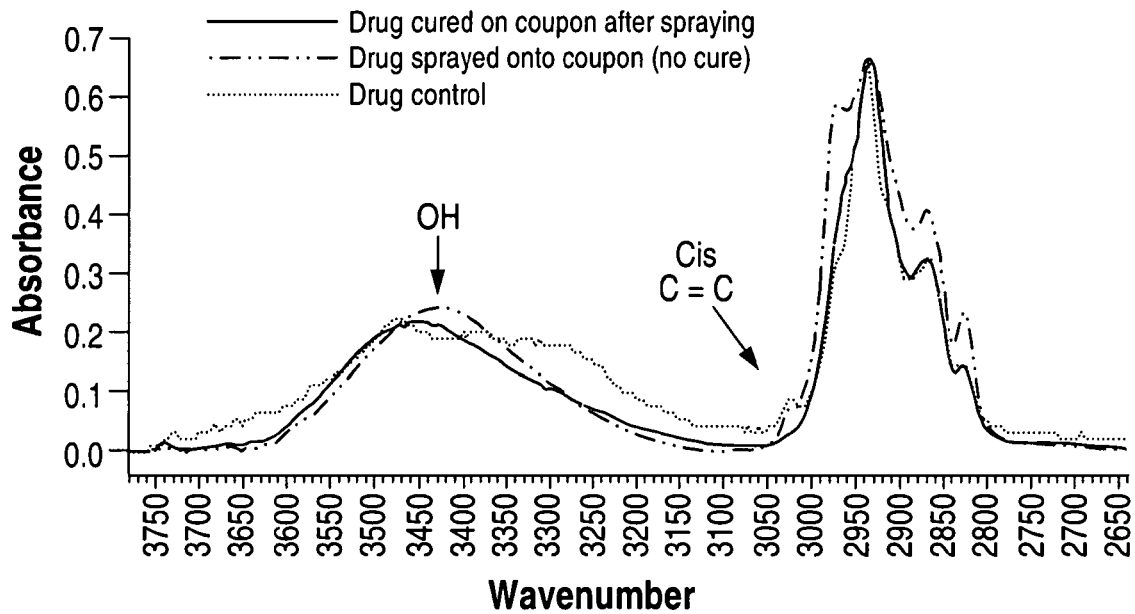
FIGS. 26A, 26B and 26C show FTIR analysis of a therapeutic agent after spraying onto coupons before and after curing.
Figure 26B:
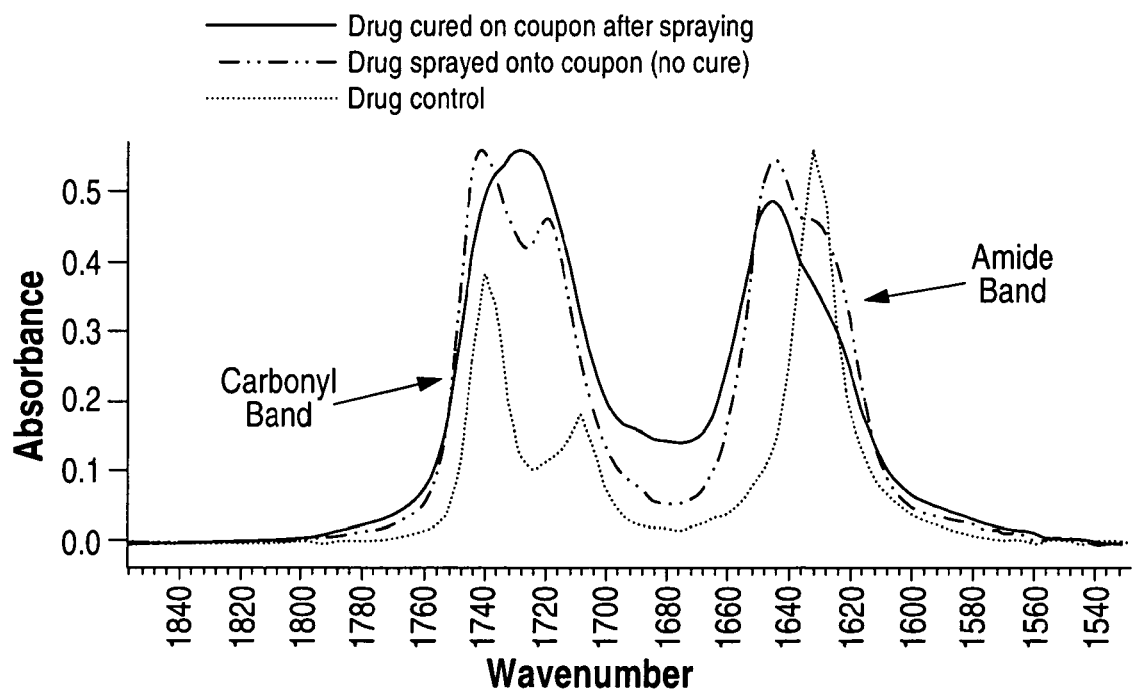
Figure 26C:
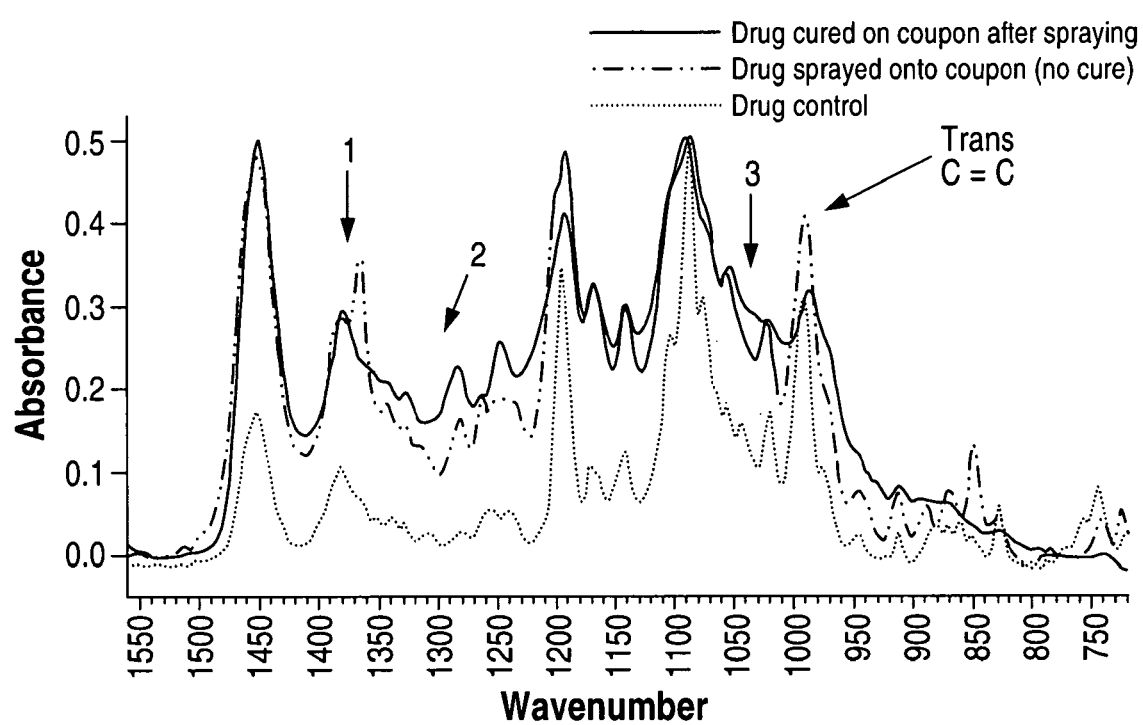

FTIR analysis of Compound B drug powder after spraying onto coupons before and after curing is presented in FIGS. 26A, 26B and 26C. FTIR reveals that dissolving Compound B in MBTE solvent and spraying it onto the coupons changes the conformation of the drug's structure in comparison to the control drug power spectrum. Specifically, the FTIR results show that following the spray process the amide band is shifted to the left and showing beginning signs of peak splitting in comparison to the Compound B powder control (FIG. 26B). This appears to correlate with the peak at ~1375 $cm^{-1}$ in the fingerprint region that has changed shape in comparison to the control sample (FIG. 26C, Peak1). There is also a peak that is formed that is not present in the control sample at ~1280 $cm^{-1}$ (FIG. 26C, Peak2). Following the curing of the Compound B samples several other spectral changes can be noted. The carbonyl band merges from two peaks into one peak (FIG. 26B). This peak is significantly broader than the Compound B powder control (FIG. 26B). Furthermore, the C—O peak at ~1025 $cm^{-1}$ disappears following the curing process (FIG. 26C, Peak3). These changes indicate a structural change in the Compound B as a result of curing. There is a change in the trans C=C triene peak at about 990 $cm^{-1}$ where it is greatly reduced in intensity after curing (FIG. 26C), which indicates that oxidation of the Compound B occurred. These changes indicate a structural change in the Compound B structure.

Figure 27A:
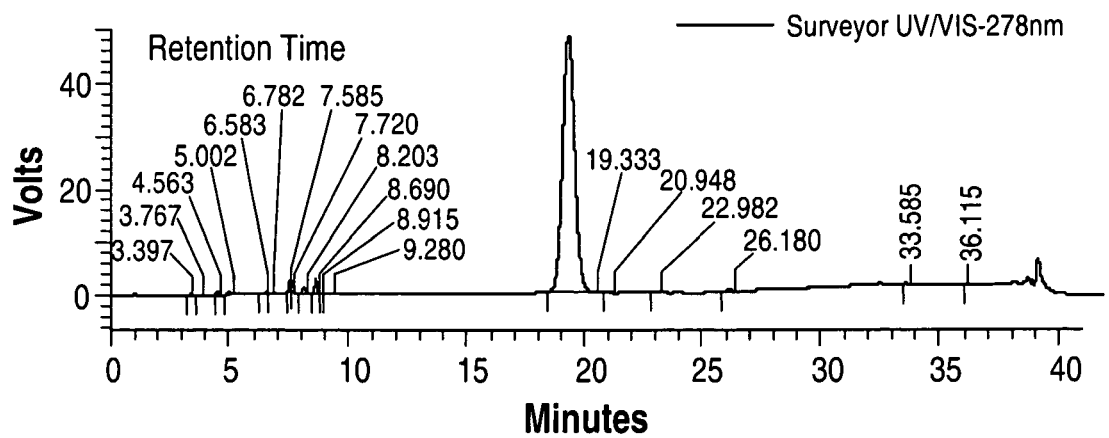
FIGS. 27A, 27B and 27C show HPLC chromatograms of a therapeutic agent after spraying onto coupons before and after curing.
Figure 27B:
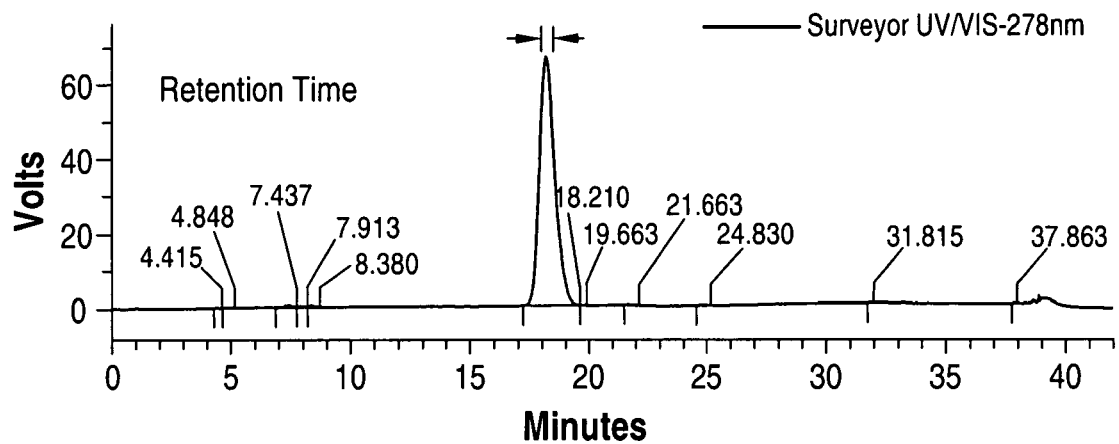
Figure 27C:
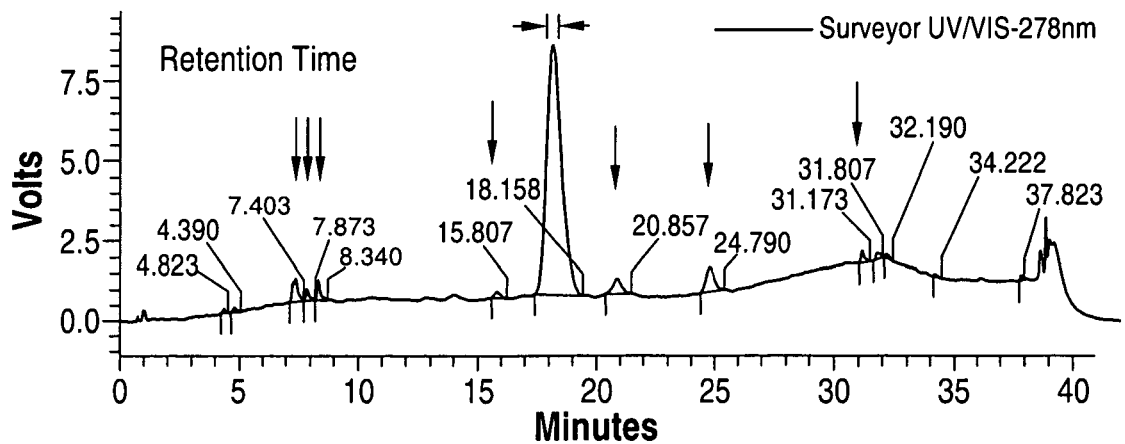

Assay of the Compound B drug load by HPLC reveals an equal recovery of the Compound B before and after spraying the Compound B onto coupons, before final curing. Upon inspection of the native chromatogram (FIG. 27B) there does not appear to be any significant degradation products formed after spraying. (FIG. 27A is the control.) However, following the curing process, the Compound B drug powder recoveries is reduced to approximately 9% (Table 9) and several new byproduct peaks are formed as detected by HPLC (FIG. 27C). These results are consistent with the FTIR data presented in FIG. 26C, which indicates that a degradation of the Compound B occurred after the final curing process.

TABLE 9

Summary of Compound B HPLC Assay Results

| Sample Description | % Recovery |
| --- | --- |
| Compound B Powder Control | 96 |
| Compound B sprayed onto coupon in MTBE, no final cure. | 90.6 |
| Compound B sprayed onto coupon in MTBE, after final cure. | 8.9 |

In summary, these studies showed that cured separately each component of the oil-derived biomaterial coating was oxidized during the curing process and specifically the Compound B therapeutic compound not in an oil-derived stent coating formulation was significantly degraded as a result of the curing process. This evidences the protective nature of the pre-curing process described herein in accordance with the present invention.

Figure 28A:
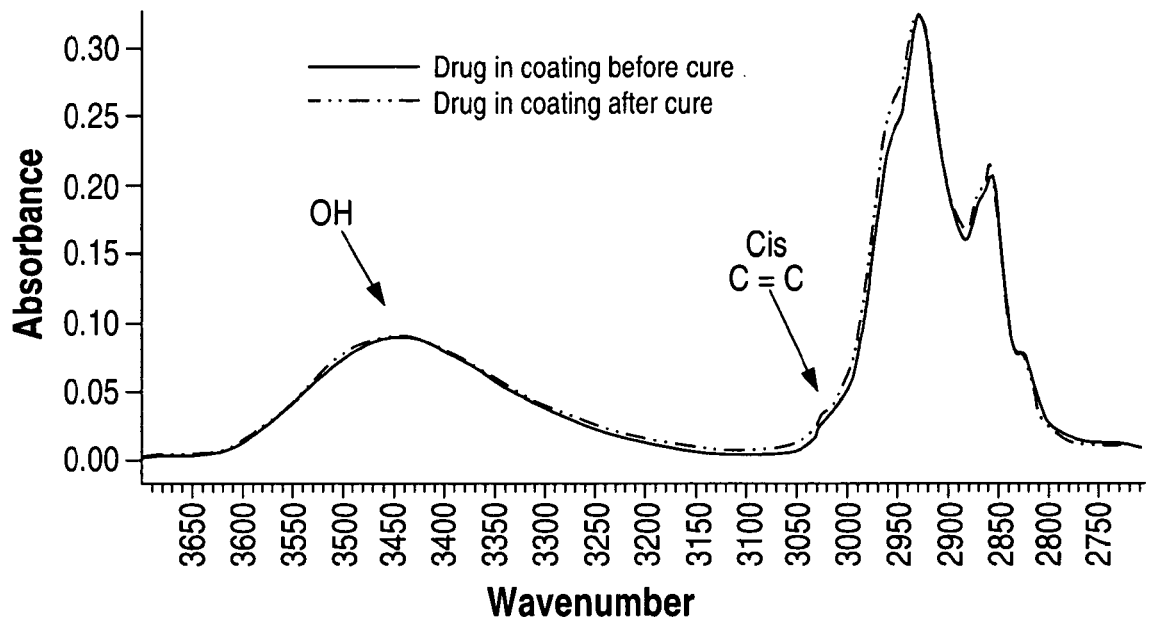
FIGS. 28A, 28B and 28C presents the FTIR spectra of the Compound B fatty acid-derived, pre-cured biomaterial coating before and after final curing.
Figure 28B:
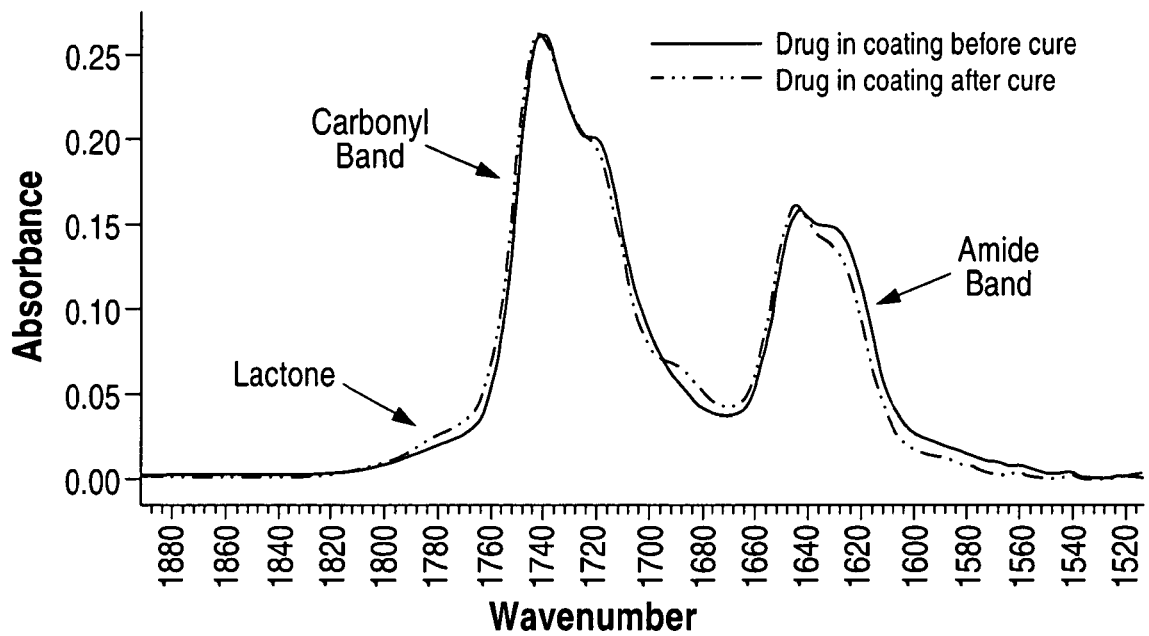
Figure 28C:
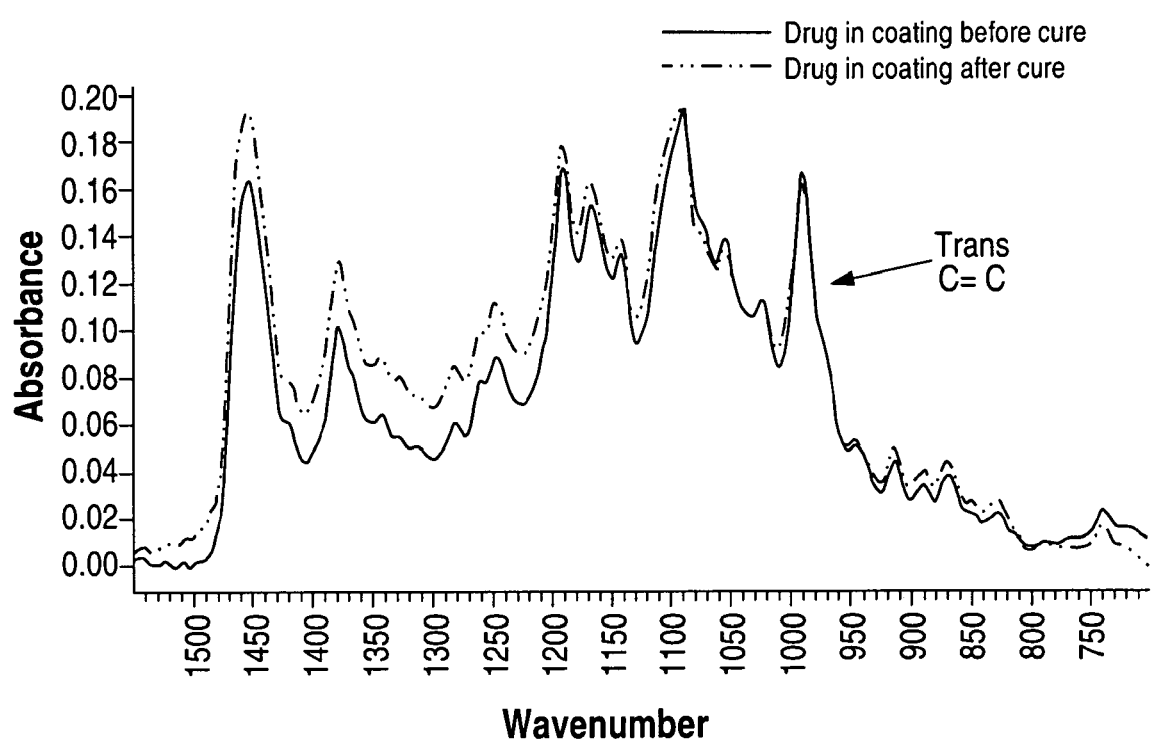

Example 10: Analysis of the Compound B Fatty Acid Based, Pre-Cure Derived Coating Formulation Components Combined and Sprayed onto Coupons In this series of experiments the changes in chemistry for each component in the Compound B oil-derived, pre-cured biomaterial coating was studied. The components were mixed together, sprayed onto coupons, and subjected to different stages of the stent coating manufacturing process. The 60% Compound B in 30% pre-cured fish oil, and 10% vitamin E was dissolved into MTBE and spray coated onto coupons. Samples were analyzed before and after final curing at 93° C. for 6 hours. FTIR, HPLC, and GC analyses were performed on the coatings. FIGS. 28A, 28B and 28C present the FTIR spectra of the Compound B oil-derived, pre-cured biomaterial coating before and after final curing. Interestingly, there are few spectral changes in the spectrum after final curing, especially in functional groups assigned to the Compound B therapeutic compound. Specifically there are no apparent intensity changes in the trans C=C band and there does not appear to be any significant changes in structure in the FTIR fingerprint region (FIG. 28C). The biggest difference in the Compound B biomaterial coating after heating is an increase in absorption around 1780 $cm^{-1}$, which is consistent with lactone/ester cross-linking of the fish oil component of the curing, and which was also observed with the fish oil by itself after curing (FIG. 21B). These results contrast those results obtained for the Compound B powder alone where significant structural changes were noted after final curing (FIG. 26) and show that Compound B is more chemically stable mixed in the oil-derived biomaterial formulation.

Figure 29A:
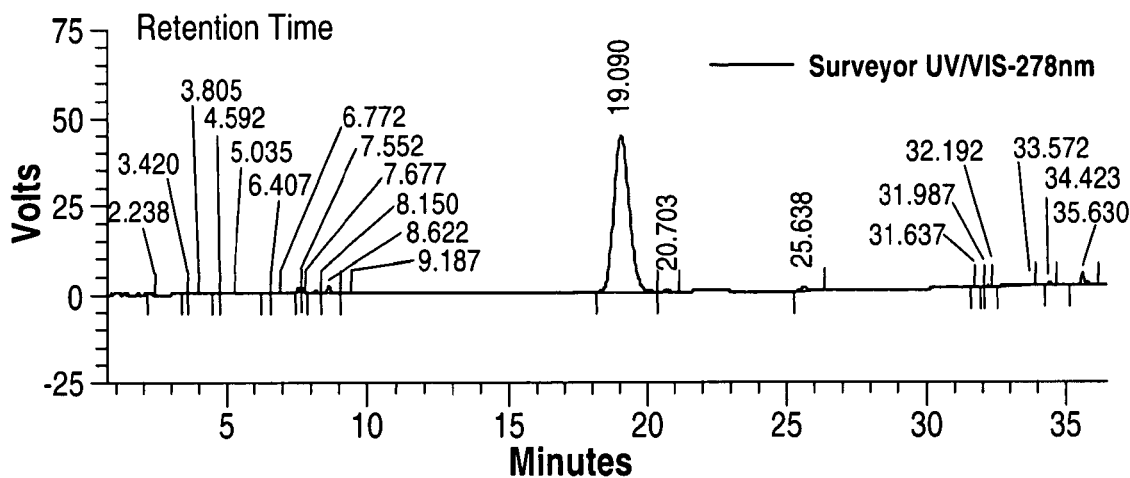
FIGS. 29A and 29B show HPLC chromatograms of Compound B control overlaid with the Compound B assay results obtained from a pre-cure derived biomaterial after final curing.
Figure 29B:
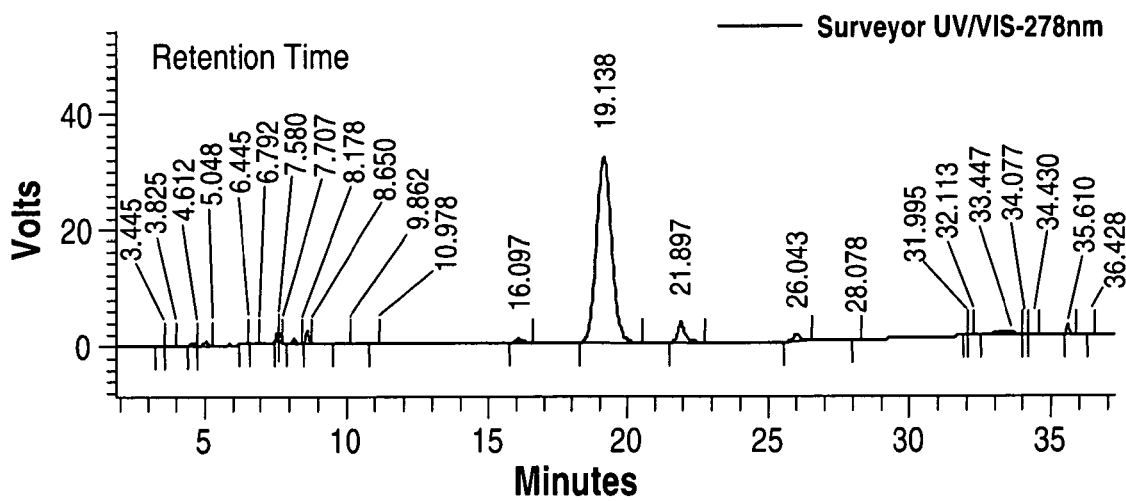

Further evidence for the preservation of the drug structure in the Compound B is shown by the Compound B HPLC assay results presented in Table 10. The average Compound B recovery in formulation is approximately 62% on coupons where it was only approximately 9% when only present as a drug powder. Average vitamin E recovery in the coating, however, trends lower from 81% by itself after final cure down to 68% in formulation. Analysis of the Compound B HPLC chromatograms from the fatty-acid based, pre-cure-derived coating formulation indicates that drug degradation is greatly reduced in comparison to the drug only results (FIG. 27C versus FIG. 29B).

Figure 12:
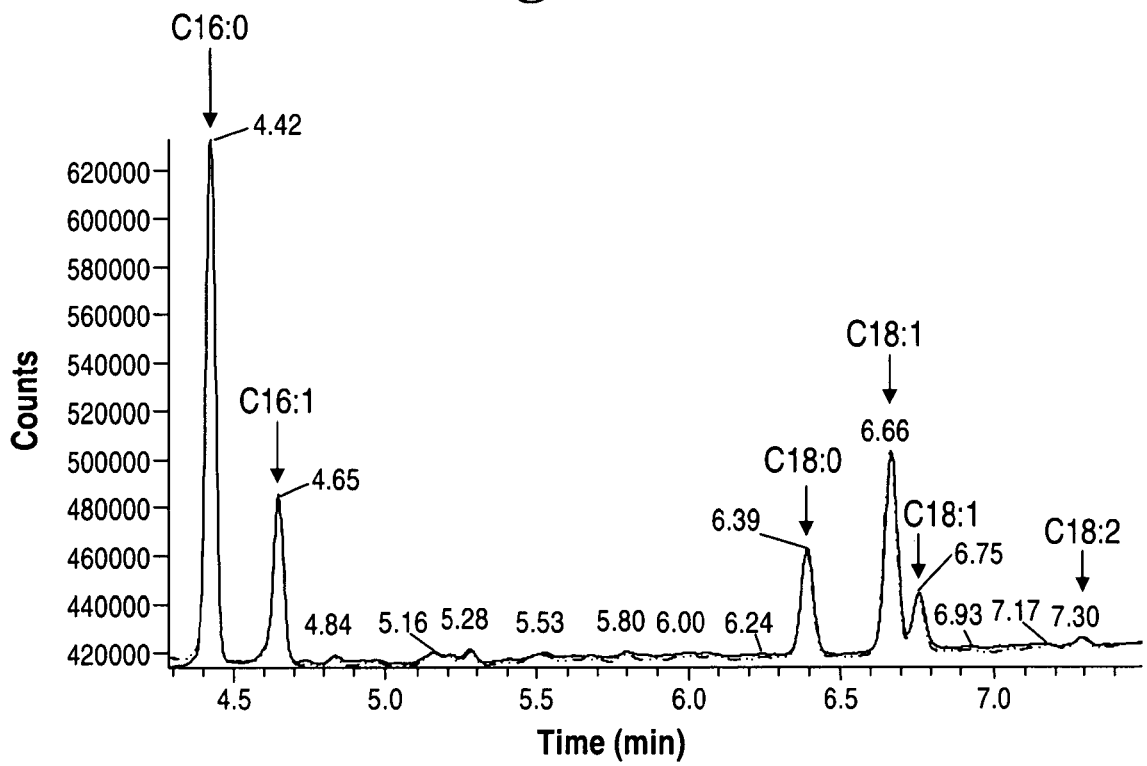
FIG. 12 shows the fatty acid profile chromatogram acquired for a therapeutic agent/biomaterial formulation sprayed on coupons with and without final curing.
Figure 30:
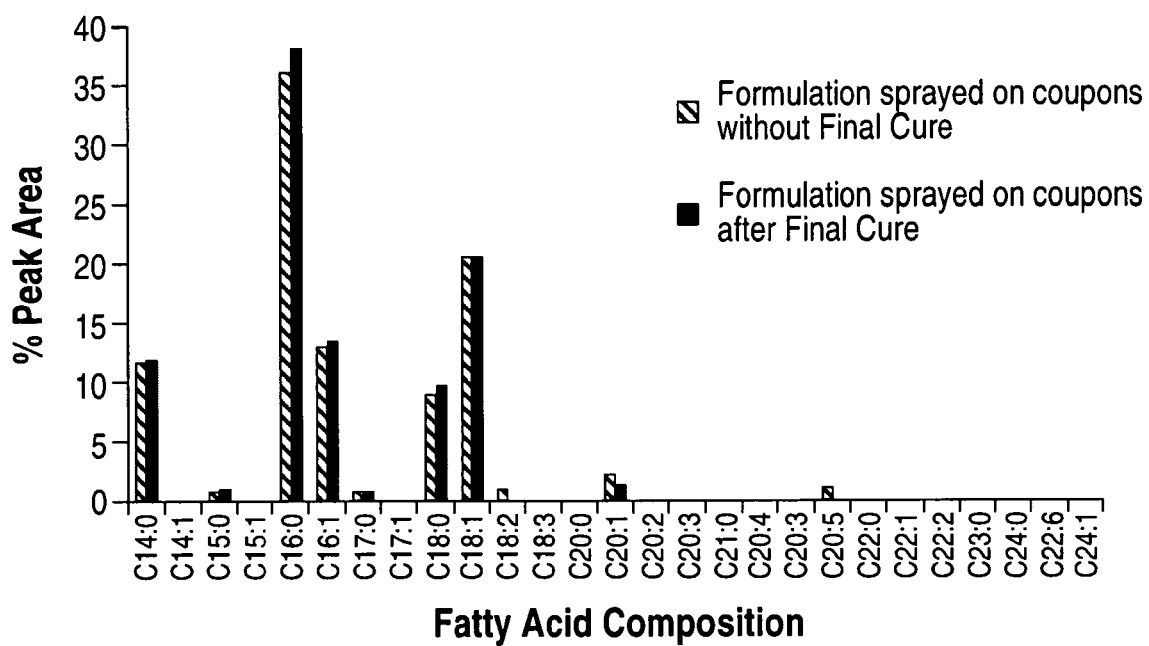
FIG. 30 shows fatty acid profile data acquired for a therapeutic agent/biomaterial formulation sprayed on coupons with and without final curing.

GC fatty acid compositional analysis of the Compound B oil-derived biomaterial formulation before and after final curing revealed that there was a marked reduction of oxidation of the fatty acids in the fish oil in formulation in comparison to when cured by itself (FIG. 23 versus FIG. 30). Because vitamin E is an antioxidant (i.e., oxidizes at a faster rate than fish oil) this result is not unexpected. The inhibition of oxidation of the unsaturated fatty acids of the oil component is also observed in the native GC chromatogram before and after final curing (FIG. 12).

TABLE 10

Summary of Compound B HPLC Assay Results

| Sample Description | % Recovery | Standard Deviation | % RSD |
|---|---|---|---|
| Compound B Powder Control | 96 | 0.04 | 0.04 |
| Compound B in 75:25 pre-cured fish oil:vitamin E with MTBE sprayed onto coupon without final cure. | 97.8 | 0.97 | 0.99 |
| Compound B in 75:25 pre-cured fish oil:vitamin E with MTBE sprayed onto coupon after final cure. | 61.9 | 14.78 | 23.86 |

Example 11: In-Situ Kinetic Analysis of Compound B Fatty Acid Based, Pre-Cure Derived Coating Using FTIR, and HPLC Analysis In this experiment, 60% Compound B in 30% pre-cured fish oil, and vitamin E was dissolved into MTBE and spray coated onto 3.5×13 mm cobalt chromium stents in order to correlate the model coupon experiments in Examples 3 and 4 to the Compound B oil-derived biomaterial stent coating process. The coated stents were placed in the oven to cure at 200° F. and samples were removed every hour of the 6 hour curing process. FTIR spectroscopic analysis was performed at every time point. Compound B and vitamin E HPLC assay testing was performed at T=0, 3, and 6 hr curing points.

Figure 17:
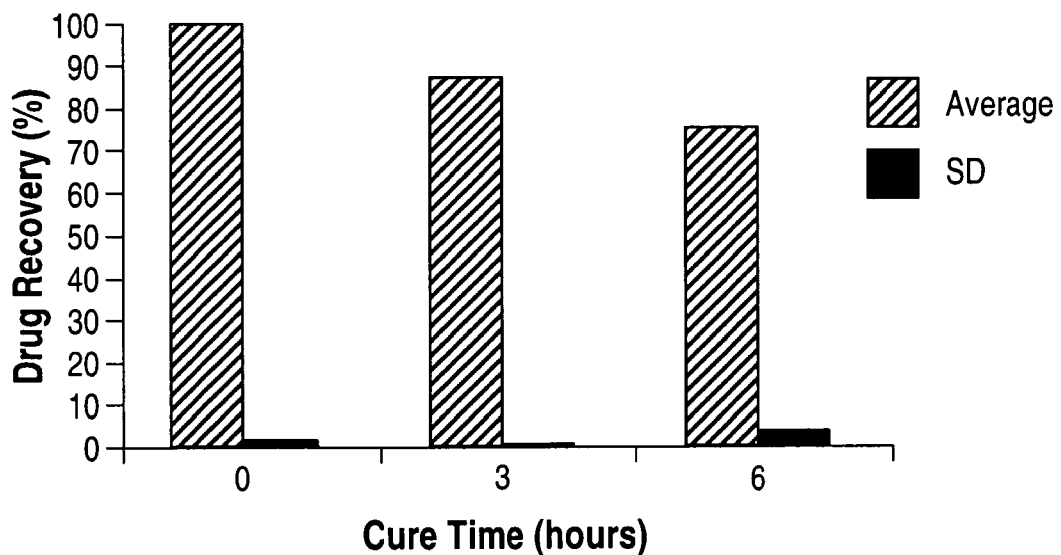
FIG. 17 shows assay recovery results from Co—Cr stents as a function of final cure time.
Figure 31A:
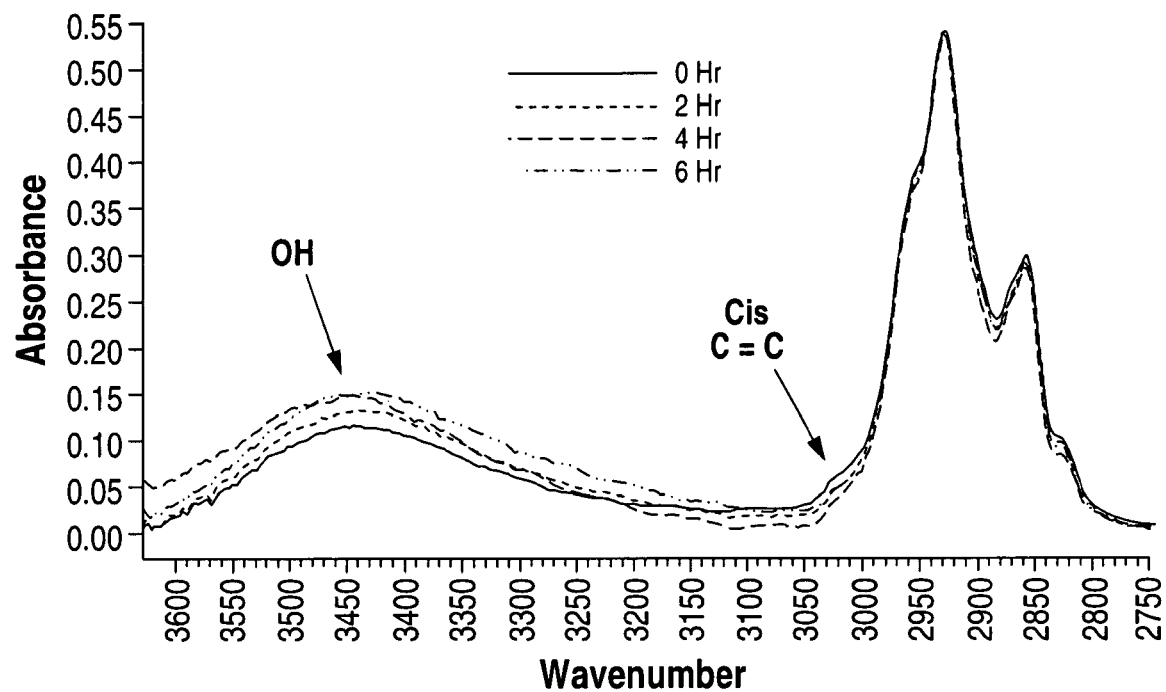
FIGS. 31A, 31B and 31C show FTIR spectra of a therapeutic agent in 75:25 pre-cured fish oil: vitamin E sprayed onto stents and cured at various times.
Figure 31B:
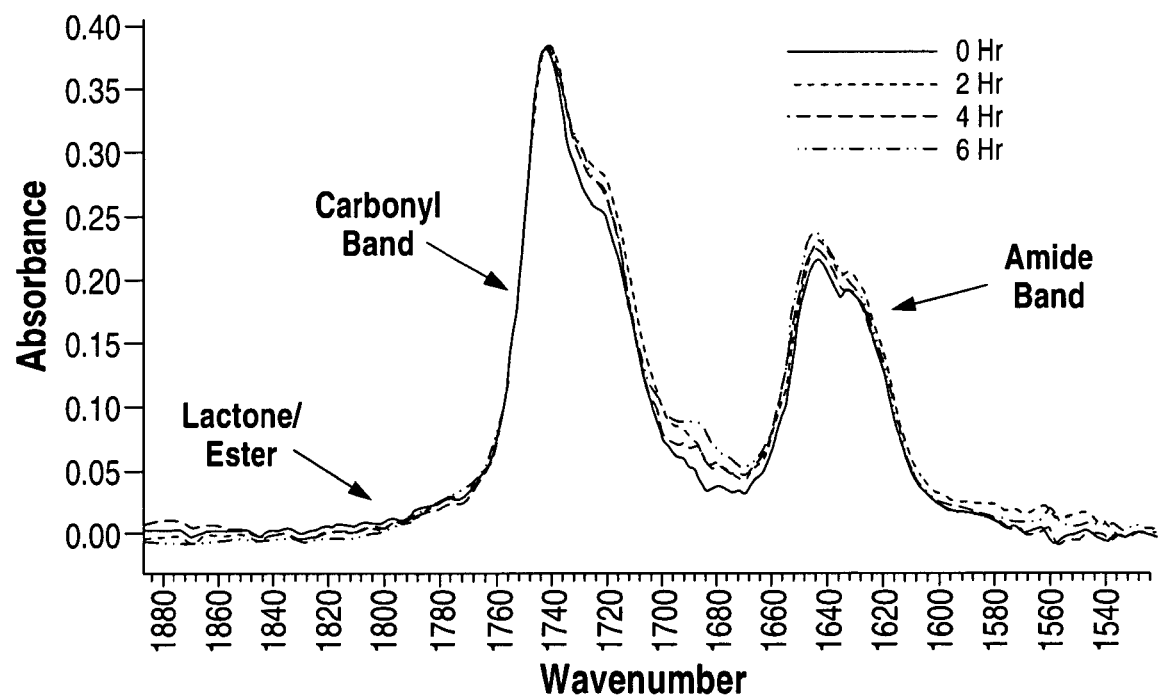
Figure 31C:
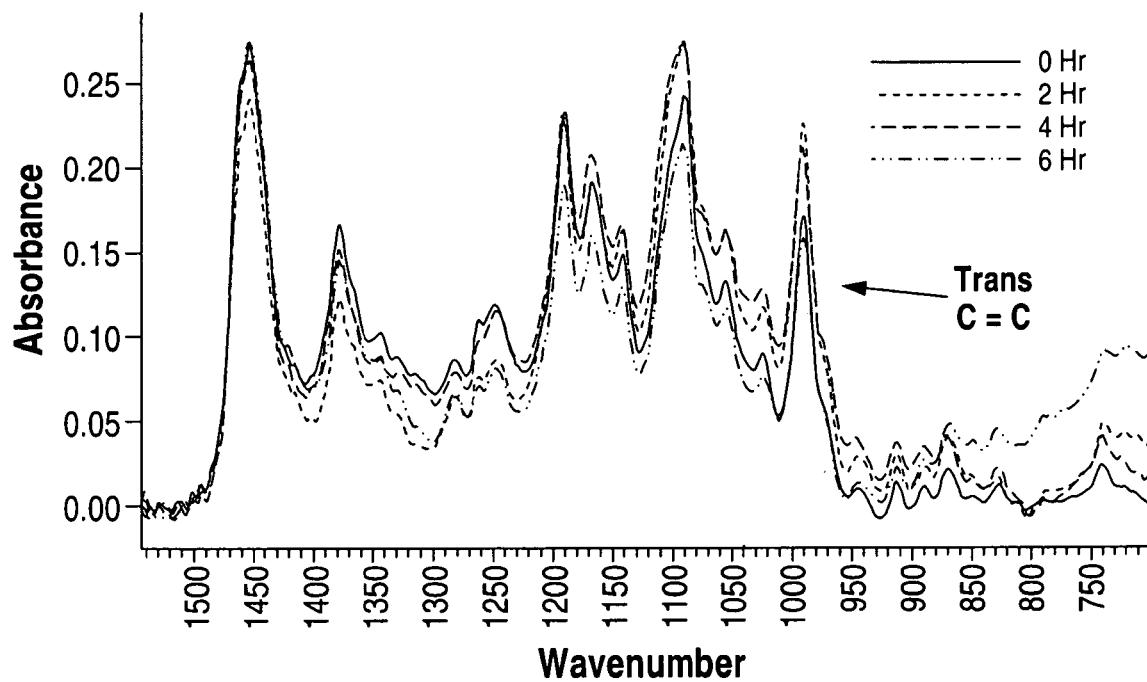

FTIR analysis performed at various time points (FIGS. 31A, 31B and 31C) revealed a similar trend in final chemistry to those obtained for the Compound B oil-derived formulation on coupons (FIG. 28). Specifically, only small shifts in absorption bands could be noted, but no extreme loss in Compound B structure was noted in comparison to the Compound B drug powder FTIR coupon experiments (FIG. 26 versus FIG. 31). HPLC assay testing performed on the stent samples at T=0, 3, and 6 hrs for the Compound B is presented in FIG. 17. The Compound B shows decreased recovery as a function of cure time with final curing recovery averaging 75% for Compound B due to oxidation of the drug, but to a much less degree than the Compound B drug powder subjected to heating alone, which only yielded a 9% recovery. The vitamin E assay results trend similarly to the Compound B where there is a decrease in recovery as a function of time with a final recovery of 69% being obtained.

Example 12: Summary of Mechanism of Fatty Acid Based, Pre-Cure Derived Stent Coating Formation From the experiments performed in Examples 11-13 several conclusions can be drawn from the data to elucidate the chemistry of formation of the Compound B oil-derived, pre-cured biomaterial stent coating. In Example 11, each formulation component in MTBE was sprayed onto coupons and then post cured onto the coupon surface in order to determine the changes in chemistry for each component in the process. Analysis of the pre-cured fish oil only coupons revealed that final curing further oxidizes the double bonds present, as no cis C═C bonds are retained. Additional lactone cross-linking and carbonyl byproduct formation are detected. GC fatty acid profile analysis of the pre-cured fish oil only coupons before and after post-curing was also consistent with oxidation of the fish oil fatty acid double bonds. FTIR analysis of the vitamin E only coupons also determined that the final curing process resulted in oxidation of the vitamin E. This was evidenced by the formation of a vitamin E byproduct peak in the carbonyl absorption region and a loss of the phenol OH absorption band. Oxidation was confirmed by HPLC assay, which showed a 20% loss of vitamin E recovery after final curing. Finally, testing of the Compound B drug powder sprayed onto coupons showed that that dissolving the drug in solvent and spraying it onto the coupons is changing the Compound B structure when compared to the control powder spectrum (i.e., shift in amide absorption band).

After final cure the Compound B drug powder chemical structure is significantly altered as evidenced by several absorption mode changes by FTIR, only 9% recovery of the Compound B was obtained by HPLC assay, and byproduct peaks indicating degradation were present in the HPLC chromatogram. Although the results of these studies clearly show oxidation of the vitamin E, pre-cure fish oil, and Compound B drug powder components through the final curing process, these results suggest that that there is an additional interaction between the formulation components (i.e., vitamin E and pre-cured fish oil) when mixed together then when subjected to the final curing process as typical Compound B HPLC assay results range between 75-85% recovery of the Compound B from oil-derived stent coatings.

In the second group of experiments, the Compound B, pre-cured fish oil and vitamin E were mixed in MTBE and sprayed onto coupons, and samples were analyzed before and after the final post-cure process step. These data revealed a significant increase in the preservation of the drug structure as evidenced in the FTIR spectra and the greater of recovery of drug from the coating (i.e., ~62%) as determined by HPLC assay. Byproduct peaks for the Compound B were still detected by HPLC, but were much less intense than those detected when the drug was subjected to the final post-cure process by itself. The pre-cured fish oil, when formulated with vitamin E, showed a decrease in oxidation in formulation when compared to the pre-cured fish oil with no vitamin E as detected in GC fatty acid compositional analysis (FIG. 23 vs. FIG. 12). However, lactone/ester cross-linking was still observed.

In general, the results obtained from the stent studies mirrored those obtained from the coupon formulation studies, except that the average Compound B recovery was increased to 75%.

Based on the experiments conducted in this study several conclusions can be obtained. After spraying, the coating applied to the stent appears non-uniform and after heating the coating spreads across the surface of the stent, the pre-cured fish oil cross-links, and a uniform coating is produced. The recovery of the Compound B from formulation is significantly greater than the recovery obtained when assaying the Compound B by itself (9%), showing that the formulation (i.e., Vitamin E) is providing some protection to the drug stability.

Analysis of the vitamin E in formulation showed that it is oxidizing as a result of the final curing process using both FTIR and HPLC testing, but the pre-cured fish oil is less oxidized as detected by GC fatty acid profile. Similar to the Compound B analytical data, this result indicates that the vitamin E is providing protection to the oil during the oxidation process. However, despite the presence of the vitamin E, lactone/ester cross-linking in the fish oil component in formulation on coupons after final curing could still be detected. Lactone/ester cross-linking can still occur in the oil-derived biomaterial coating because the fish oil used in the formulation is pre-cured before use. Partially curing the fish oil creates carboxyl and hydroxyl functional groups that are needed to form lactone/ester cross-links, and thus the presence of the vitamin E in the final curing step only serves to reduce additional oxidation, but cannot reverse the oxidation or the molecular species already formed in the pre-cured oil.

As can be seen, by, for example, preserving the structure of the therapeutic agent, the therapeutic agent will have an enhanced release profile when released from the coating.

Example 13: Method of Producing a Fatty Acid Based, Pre-Cure Derived Coating on a Stent Using Compound E Pre-cured fish oil (PCFO) was prepared by heating fish oil in a reactor at 93° C. for a total of 23 hours, while infusing oxygen through a diffuser. The resultant viscosity of the pre-cured fish oil was $1\times10^6$ cps. The coating formulation consisting of 70% Compound E, 22.5% PCFO, and 7.5% Vitamin E was made by combining 18.5 mg PCFO, 6.4 mg Vitamin E, 57.9 mg Compound E, and 8.20 g of methyl-tert-butyl-ether (MTBE) (Sigma Chemicals) to produce a coating solution having of 99% solvent, 1% solids for spray coating. This solution was vortexed for 30 min until clear. Atrium Cinatra™ CoCr stents (3.5×13 mm) were spray coated using a SonoTek Medicoat DES 1000 ultrasonic Spray System. The target coating load was 100 µg Compound E per stent with an actual coating weight of 133.28 µg, which results in a calculated drug load of 93.2 µg based upon the calculated final drug fraction in the coating. Coated stents were cured in an oven set to 93° C. for 6 hours. This process yields a dry, non-tacky, conformal stent coating having a smooth surface characteristic when imaged using scanning electron microscopy (SEM).

In a related but separate experiment, 20 µL of the same drug coating formulation described above was pipetted onto Cobalt Chromium coupons with a target drug load of 100 µg of Compound E. The coated coupons were post cured in an oven at 93° C. for 6 hours. Gravimetric measurements of the coated coupons following the final 6 hour post curing process demonstrated an average coating load of 152.603 µg which based upon a calculated drug fraction of 69.92% Compound E results in an average drug load per coupon of 106.7 µg of Compound E. Following post curing the drug coating was extracted from the coupon in a 100% acetonitrile solution and analyzed via HPLC to determine the drug concentration in solution, from which the total drug mass extracted from the coupon was determined. The total drug mass extracted from the coupons along with the actual coating weight on the coupon determined gravimetrically is used to calculate the percent of drug applied to the coupon in coating which is recovered following the post curing process. The percent drug recovery from coating cured on the CoCr coupons for 6 hrs at 93° C. was calculated to be 96.7%. The drug recovery data clearly shows that the drug integrity is preserved through the coating formulation, application and most importantly the thermal post curing process.

Example 14: Method of Producing a Fatty Acid Based, Pre-Cure Derived Coating on a Stent Using Therapeutic Agent Compound D Pre-cured fish oil (PCFO) was prepared by heating fish oil in a reactor at 93° C. for a total of 23 hours, while infusing oxygen through a diffuser. The resultant viscosity of the pre-cured fish oil was $1\times10^6$ cps. The Compound D drug coating formulation consisting of 50% Compound D, 37.5% PCFO, and 12.5% Vitamin E was made by combining 55.4 mg PCFO, 18.5 mg Vitamin E, 74.3 mg Compound D, and 14.67 g solvent solution consisting of 60% methyl-tert-butyl-ether (MTBE) 40% acetone to produce a coating solution having 99% solvent, 1% solids for spray coating. This solution was vortexed for 30 min until clear. Atrium Cinatra™ CoCr stents (3.5×13 mm) were spray coated using a SonoTek Medicoat DES 1000 ultrasonic Spray System. The target coating load was 100 µg Compound D per stent with an actual coating weight of 164.16 µg, which results in a calculated drug load of 82.3 µg based upon the calculated final drug fraction in the coating. Coated stents were cured in an oven set to 93° C. for 6 hours. This process yields a dry, non-tacky, conformal stent coating having a smooth surface characteristic when imaged using scanning electron microscopy (SEM).

In a related but separate experiment, 40 µL of the same drug coating formulation described above was pipetted onto Cobalt Chromium coupons with a target drug load of 100 µg of sirolimus drug. The coated coupons were post cured in an oven at 93° C. for 6 hours. Gravimetric measurements of the coated coupons following the final 6 hour post curing process demonstrated an average coating load of 305.59 µg which based upon a calculated drug fraction of 50.13% sirolimus results in an average drug load per coupon of 153.1 µg of sirolimus. Following post curing the drug coating was extracted from the coupon in 80% methanol, 20% (0.2% acetic acid) solution and analyzed via HPLC to determine the drug concentration in solution, from which the total drug mass extracted from the coupon was determined. The total drug mass extracted from the coupons along with the actual coating weight on the coupon determined gravimetrically is used to calculate the percent of drug applied to the coupon in coating which is recovered following the post curing process. The percent drug recovery from coating cured on the CoCr coupons for 6 hrs at 93° C. was calculated to be 71.5%. The drug recovery data clearly shows that the drug integrity is preserved through the coating formulation, application and most importantly the thermal post curing process. Although the sirolimus drug recovery is less than 100% in this example, the recovery is far better than the near zero percent recovery obtained when the pre-curing of the fish oil step is removed and all coating curing occurs in the final coating with the drug included.

Example 15: In-Vivo Performance and Biological Response of a Coronary Stent Coated with a Cross Linked Fatty Acid Based Coating Incorporating a Therapeutic Agent In this study, a coating formulation containing 50% Compound D, 37.5% pre-cured fish oil and 12.5% tocopherol was prepared using pre-cured fish oil having a viscosity of $1\times10^5$ cps, as measured at 25° C. The coating formulation was subsequently sprayed onto 3.0 mm×13 mm and 3.5 mm×13 mm Atrium Cinatra CoCr stents using a Badger airbrush equipped with a medium sized needle. Following the spray coating application of the coating to the stents, the coated stents were oven post cured at 93° C. for 6 hours to achieve a uniform and conformal drug coating layer. The final drug load per stent, as measured by HPLC, was 68 µg of Compound D. Following post curing, coated stents were crimped onto 3.0 mm×14 mm and 3.5 mm×14 mm PTCA catheters respectively, the devices were subsequently packaged and sterilized via e-beam sterilization with a nominal dose of 35 kgy. The sterile drug coated stent devices were then used to conduct a pre-clinical study in a porcine model, where by single stents were implanted into three coronary vessels, the Left Anterior Descending Artery (LAD), the Left Circumflex Artery (L CX) and the Right Coronary Artery (RCA) of the porcine heart. Three groups of stents were implanted: 1) Bare metal stents, 2) stents with coating alone (no drug) and 3) drug coated stents (DCS) to assess their comparative biological response. All stents were implanted with an appropriate expansion to achieve a stent to vessel diameter ratio of 1.10:1. Post implantation, animals were recovered and were maintained for 28±2 days, at which time the animals were sacrificed and the hearts harvested D. This response is consistent with what has been observed with other commercial stent products containing Compound D or analogues with a similar mechanism of action. Lastly, the percent endothelialization indicates the degree to which the stent and stented vessel segment is covered with an endothelial monolayer (an endothelial monolayer being the most intimal cell/tissue layer present in a normal functioning arterial vessel and is critical in preventing thrombosis). The endothelialization data shows essentially 100% re-endothelialization of the stented vessel segment across all three groups, indicating that neither the base coating nor drug coating interfere with the endothelial healing process.

TABLE 11

Figure 32:
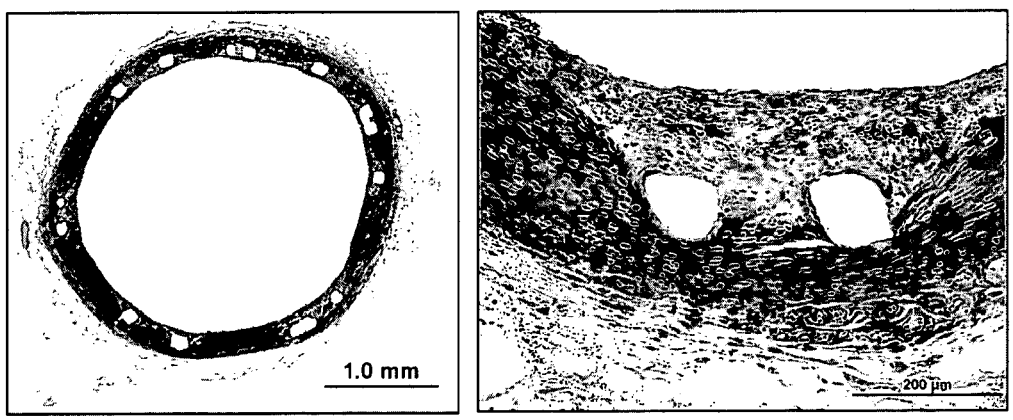
FIGS. 32, 33 and 34 show results from the in vivo experiments described in Example 15.
Figure 33:
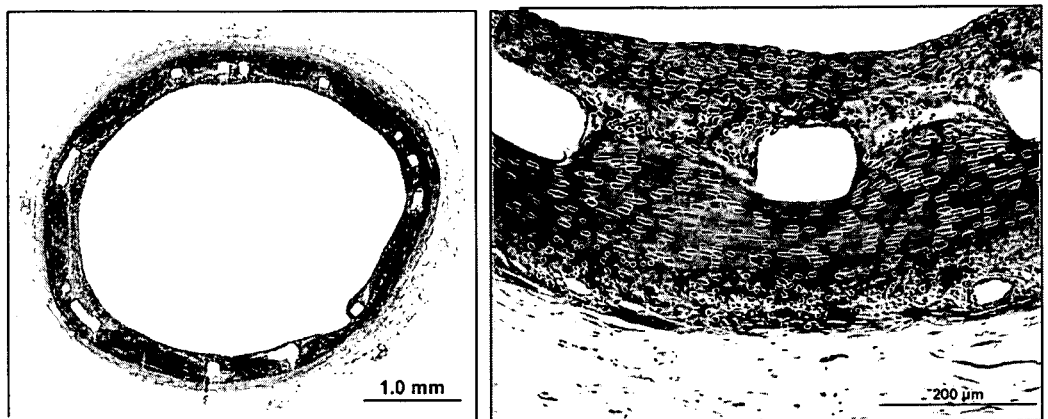
Figure 34:
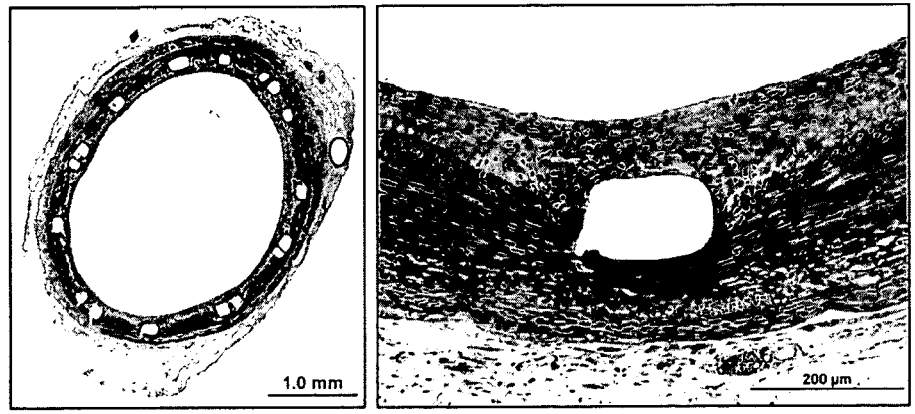

| Implant Group | Mean Injury Score | Mean Intimal Inflammation Score | Mean % Area Stenosis | Mean Fibrin Scores | % Endothelialization |
|---|---|---|---|---|---|
| BMS | 0.35 ± 0.24 | 0.29 ± 0.42 | 18.94 ± 6.58 | 0.29 ± 0.21 | 99.67 ± 0.94 |
| Coating Alone (no Drug) | 0.51 ± 0.27 | 0.50 ± 0.53 | 23.39 ± 6.05 | 0.21 ± 0.31 | 100.00 ± 0.00 |
| DCS | 0.47 ± 0.16 | 0.37 ± 0.99 | 22.07 ± 7.38 | 1.96 ± 0.75 | 99.92 ± 0.15 | and fixed in formalin. Following fixation, the stented vessels were isolated and dissected from the heart. The stented arteries were dissected and embedded in methylmethacrylate for sectioning and histopathologic evaluation. Sections were taken from the proximal portion, mid portion, and distal portion of each stent. The images in FIG. 32 are representative vessel cross sections having a BMS stent. The images in FIG. 33 are representative vessel cross sections having a stent with coating alone (no drug). The images in FIG. 34 are representative vessel cross sections having a DCS stent. As can be seen in these comparative images there is no notable difference in the overall tissue reaction among the three groups with the exception of higher levels of fibrin found in the DCS (discussed below). A comprehensive and quantitative analysis of histomorphometry and histopathology was assessed as part of this study, the specific results for mean injury score, mean intimal inflammation, mean percent diameter stenosis, mean fibrin score and % endothelialization for all three groups and are tabulated in table 11. As can be seen in table 11, the mean injury scores across the three groups are very similar (no statistical difference), indicating that there were no significant differences between groups in regards to the level of mechanical vessel injury induced during stent implantation. Generally, an injury score of less than 1 is considered to be low. Similar to the injury scores, the mean intimal inflammation scores are similar across all groups (no statistical difference) indicating that the inflammation associated with both the coating alone (no drug) and the DCS was the same as that of a stent with no coating at all. The mean % diameter stenosis data indicates no significant difference in cellular proliferation among groups with all groups showing low overall % diameter stenosis at the 28 day time point. This level of cellular proliferation amoung the various experimental groups is not unexpected, as the 1.10:1 overstretch results in relatively low injury during the stent implantation process. The mean fibrin score, which is used as an indicator for the biological drug response, clearly shows that the BMS and coating alone groups have similarly low fibrin scores, while the fibrin scores for the DCS group are significantly higher, indicating that the drug has been effectively delivered to the locally stented vessel segment, demonstrating a clear biological response to the Compound Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present invention has been described in conjunction with various embodiments and examples, it is not intended that the present teachings be limited to such embodiments or examples. On the contrary, the present invention encompasses various alternatives, modifications, and equivalents, as will be appreciated by those of skill in the art.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

The invention claimed is:

1. A coating for a medical device obtainable by curing fatty acid based material, wherein the fatty acid based material is an oil, and adding a therapeutic agent comprising sirolimus, wherein the fatty acid was partially cross-linked before association with the therapeutic agent forming a precured material, additionally curing the fatty acid based material after addition of the therapeutic agent.

2. The coating of claim 1, wherein the oil comprises 5-25% $C_{14}$ fatty acids and wherein the oil comprises 5-30% $C_{16}$ fatty acids.

3. The coating of claim 1, wherein the medical device is a stent.

4. The coating of claim 2, wherein the medical device is a stent.

5. The coating of claim 1, wherein the medical device is a CoCr stent.

6. The coating of claim 2, wherein the medical device is a CoCr stent.

7. The coating of claim 1, wherein the coating comprises approximately 30-90% saturated fatty acids.

8. The coating of claim 1, wherein the coating is configured to produce a glyceride upon metabolization in-vivo.

9. The coating of claim 1, wherein the oil is a fish oil, olive oil, grape oil, palm oil, or flaxseed oil.

10. The coating of claim 1, wherein the oil is a fish oil.

11. A fatty-acid based, pre-cure-derived coating for a medical device, comprising:
a non-polymeric, partially cross-linked fatty acid, and a therapeutic agent that is degradable by curing, wherein the therapeutic agent is contained within the coating in such a manner that the therapeutic agent has an enhanced profile as therapeutic agent degradation in the coating results only from curing after the therapeutic agent is added to a partially cross-linked fatty-acid based pre-cure to form the non-polymeric, partially crosslinked fatty acid.

12. The coating of claim 11, wherein the therapeutic agent comprises sirolimus and the medical device is a CoCr stent.

13. The coating of claim 11, wherein the therapeutic agent comprises sirolimus and the medical device is a stent.

14. A preparation for deriving a coating for a medical device, the preparation comprising:
a non-polymeric, partially cross-linked fatty acid, and a therapeutic agent, wherein the coating contains ester and lactone cross-links, the therapeutic agent comprises sirolimus, and the medical device is a CoCr stent.

15. A coating for a medical device, comprising:
a cross-linked fatty acid oil, and a therapeutic agent, wherein the fatty acid was partially cross-linked before association with the therapeutic agent, wherein the therapeutic agent comprises sirolimus and the medical device is a CoCr stent.

16. The coating of claim 1, wherein the coating comprises approximately 30-80% unsaturated fatty acids.

17. The coating of claim 1, wherein the coating comprises approximately 50-90% saturated fatty acids.

18. The coating of claim 1, wherein the coating comprises approximately 10-50% unsaturated fatty acids.

19. The coating of claim 8, wherein the coating releases the therapeutic agent at a desired release rate in vivo.

20. The coating of claim 19, wherein the coating has a release profile of the therapeutic agent in 0.01 M phosphate buffered saline (PBS) out to one of about 5-20 days or more than 20 days.

* * * * *